United States Patent
Burwinkel et al.

(10) Patent No.: US 10,316,367 B2
(45) Date of Patent: Jun. 11, 2019

(54) CIRCULATING MIRNAS AS MARKERS FOR BREAST CANCER

(71) Applicant: Ruprecht-Karls-Universität Heidelberg, Heidelberg (DE)

(72) Inventors: Barbara Burwinkel, Heidelberg (DE); Katarina Cuk, Heidelberg (DE); Manuela Zucknick, Oslo (NO); Dharanija Madhavan, Heidelberg (DE)

(73) Assignee: RUPRECHT-KARLS-UNIVERSITÄT HEIDELBERG, Heidelberg (DE)

( * ) Notice: Subject to any disclaimer, the term of this patent is extended or adjusted under 35 U.S.C. 154(b) by 312 days.

(21) Appl. No.: 14/409,953

(22) PCT Filed: Jun. 21, 2013

(86) PCT No.: PCT/EP2013/062994
§ 371 (c)(1),
(2) Date: Dec. 19, 2014

(87) PCT Pub. No.: WO2013/190091
PCT Pub. Date: Dec. 27, 2013

(65) Prior Publication Data
US 2015/0197812 A1 Jul. 16, 2015

Related U.S. Application Data

(60) Provisional application No. 61/662,816, filed on Jun. 21, 2012, provisional application No. 61/813,029, filed on Apr. 17, 2013.

(51) Int. Cl.
*C12Q 1/68* (2018.01)
*C12Q 1/6886* (2018.01)

(52) U.S. Cl.
CPC ....... *C12Q 1/6886* (2013.01); *C12Q 2600/16* (2013.01); *C12Q 2600/178* (2013.01)

(58) Field of Classification Search
None
See application file for complete search history.

(56) References Cited

U.S. PATENT DOCUMENTS

2011/0021607 A1* 1/2011 Clarke ............... C12Q 1/6886
514/44 A

FOREIGN PATENT DOCUMENTS

| WO | WO 2007/112754 A2 | 10/2007 |
| WO | WO 2012/040500 A2 | 3/2012 |
| WO | WO 2012/048236 A1 | 4/2012 |

OTHER PUBLICATIONS

Handbook of Chemistry and Physics, 49th Edition, 1968, Weast (ed.), The Chemical Rubber Co., Cleveland, Ohio, p. A-245.*
Lu et al, Nature 435: 834 (2005).*
International Preliminary Report on Patentability issued in related International Patent Application No. PCT/EP2013/062994, dated Dec. 31, 2014.
Jemal, et al., "Global Cancer Statistics," CA Cancer J Clin, vol. 61, pp. 69-90 (2011).
Taplin, et al., "Mammography facility characteristics associated with interpretive accuracy of screening mammography," J Natl Cancer Inst., vol. 100, pp. 876-887 (2008).
Uehara, et al., "Long-term prognostic study of carcinoembryonic antigen (CEA) and carbohydrate antigen 15-3 (CA 15-3) in breast cancer," Int J Clin Oncol, vol. 13, pp. 447-451 (2008).
Harris, et al., "American Society of Clinical Oncology 2007 update of recommendations for the use of tumor markers in breast cancer," J Clin Oncol, vol. 25, pp. 5287-5312 (2007).
Cristofanilli, et al., "Circulating tumor cells, disease progression, and survival in metastatic breast cancer," N Engl J Med., vol. 351, No. 8, pp. 781-791 (2004).
Bartel, "MicroRNAs: genomics, biogenesis, mechanism, and function," Cell, vol. 116, pp. 281-297 (2004).
Calin, et al., "Frequent deletions and down-regulation of micro-RNA genes miR15 and miR16 at 13q14 in chronic lymphocytic leukemia," Proc Natl Acad Sci., vol. 99, pp. 15524-15529 (2002).
Lawrie, et al., "Detection of elevated levels of tumour-associated microRNAs in serum of patients with diffuse large B-cell lymphoma," Br J Haematol., vol. 141, pp. 672-675 (2008).
Brase, et al., "Circulating miRNAs are correlated with tumor progression in prostate cancer," Int J Cancer, vol. 128, pp. 608-616 (2011).
Huang, et al., "Plasma microRNAs are promising novel markers for early detection of colorectal cancer," Int J Cancer, vol. 127, pp. 118-126 (2010).
Zhang, et al., "Expression profile of microRNAs in serum: a fingerprint for esophageal squamous cell carcinoma," Clin Chem., vol. 56, pp. 1871-1879 (2010).

(Continued)

*Primary Examiner* — James Martinell
(74) *Attorney, Agent, or Firm* — Foley & Lardner LLP

(57) ABSTRACT

The present invention is directed to methods for diagnosing breast cancer, metastasizing breast cancer, or for determining the CTC status in a subject. Moreover, the present invention is concerned with devices and kits for carrying methods of the invention. The methods comprise determining in a sample of a subject suspected to be afflicted with breast cancer the amount of at least one miRNA selected from a recited list of miRNAs, followed by comparing the amount with one or more references, whereby breast cancer is to be diagnosed.

4 Claims, 42 Drawing Sheets
Specification includes a Sequence Listing.

(56) References Cited

OTHER PUBLICATIONS

Mitchell, et al., "Circulating microRNAs as stable blood-based markers for cancer detection," Proc Natl Acad Sci., vol. 105, pp. 10513-10518 (2008).
Turchinovich, et al., "Characterization of extracellular circulating microRNA," Nucleic Acids Res., vol. 39, pp. 7223-7233 (2011).
Arroyo, et al., "Argonautez complexes carry a population of circulating microRNAs independent of vesicles in human plasma," Proc Natl Acad Sci., vol. 108, pp. 5003-5008 (2011).
Griffiths-Jones, "The microRNA Registry," Nucleic Acids Research, vol. 32, pp. D109-D111 (2004).
Kozomara, et al., "miRBase: integrating microRNA annotation and deep-sequencing data," Nucleic Acids Research, vol. 39, pp. D152-D157 (2011).
Breast Cancer Facts & Figures 2011-2012, issued by the American Cancer Society, Inc., 36 pages.
Dumitrescu, et al., Understanding breast cancer risk—where do we stand in 2005? Journal of Cellular and Molecular Medicine, vol. 9, No. 1, pp. 208-221 (2005).
Bradbury, et al, "Genetic susceptibility to breast cancer," Reviews in Endocrine and Metabolic Disorders, vol. 8, No. 3, pp. 255-267 (2007).
Cissell, et al., "Trends in microRNA detection," Anal Bioanal Chem., vol. 394, No. 4, pp. 1109-1116 (2009).
de Planell-Saguer, et al., "Analytical aspects of microRNA in diagnostics: a review," Anal Chim Acta vol. 699, No. 2, pp. 134-152 (2011).
Zweig, "Receiver-Operating characteristic (ROC) Plots: A Fundamental Evaluation Tool in Clinical Medicine," Clin. Chem., vol. 39, No. 4, pp. 561-577 (1993).
Smyth, "Linear models and empirical bayes methods for assessing differential expression in microarray experiments," Statistical Applications in Genetics and Molecular Biology, vol. 3, No. 1, Article 3, 27 pages (2004).
Benjamini, et al., "Controlling the False Discovery Rate: A Practical and Powerful Approach to Multiple Testing," Journ. Royal Statistical Society Series B (Methodological), vol. 57, pp. 289-301 (1995).
Kroh, et al., Analysis of circulating microRNA biomarkers in plasma and serum using quantitative reverse transcription-PCR (qRT-PCR), Methods, vol. 50, pp. 298-301 (2010).
Fawcett, "An introduction to ROC analysis," Pattern Recognition Letters 27, pp. 861-874. (2006).
Hayes, et al., Breast cancer, American Journal Committee on Cancer, Cancer Staging Manual (seventh edition), pp. 345-376 (2010).
Mantel, "Evaluation of survival data and two new rank order statistics arising in its consideration," Cancer Chemotherapy Reports, vol. 50, No. 3, pp. 163-170 (1996).
Madhavan et al., "Circulating miRNAs as Surrogate Markers for Circulating Tumor Cells and Prognostic Markers is Metastatic Breast Cancer", Clinical Cancer Research, vol. 18, No. 21, pp. 5972-5982 (2012).
Cuk et al., "Circulating microRNAs in plasma as early detection markers for breast cancer", Intern. Journ. of Cancer, vol. 132, No. 7, pp. 1602-1612 (2013).
Zhao et al., "A Pilot Study of Circulating miRNAs as Potential Biomarkers of Early Stage Breast Cancer", PLOS One, vol. 5, No. 10, e13735, 12 pages. (2012).
Marilena, et al., "MicroRNA gene expression deregulation in human breast cancer" Cancer Research, vol. 65, No. 16, pp. 7065-7070 (2005).
Roth et al., "Circulating microRNAs as blood-based markers for patients with primary and metastatic breast cancer," Breast Cancer Research, vol. 12, No. 6, 8 pages (2010).
International Search Report issued in related International Patent Application No. PCT/EP2013/062994, completed Aug. 30, 2013.

* cited by examiner

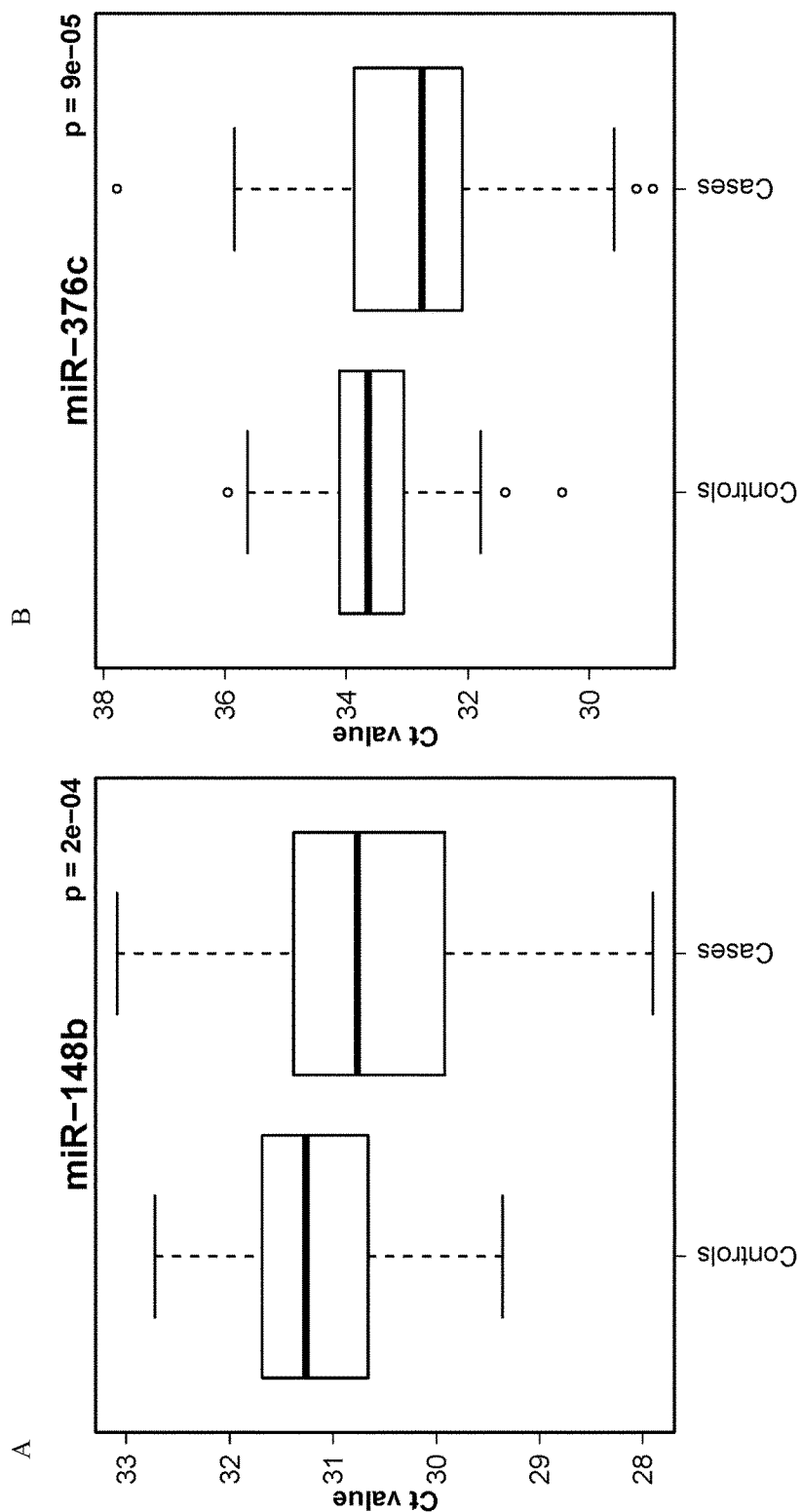
Fig. 1 A, B

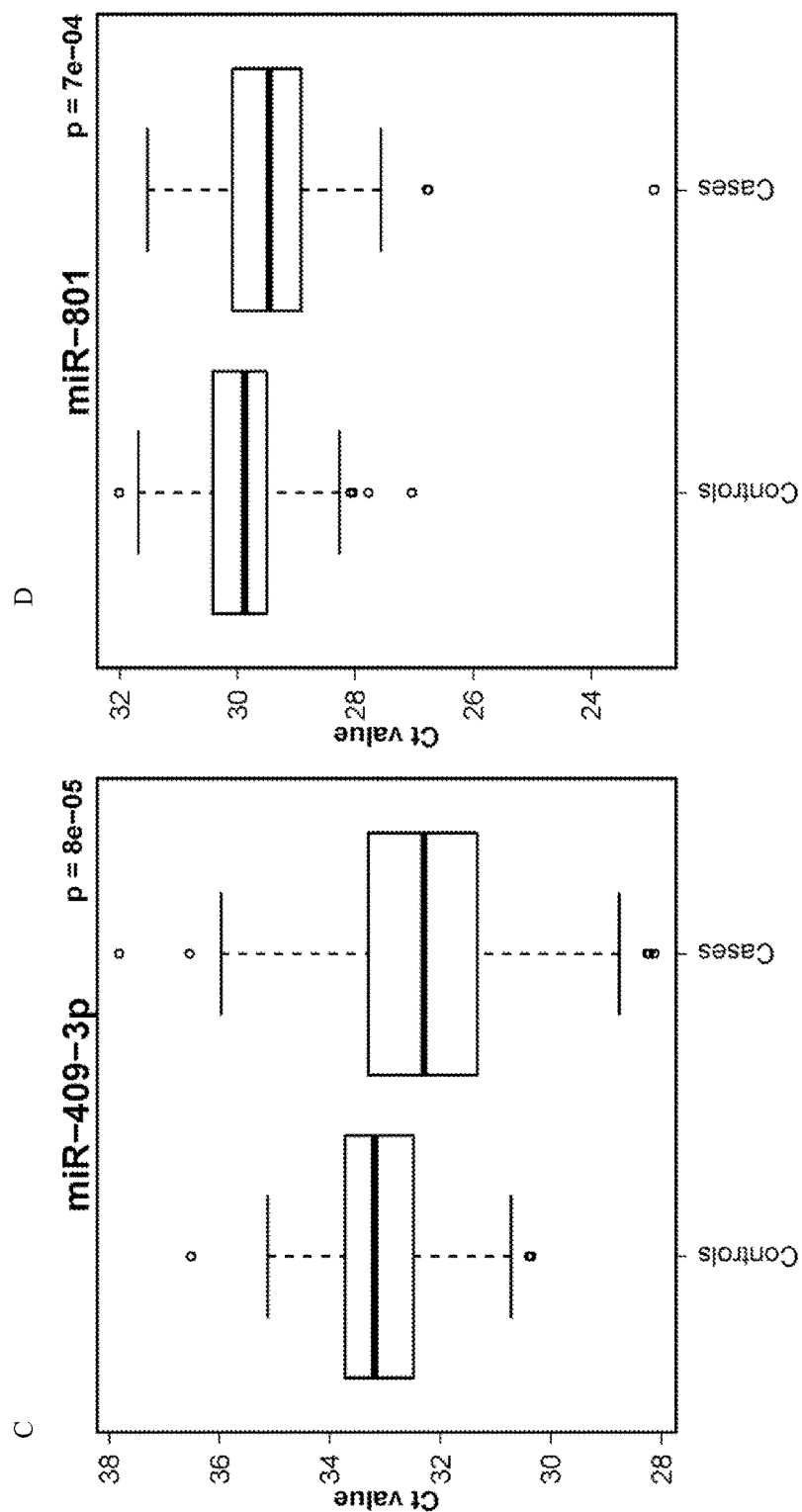
Fig. 1 C, D

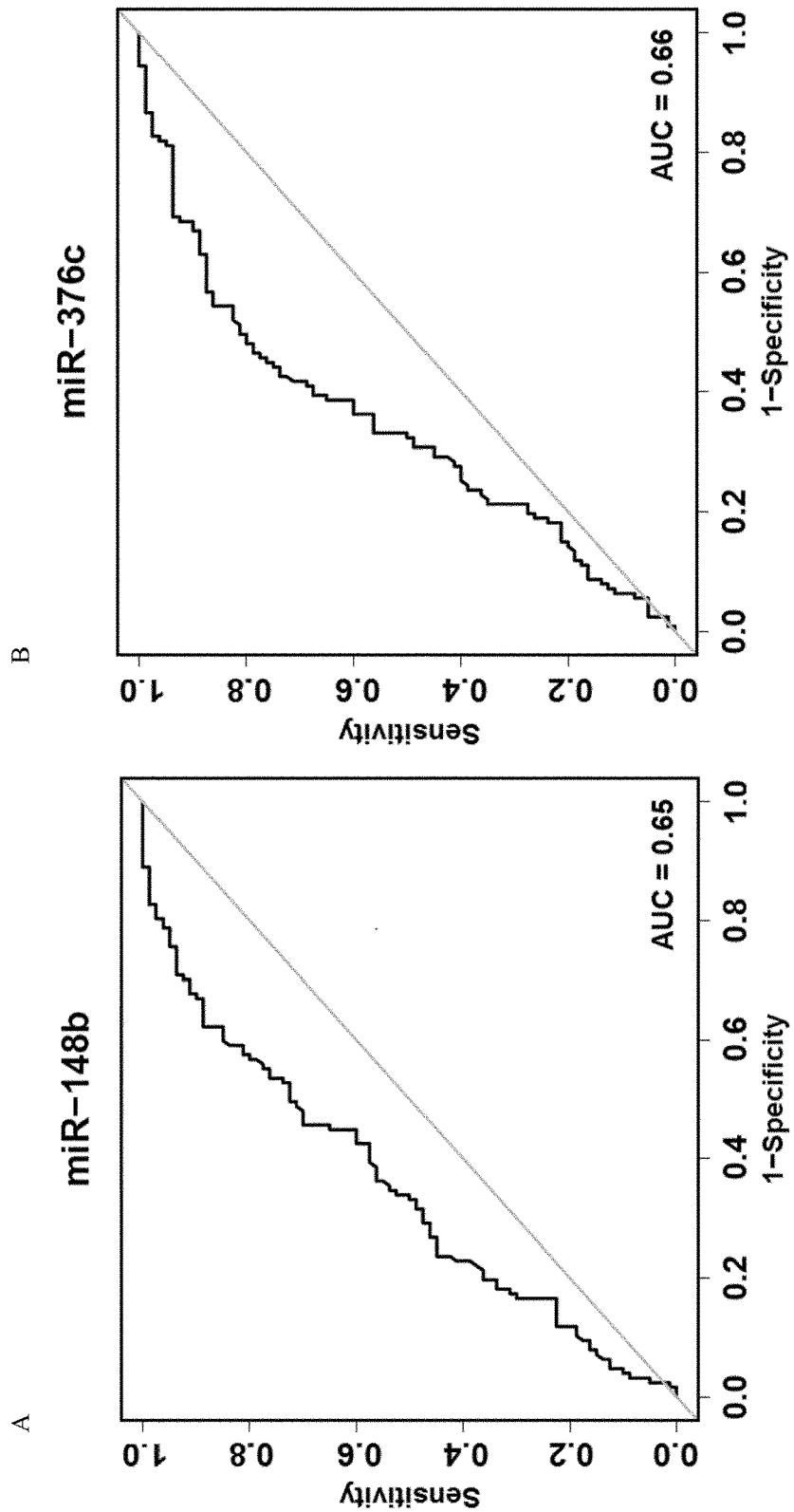
Fig. 2 A,B

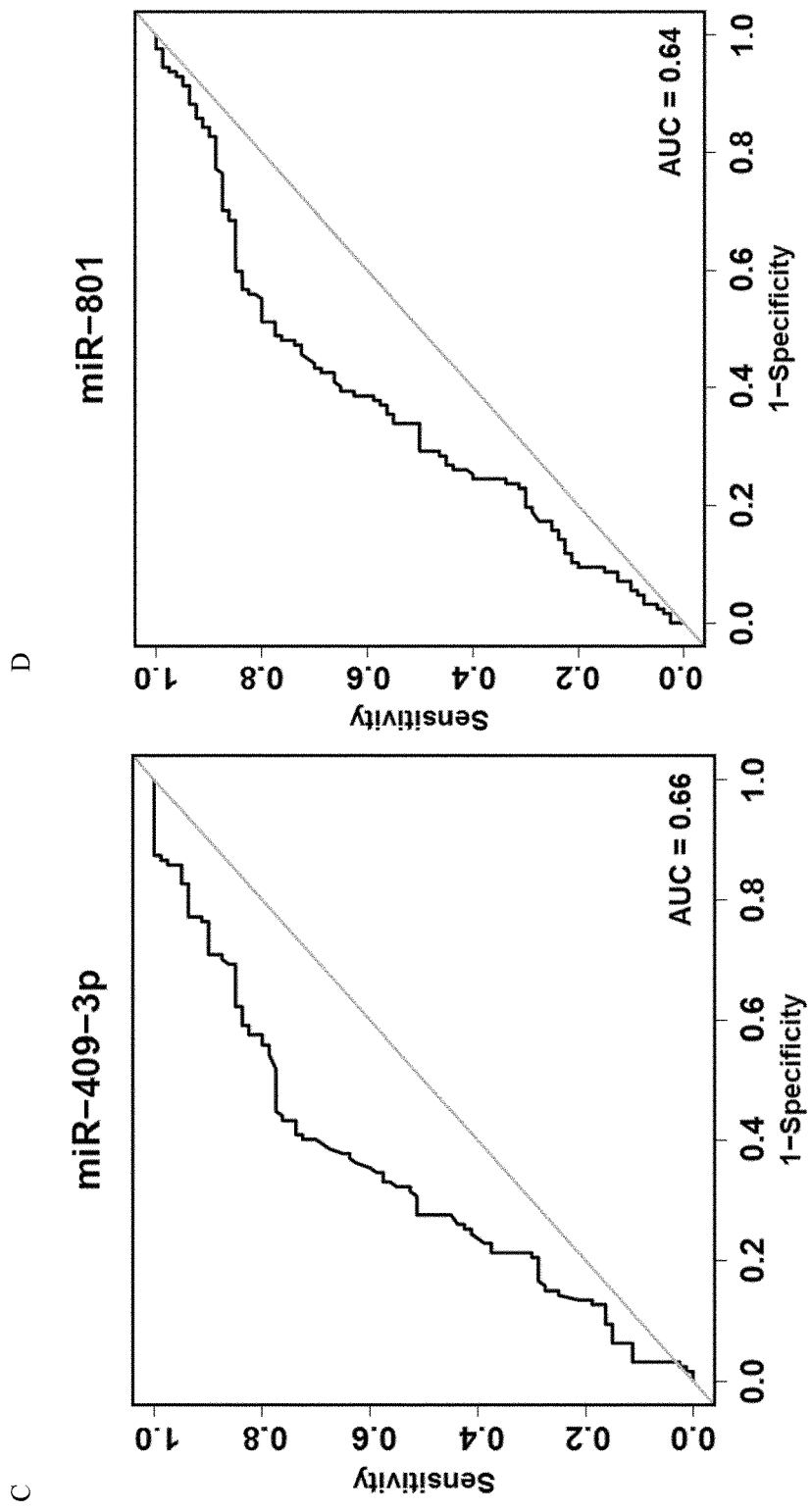
Fig. 2 C, D

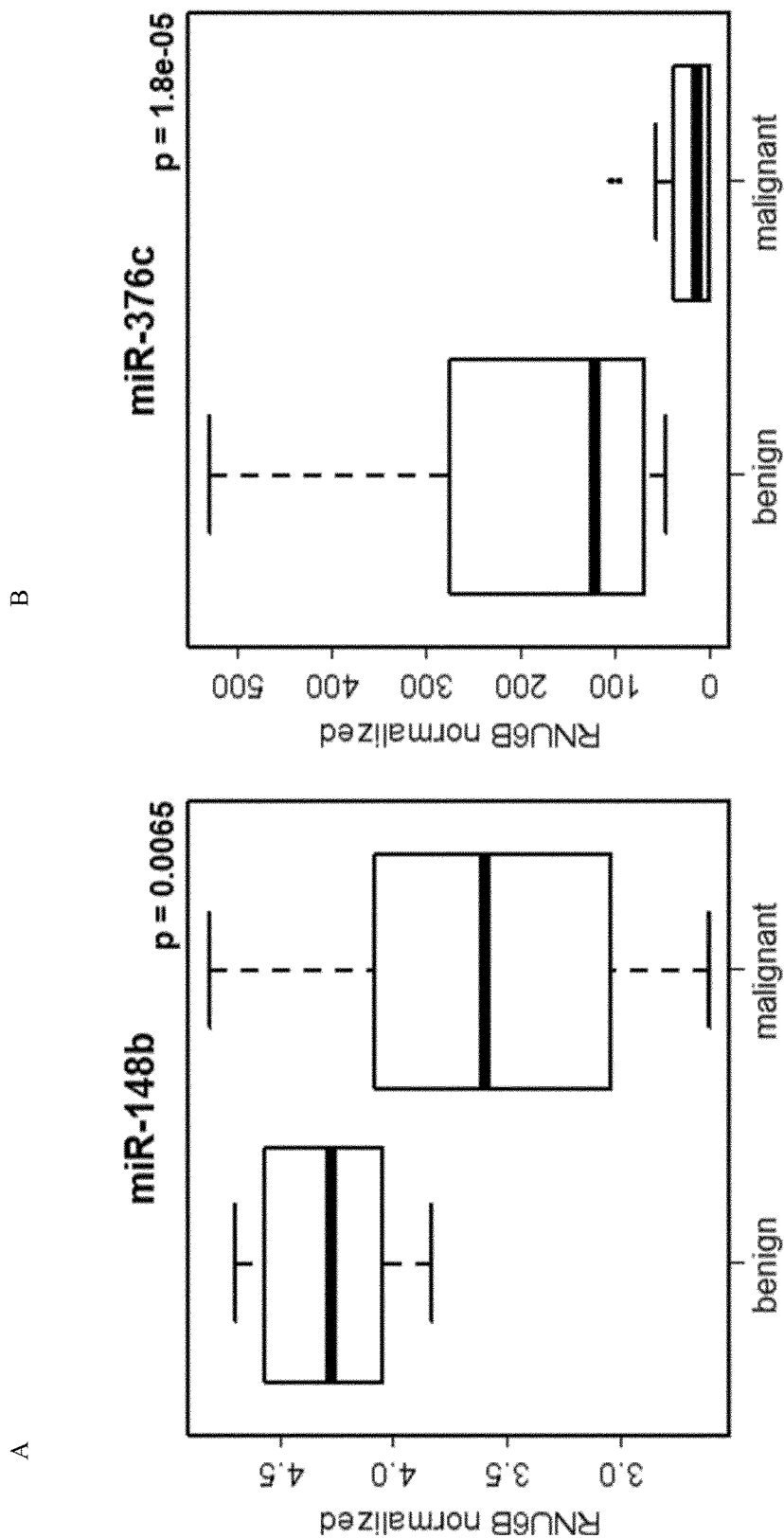
Fig. 3 A, B

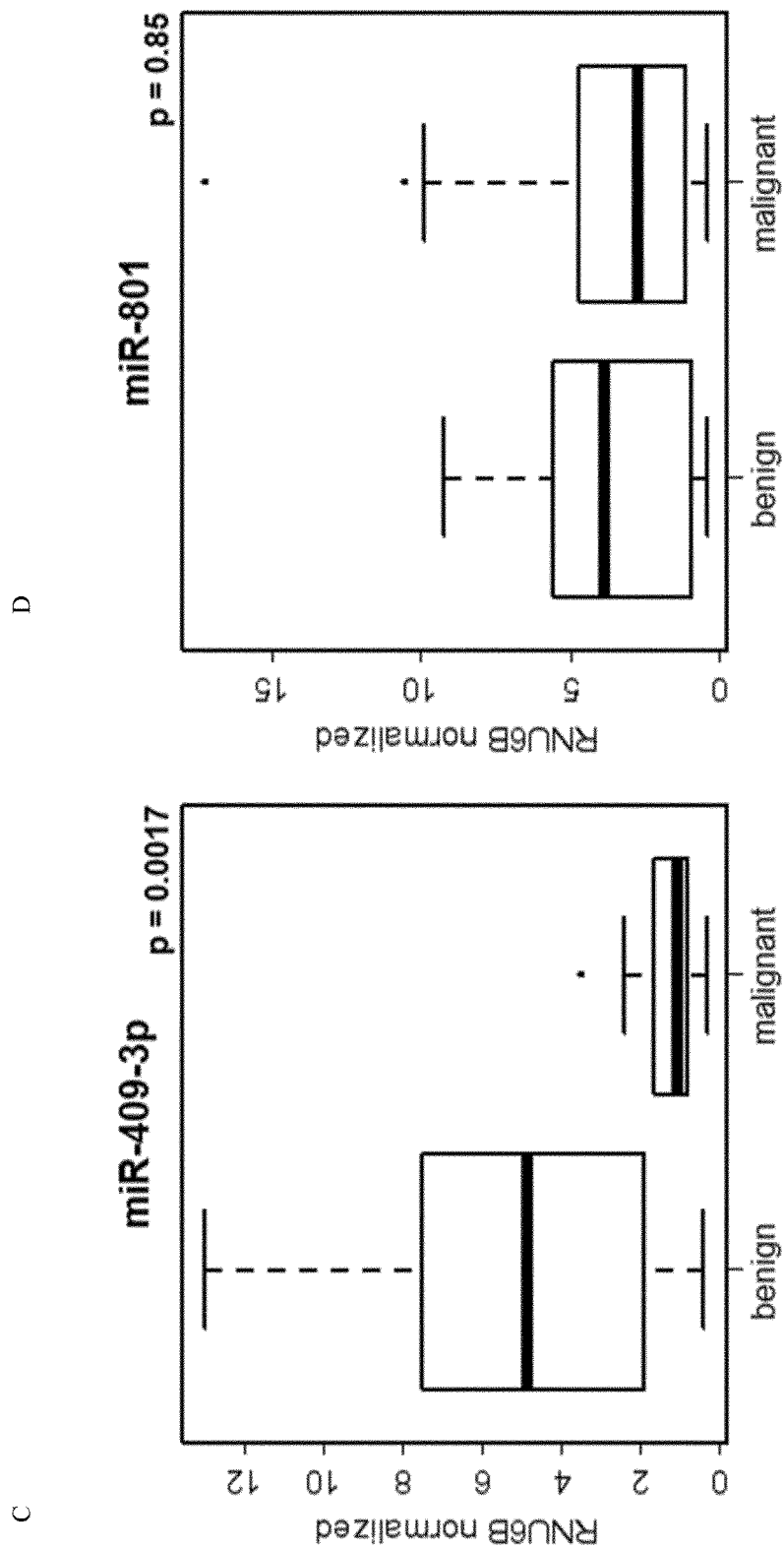
Fig. 3 C, D

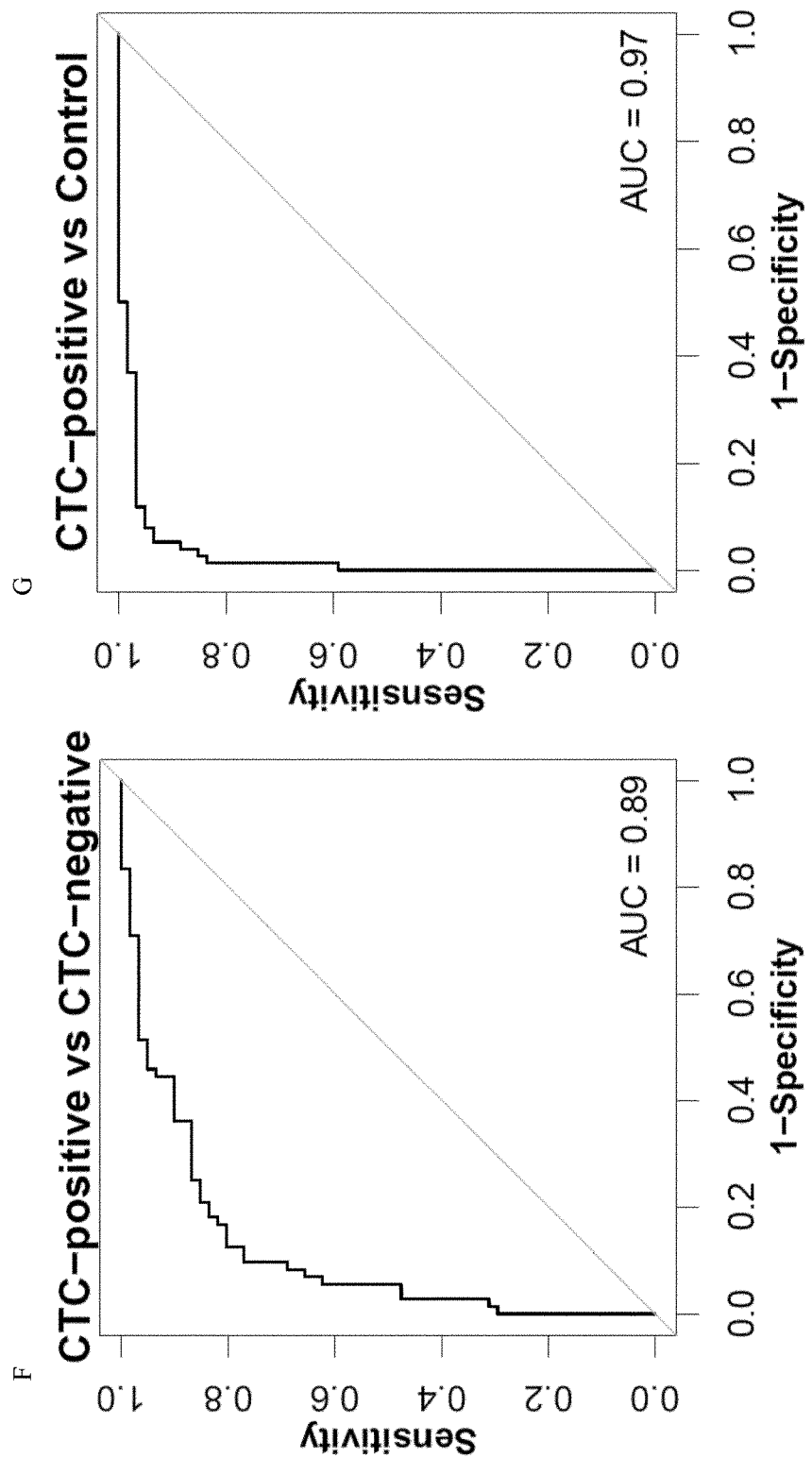
Fig. 5F,G

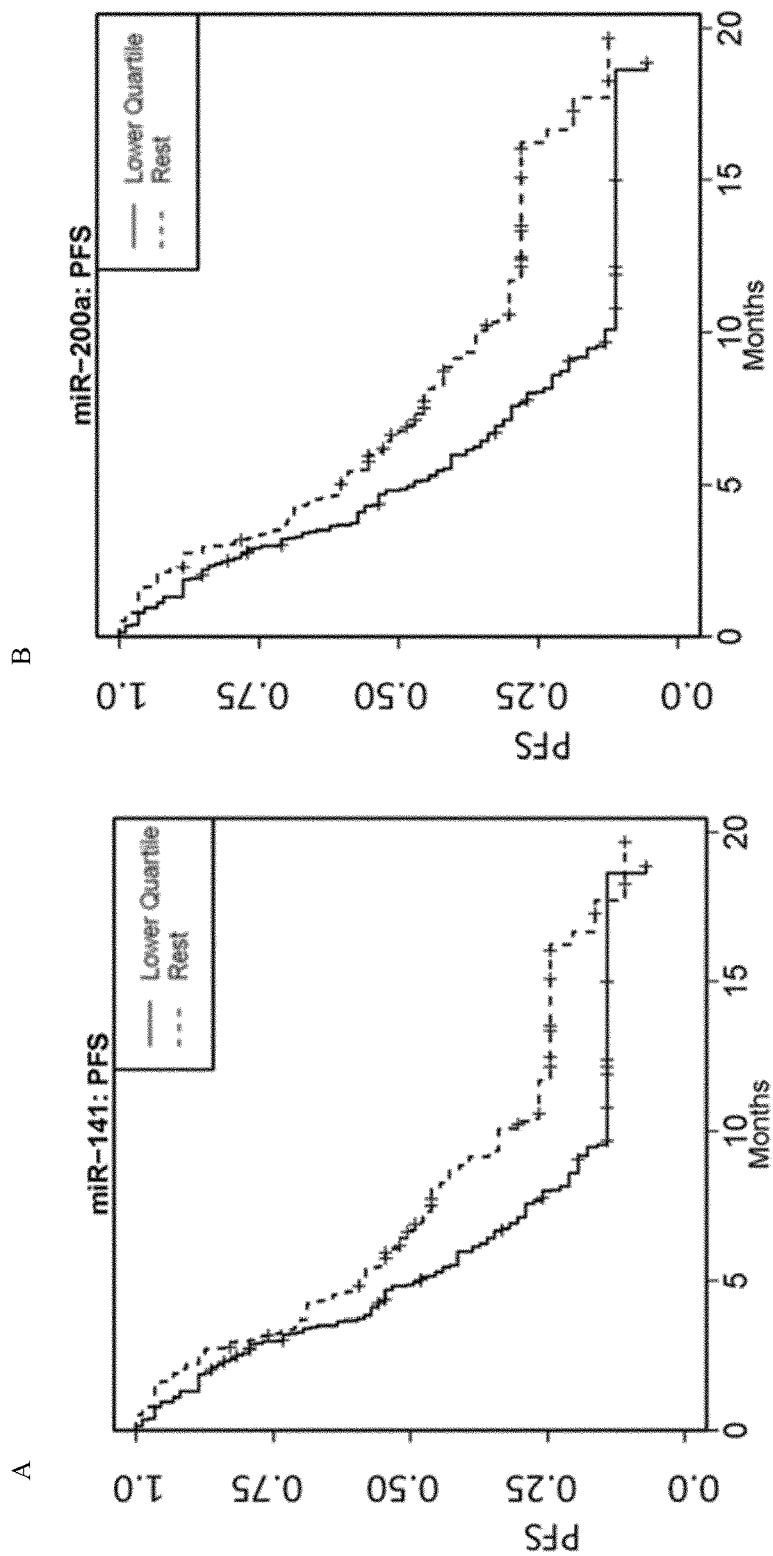
Fig. 6 A, B

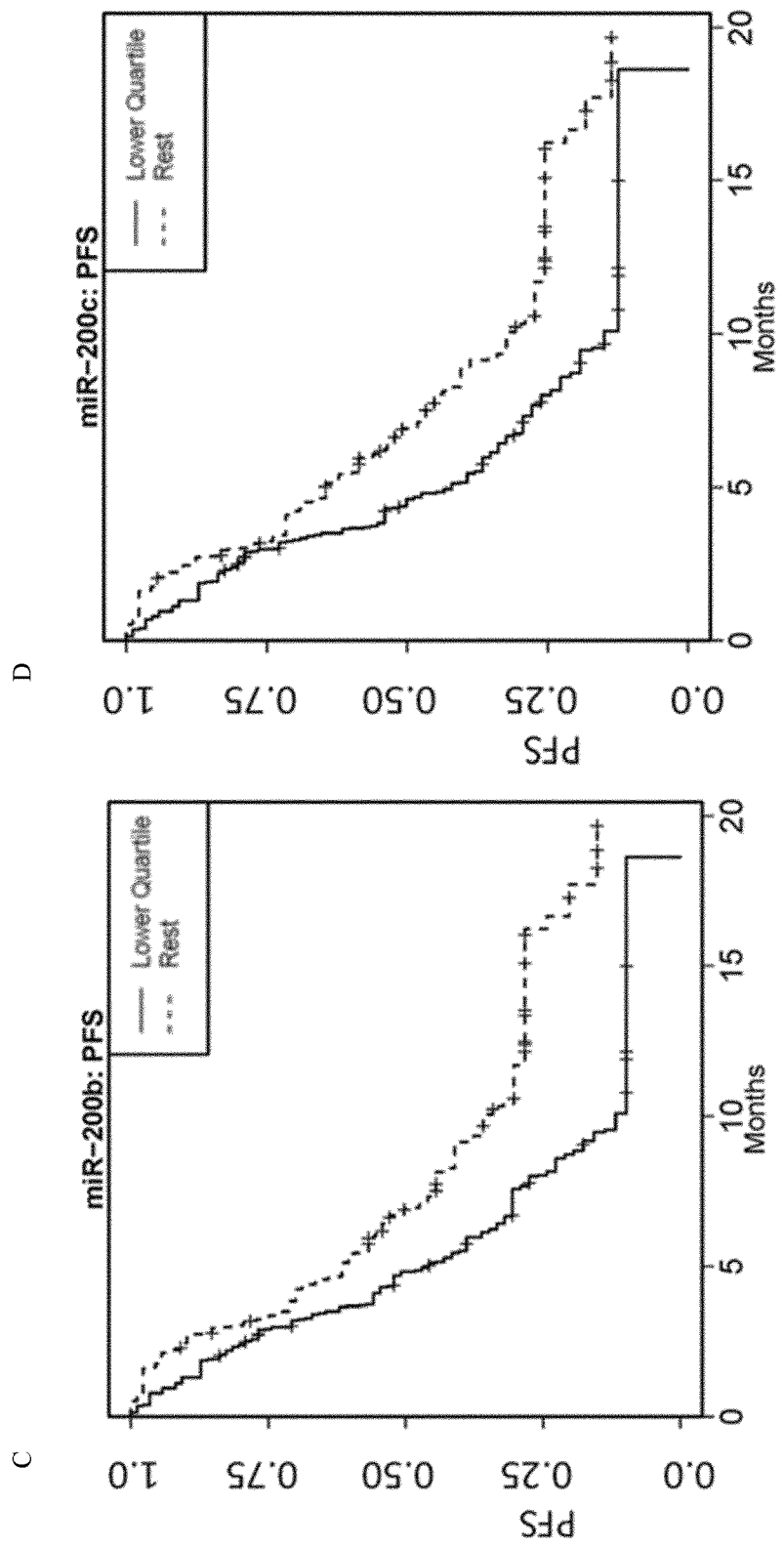
Fig. 6 C, D

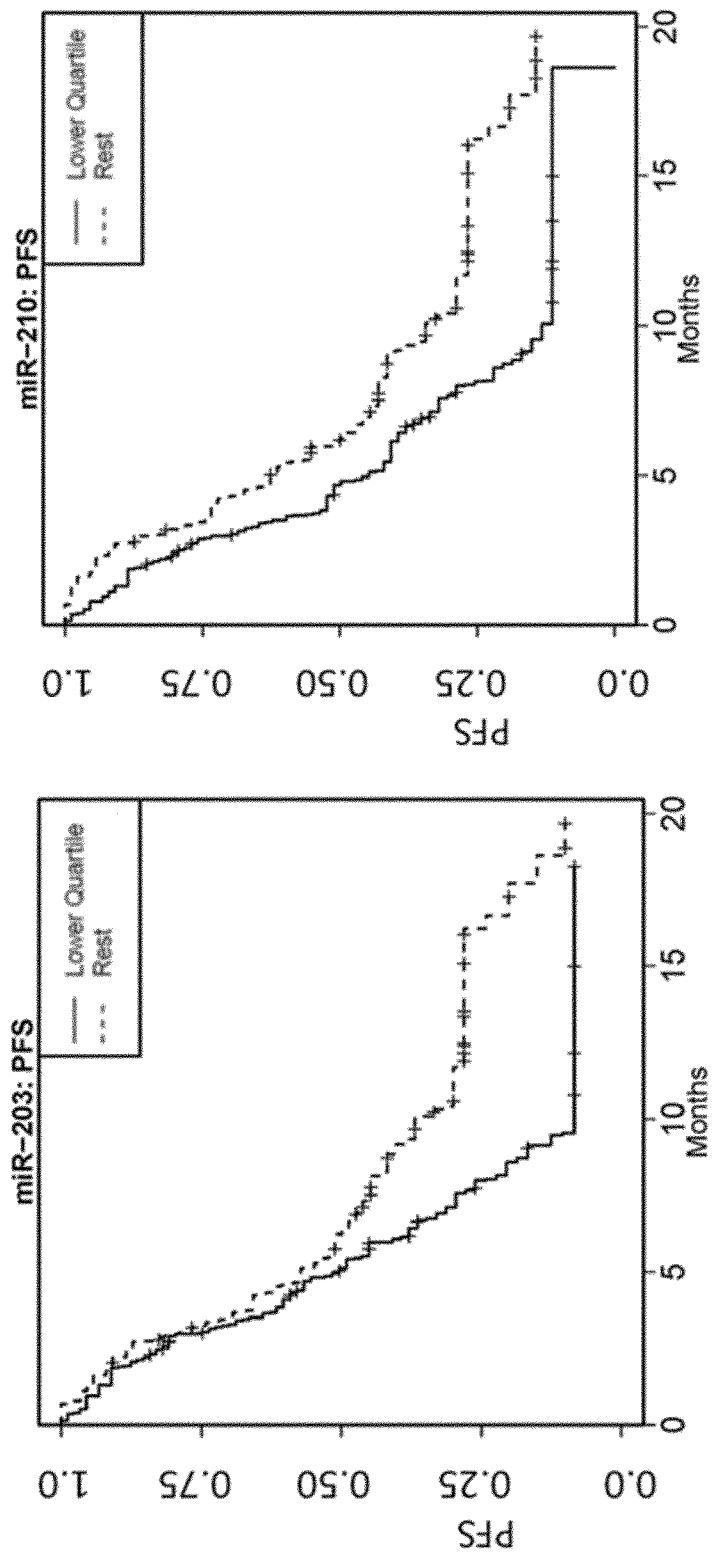
Fig. 6 E, F

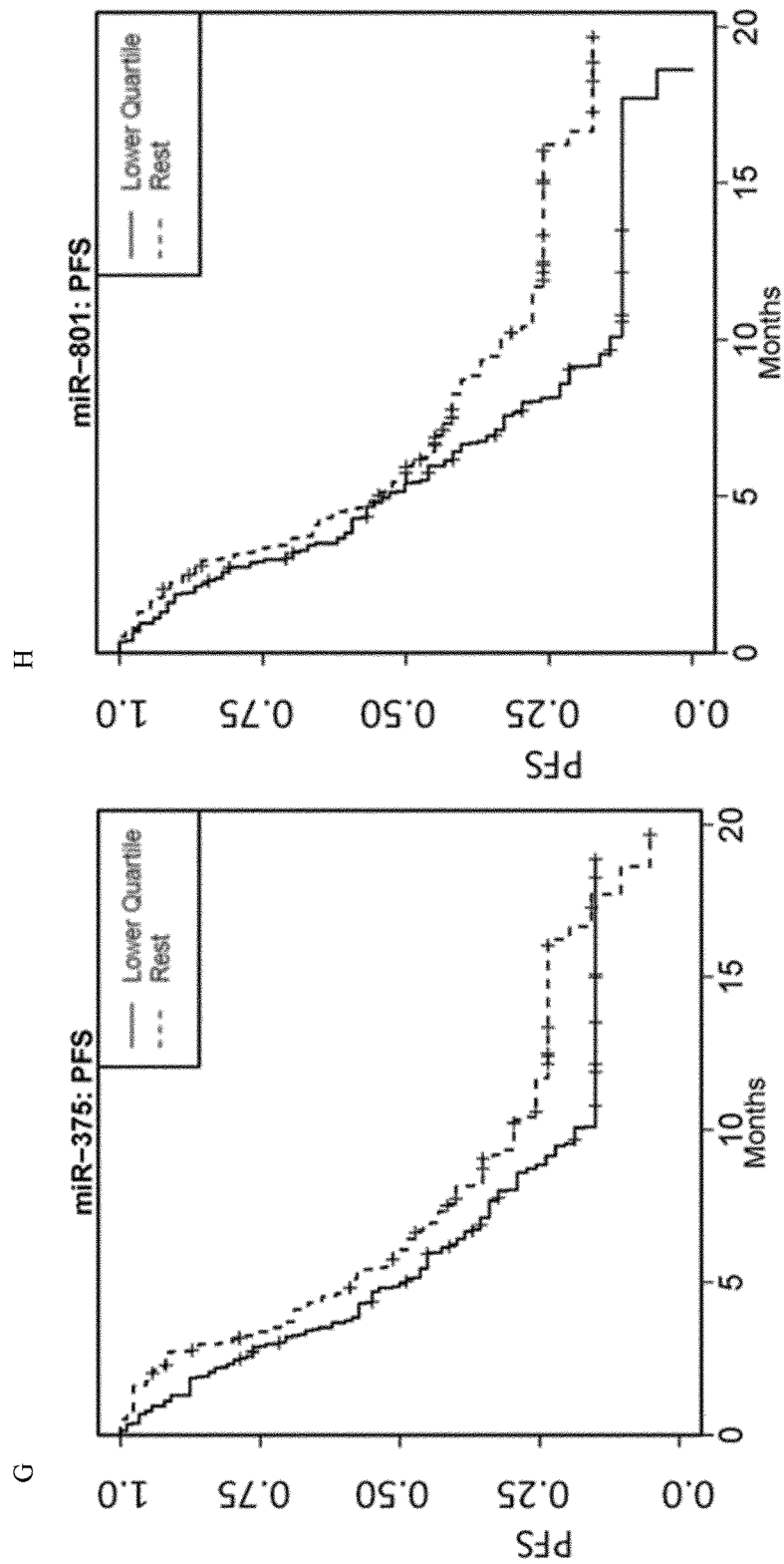
Fig 6 G, H

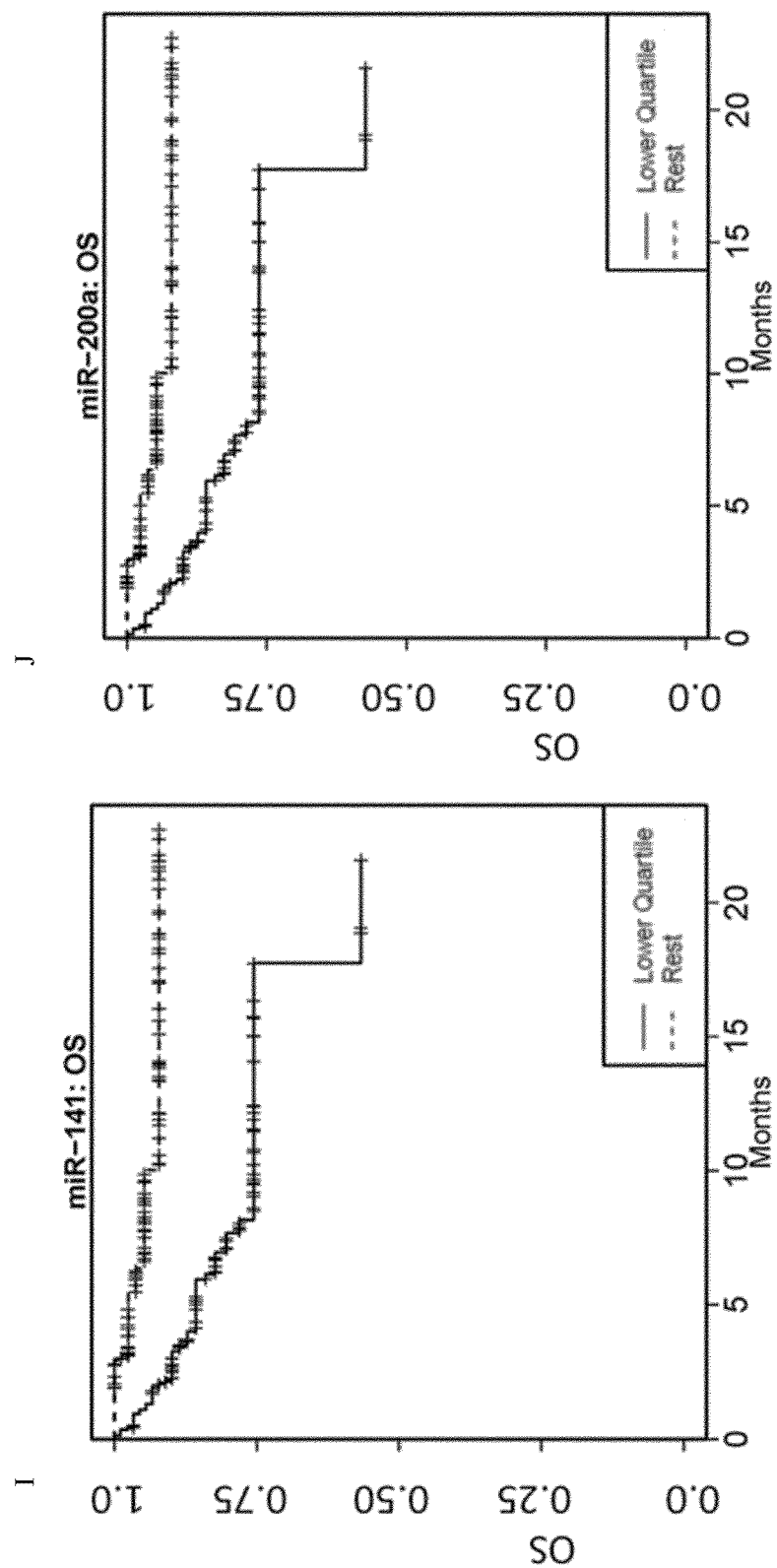
Fig. 6 I, J

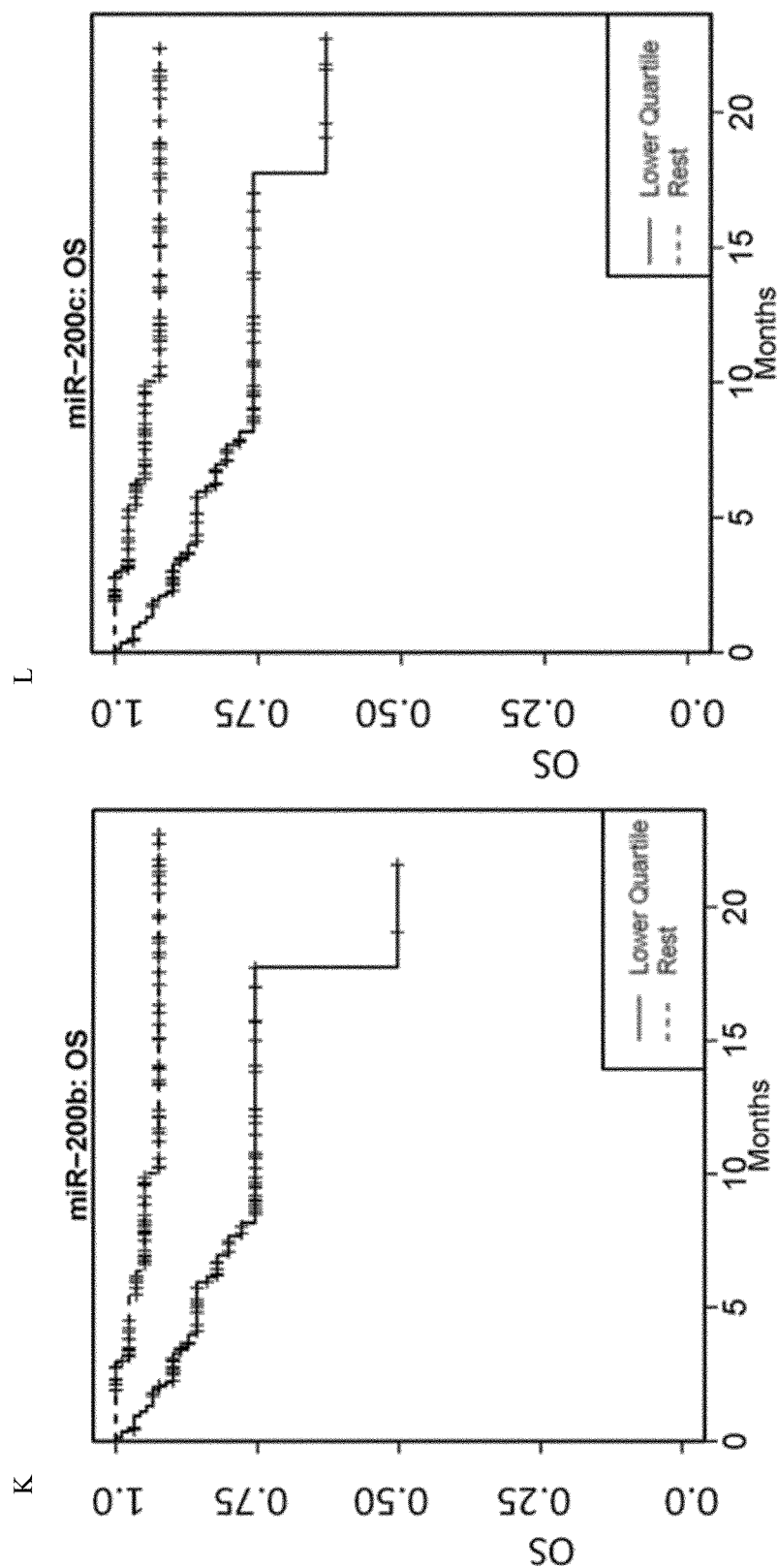
Fig. 6 K, L

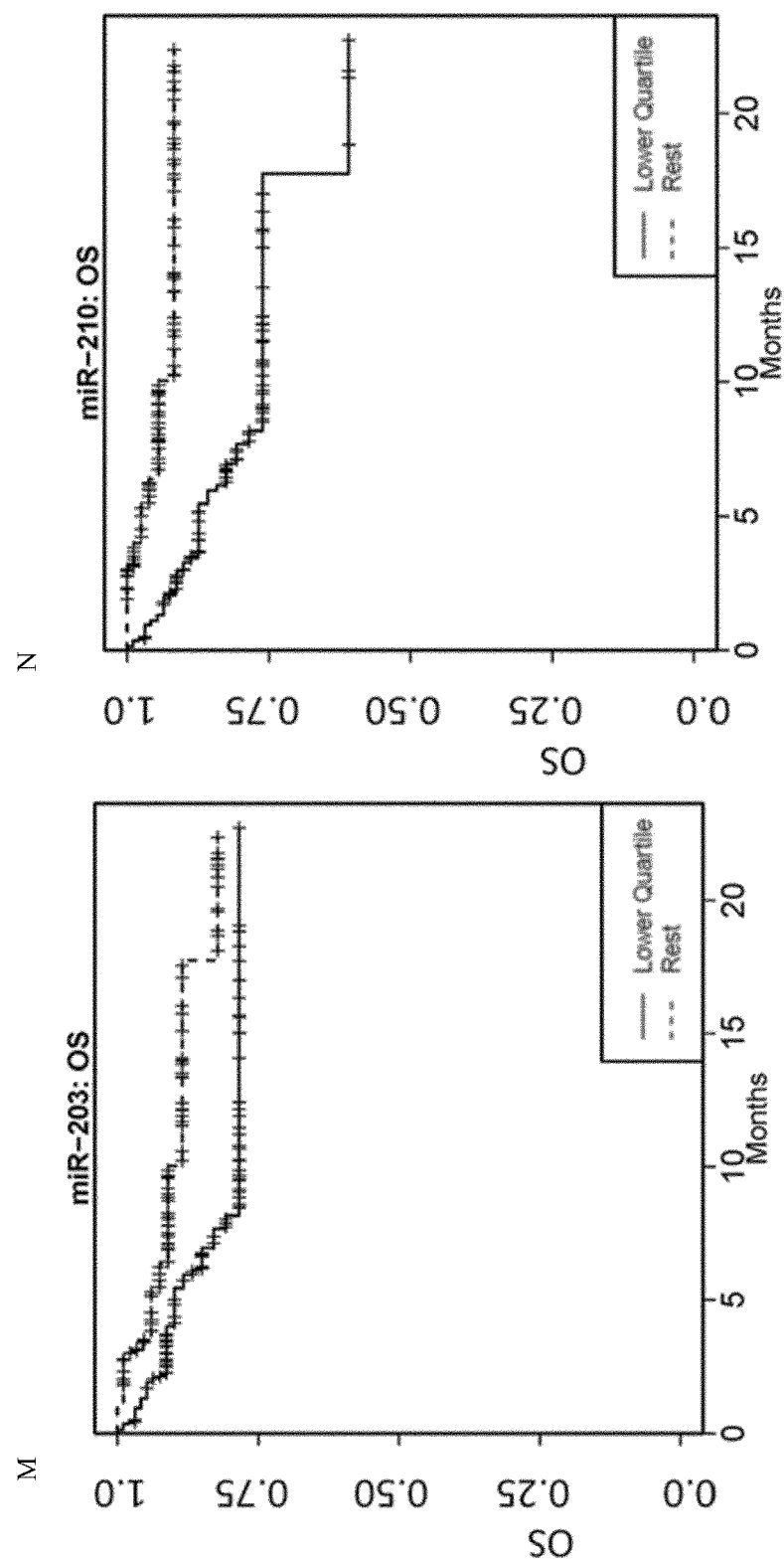
Fig. 6 M, N

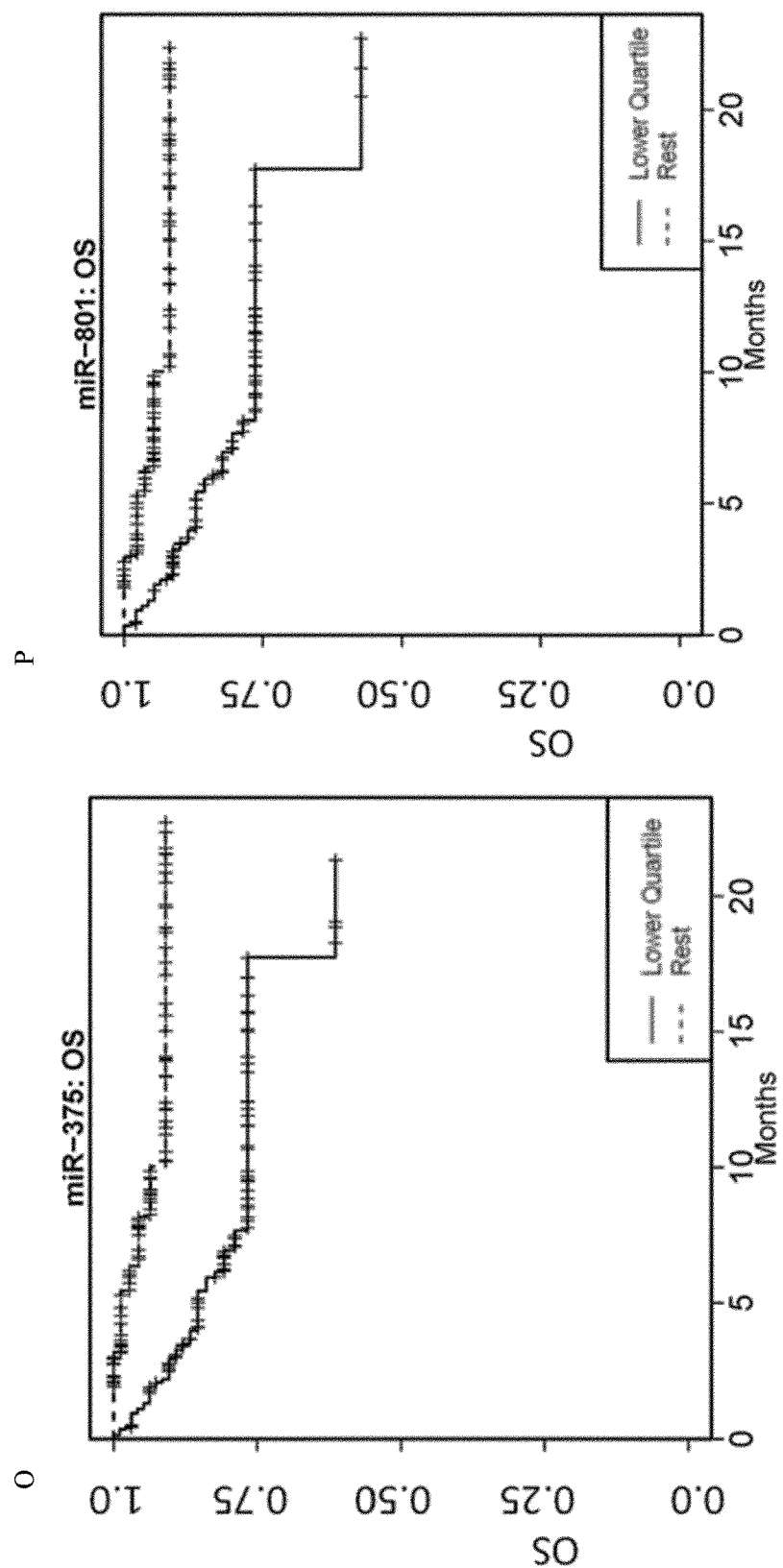
Fig. 6 O, P

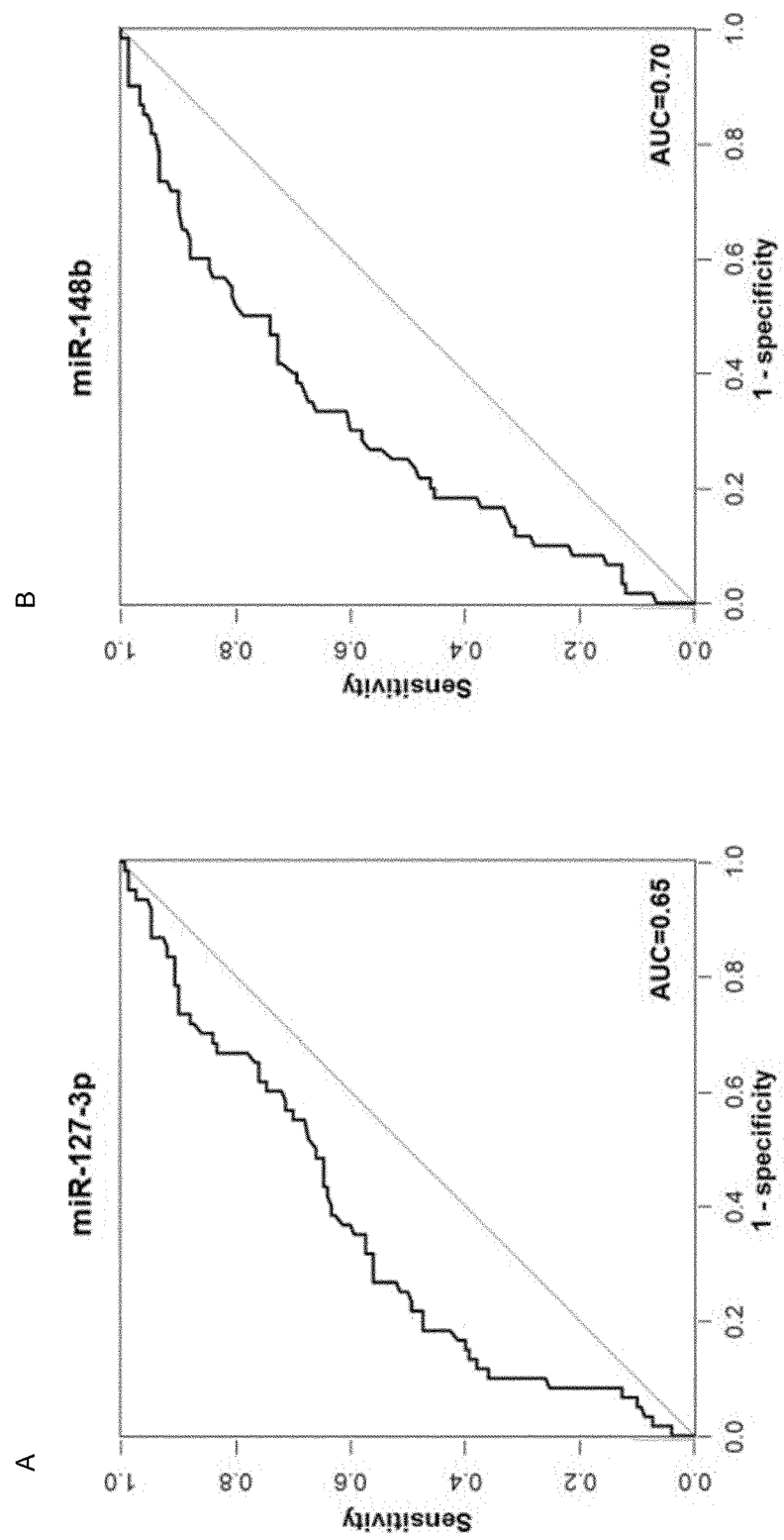
Fig. 8 A, B

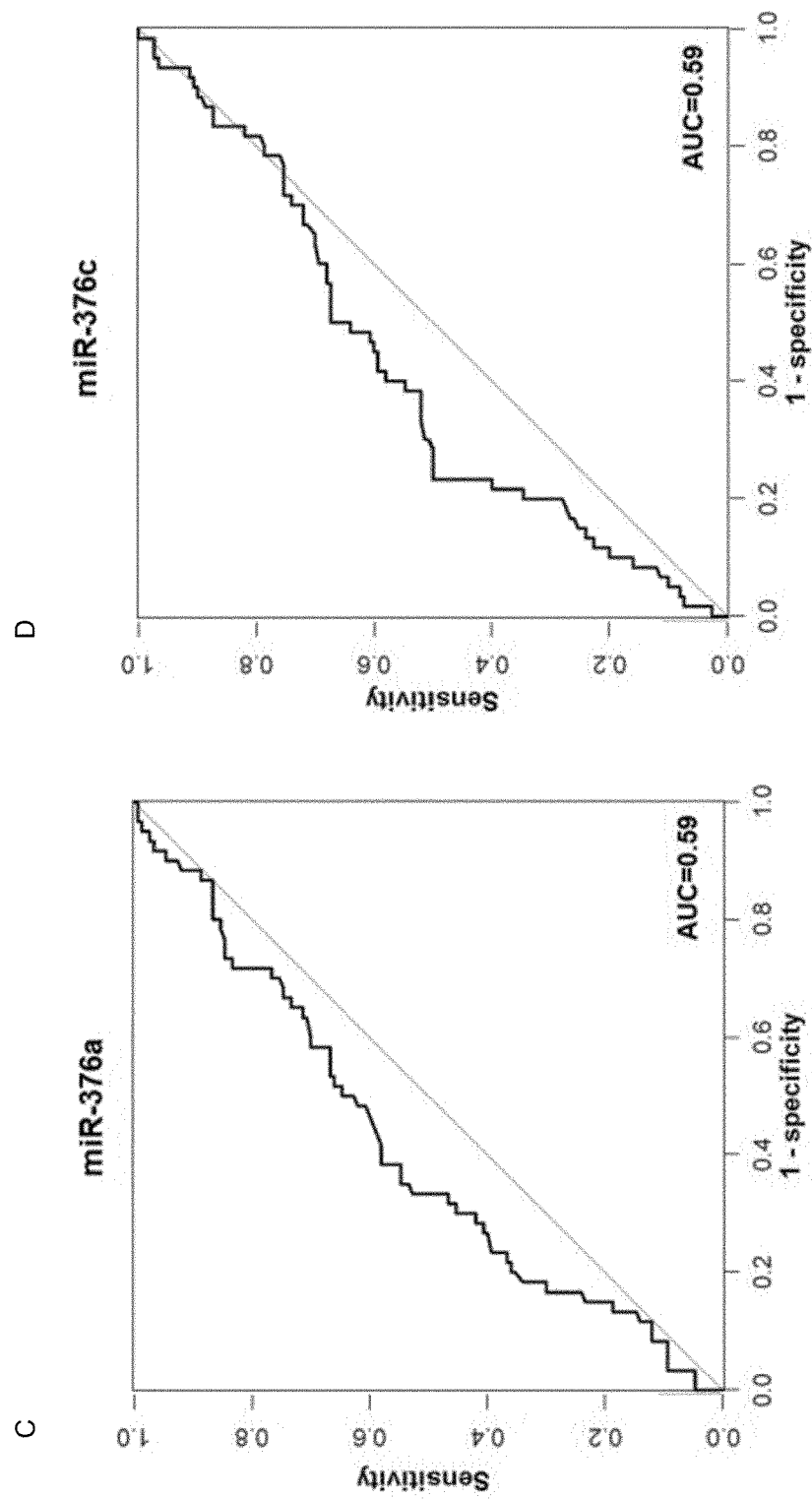
Fig. 8 C, D

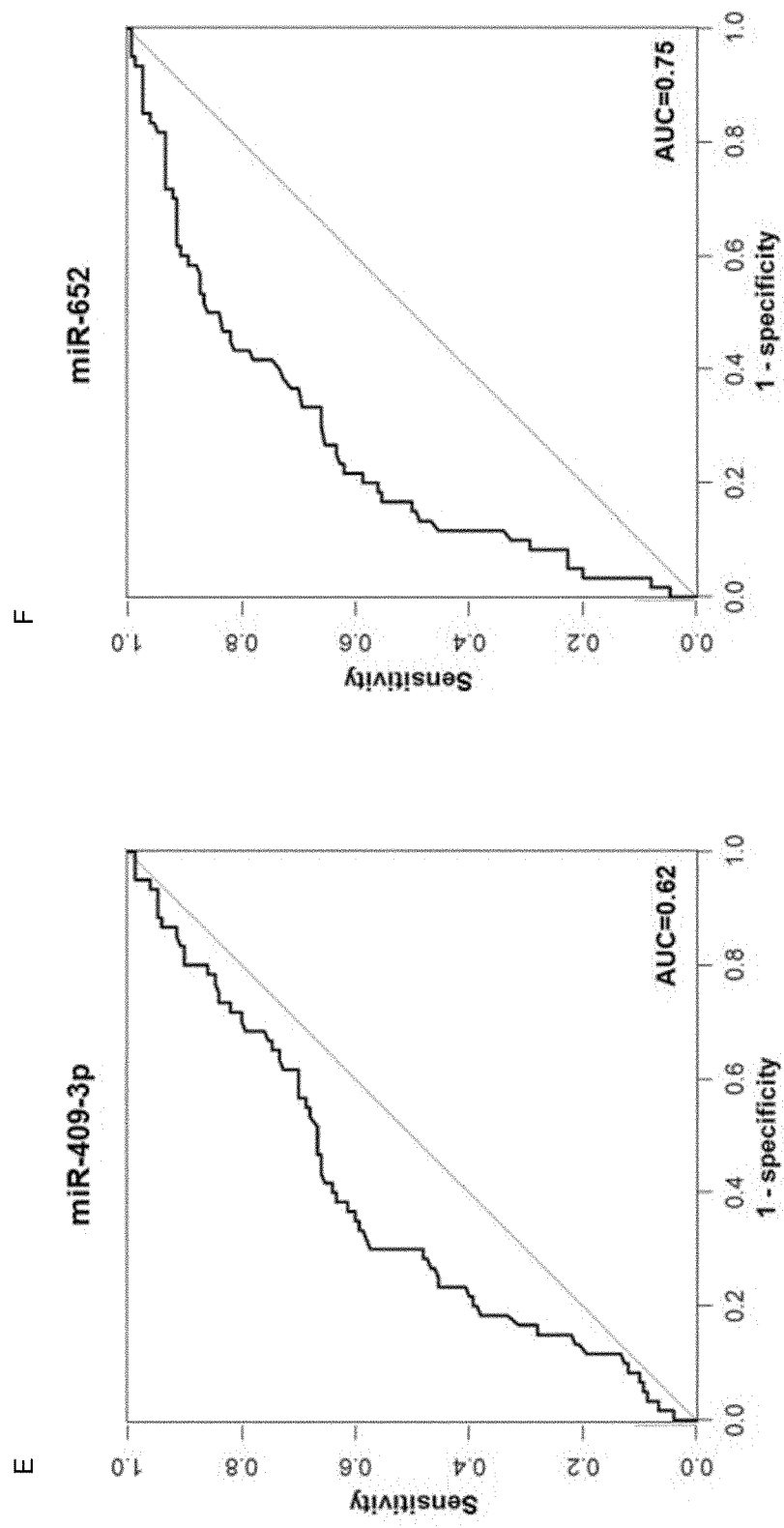
Fig. 8 E, F

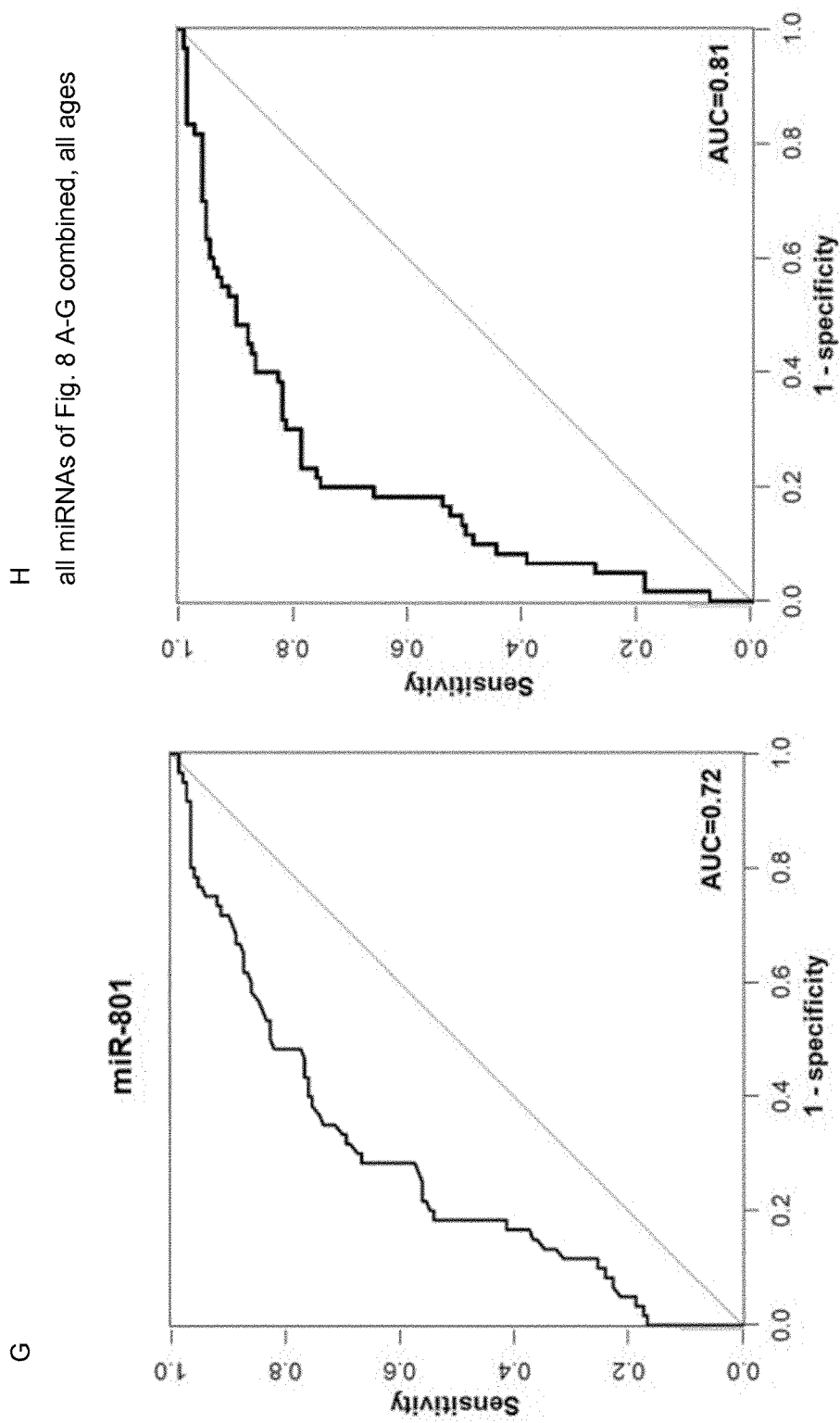
Fig. 8 G, H

Fig. 9 A - C

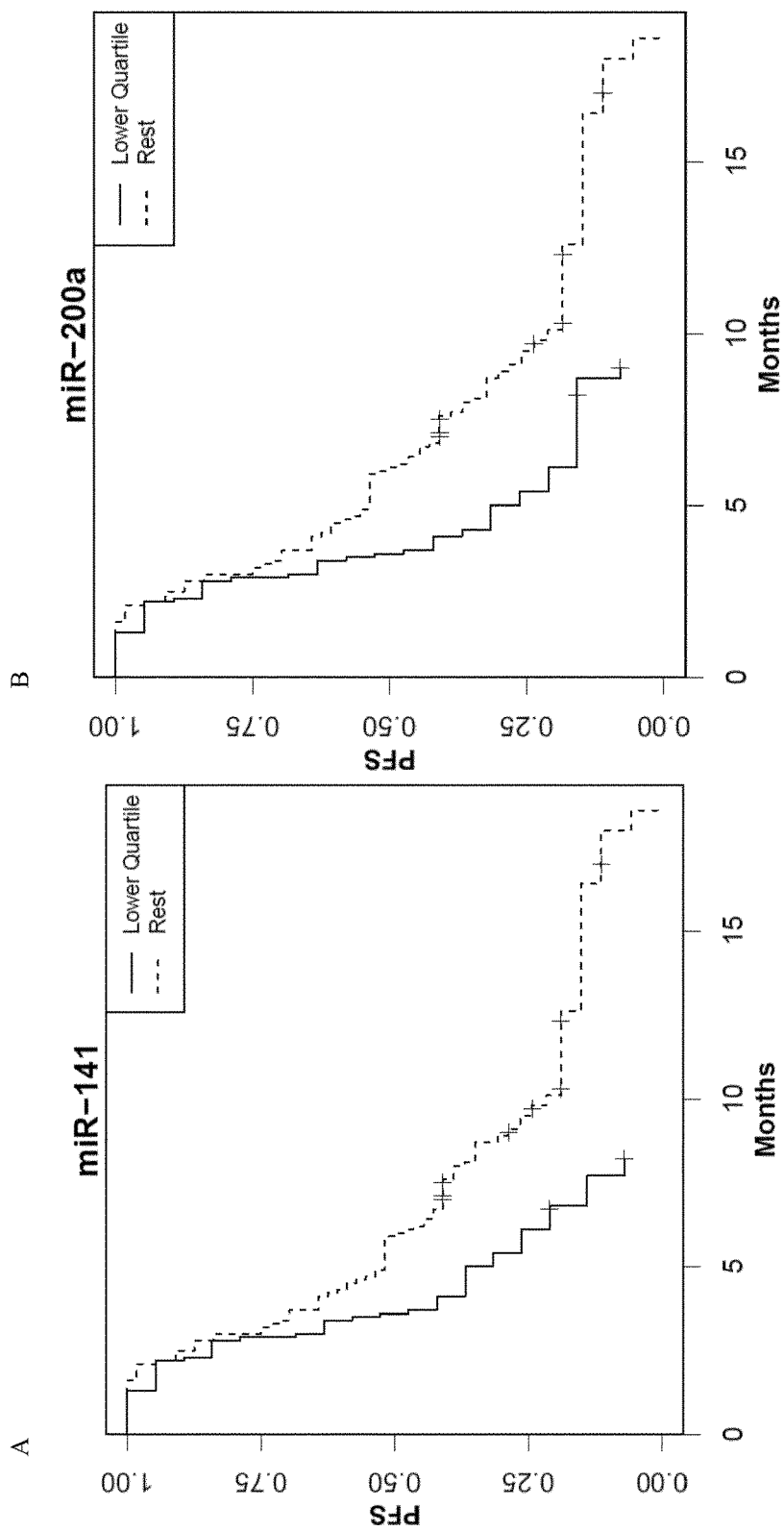
Fig. 11 A, B

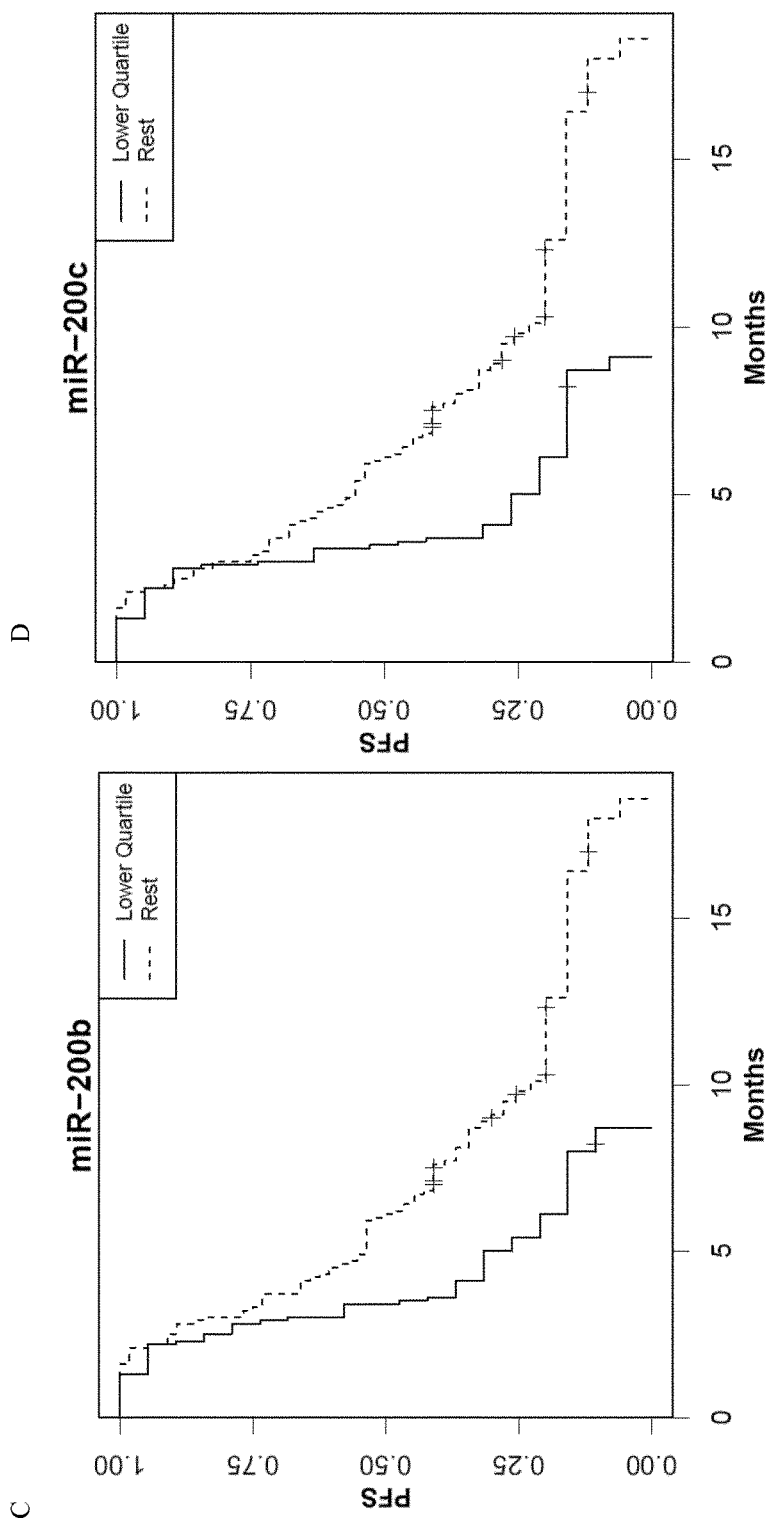
Fig. 11 C, D

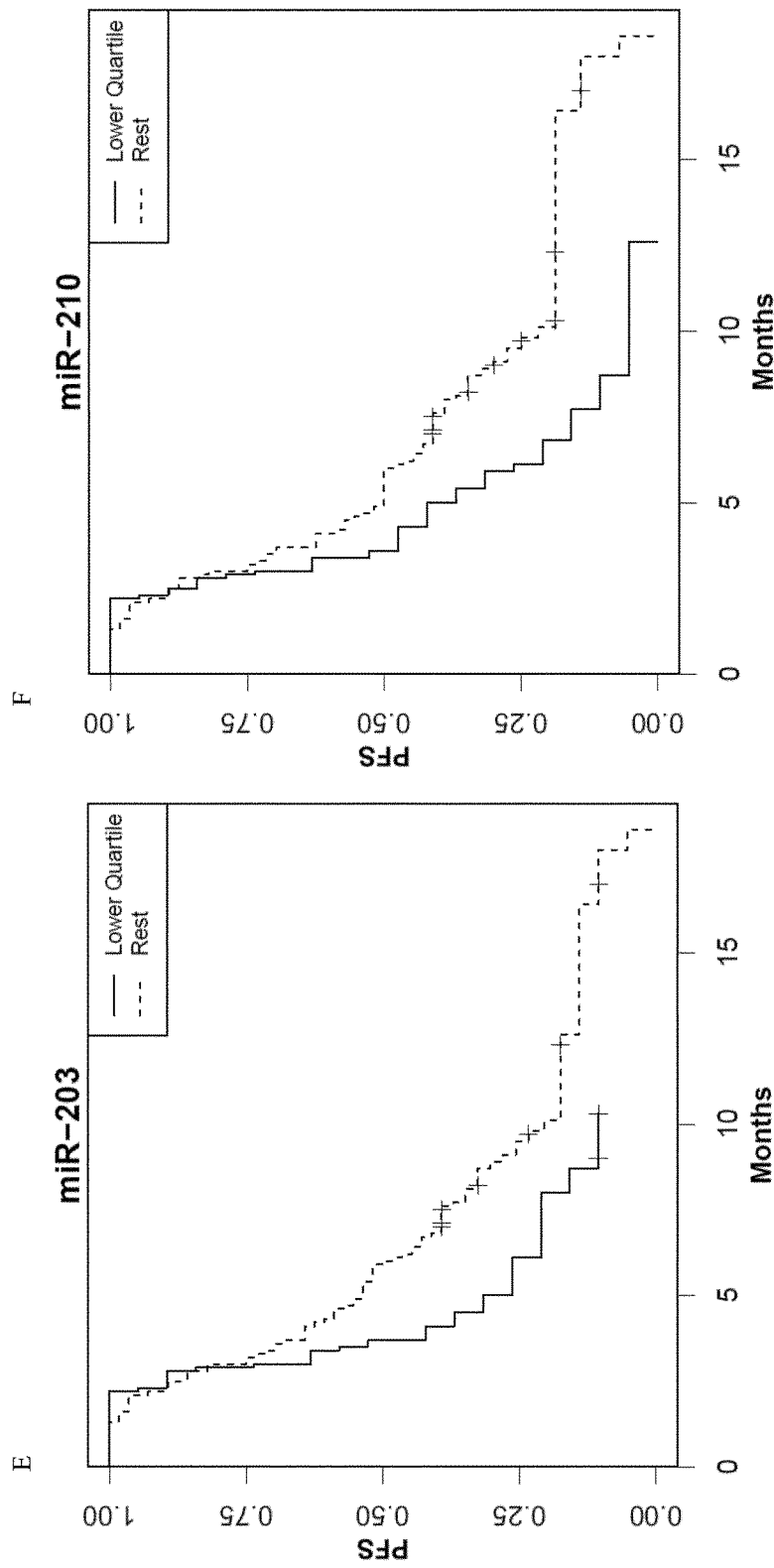
Fig. 11 E, F

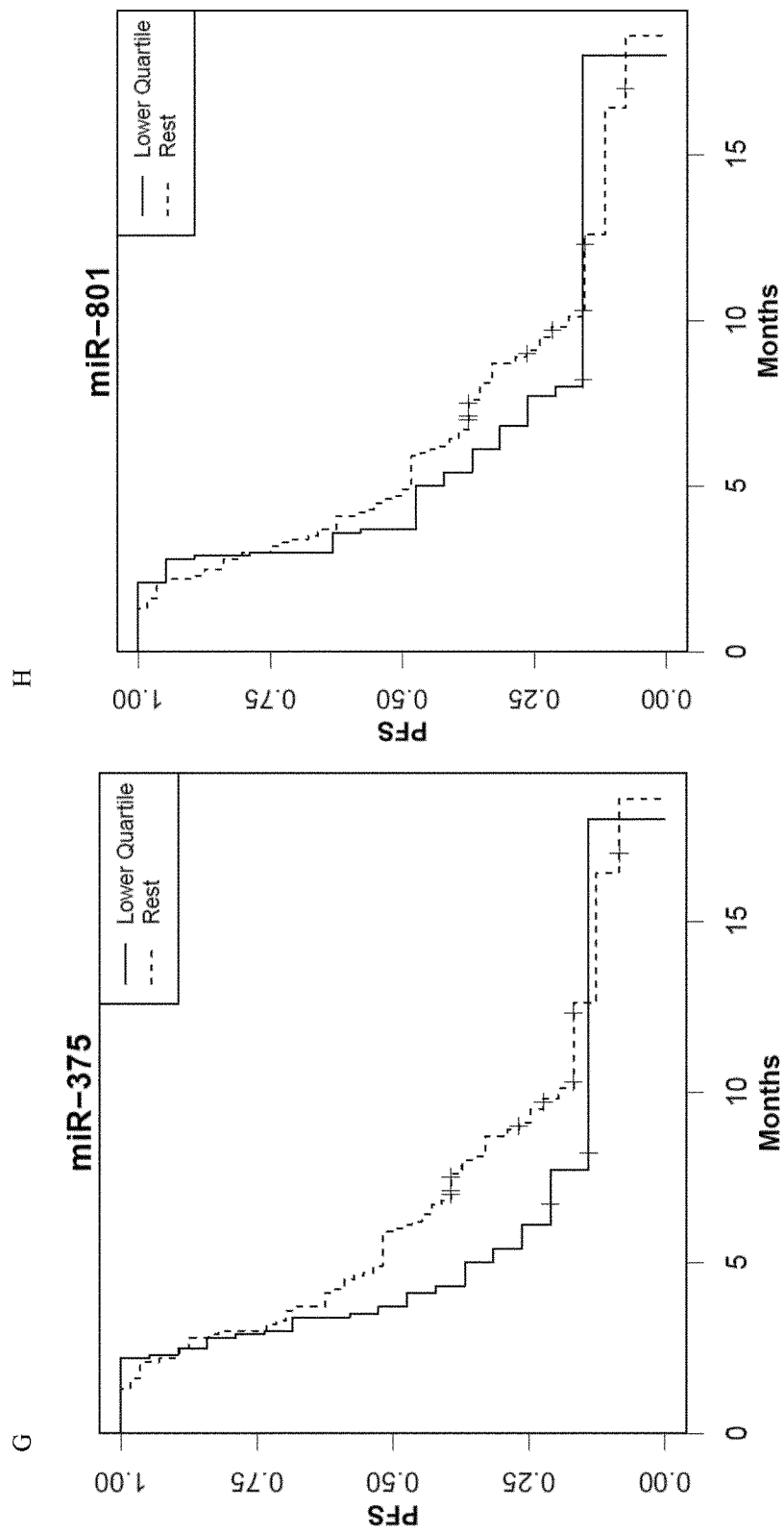
Fig. 11 G, H

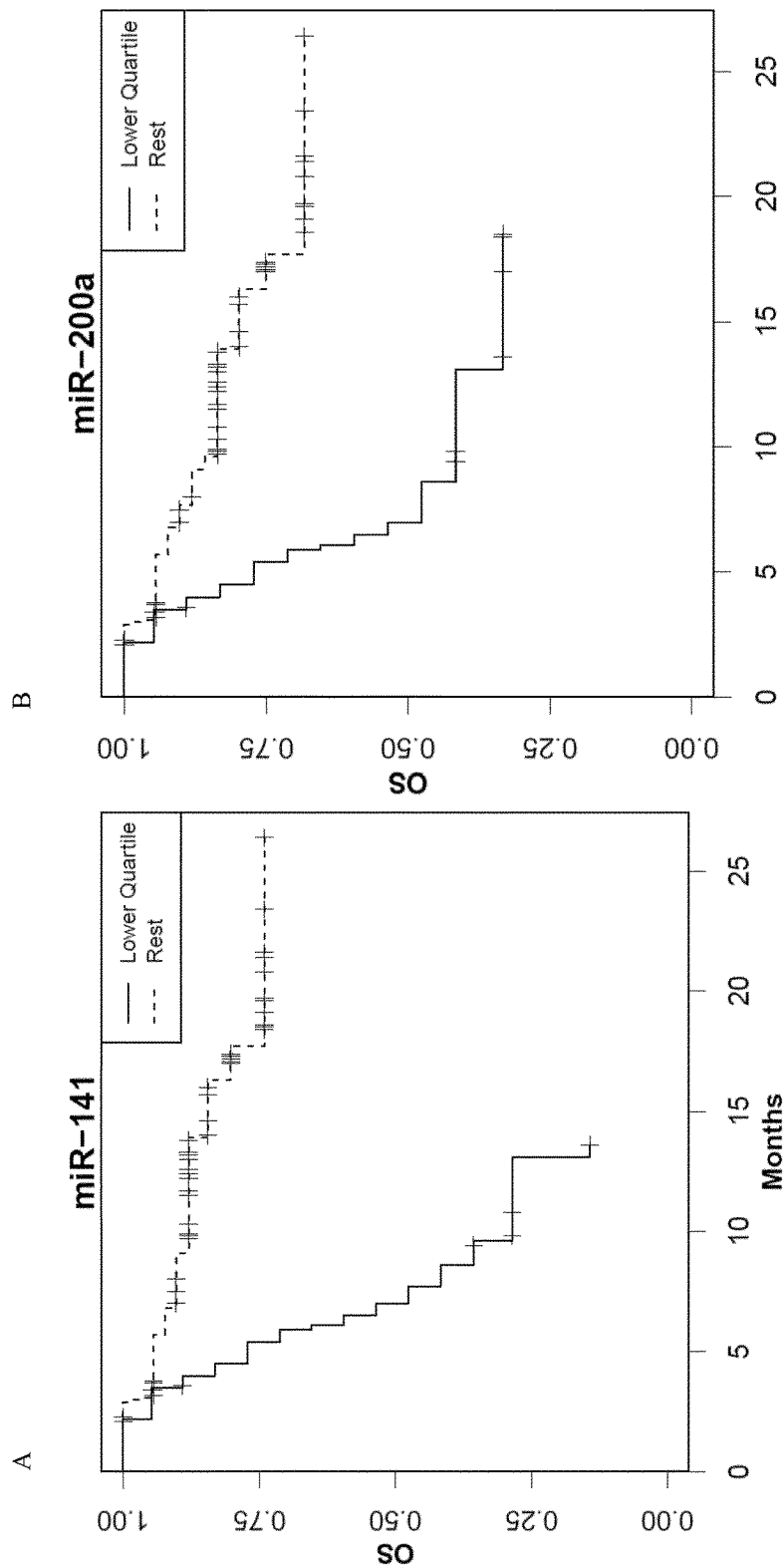
Fig. 12 A, B

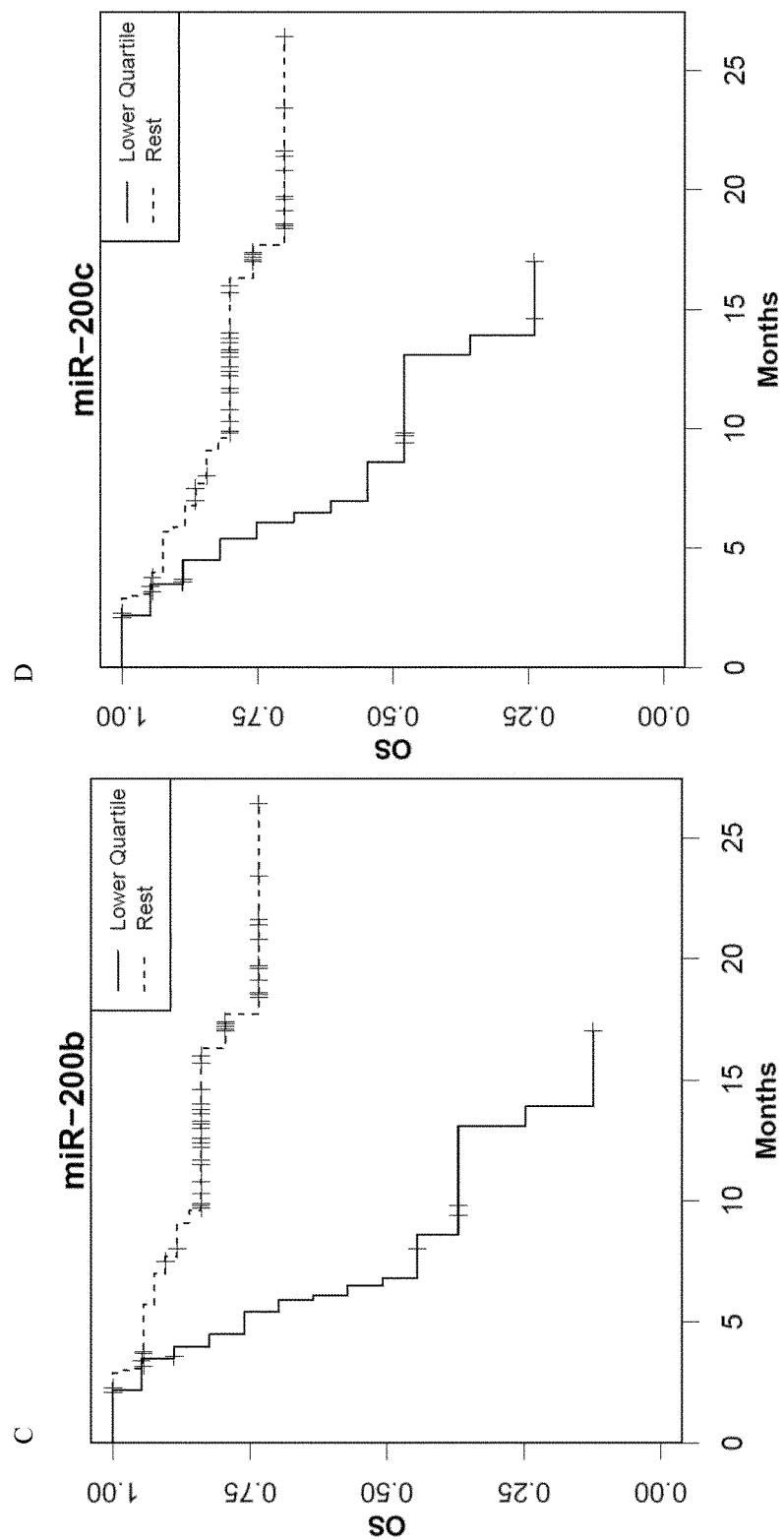
Fig. 12 C, D

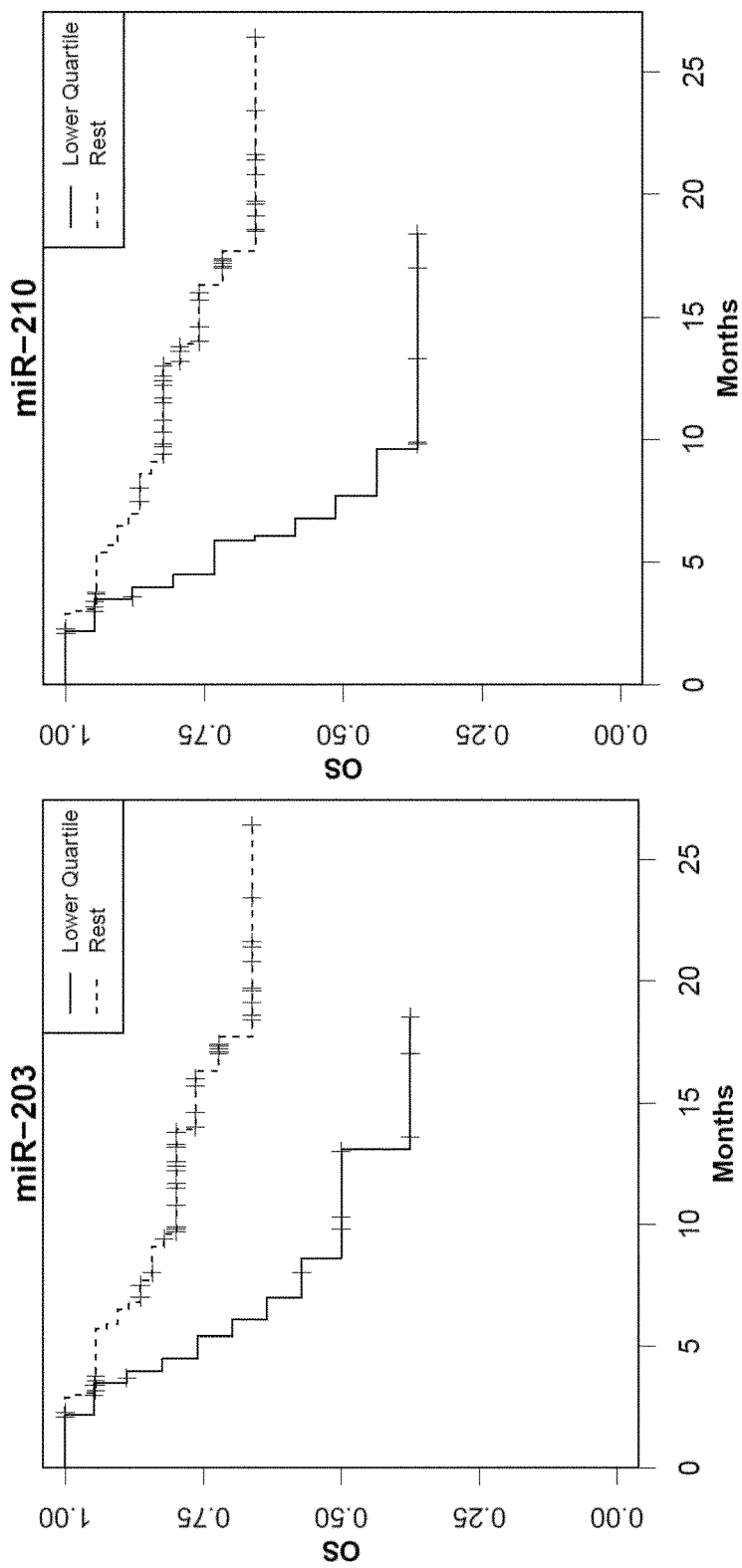
Fig. 12 E, F

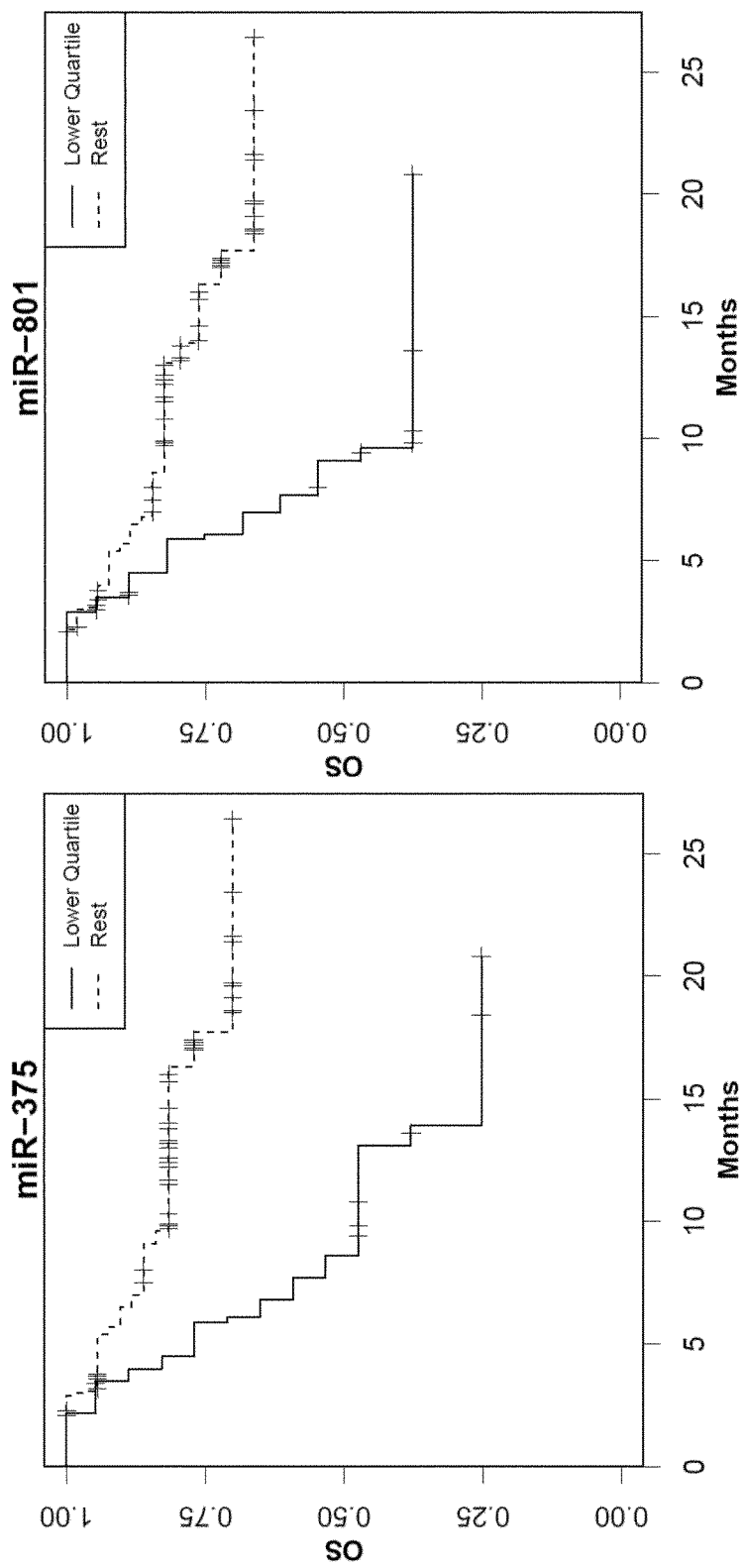
Fig. 12 G, H

SEQUENCE LISTING

<160> NUMBER OF SEQ ID NOS: 28

<210> SEQ ID NO 1
<211> LENGTH: 24
<212> TYPE: RNA
<213> ORGANISM: Homo sapiens

<400> SEQUENCE: 1
gauugcucug cgugcggaau cgac              24

```
<210> SEQ ID NO 2
<211> LENGTH: 22
<212> TYPE: RNA
<213> ORGANISM: Homo sapiens

<400> SEQUENCE: 2
ucagugcauc acagaacuuu gu                                              22

<210> SEQ ID NO 3
<211> LENGTH: 21
<212> TYPE: RNA
<213> ORGANISM: Homo sapiens

<400> SEQUENCE: 3
aacauagagg aaauuccacg u                                               21

<210> SEQ ID NO 4
<211> LENGTH: 22
<212> TYPE: RNA
<213> ORGANISM: Homo sapiens

<400> SEQUENCE: 4
gaauguugcu cggugaaccc cu                                              22

<210> SEQ ID NO 5
<211> LENGTH: 22
<212> TYPE: RNA
<213> ORGANISM: Homo sapiens

<400> SEQUENCE: 5
gugaaauguu uaggaccacu ag                                              22

<210> SEQ ID NO 6
<211> LENGTH: 28
<212> TYPE: RNA
<213> ORGANISM: Homo sapiens

<400> SEQUENCE: 6
ucacaaugcu gacacucaaa cugcugac                                        28

<210> SEQ ID NO 7
<211> LENGTH: 23
<212> TYPE: RNA
<213> ORGANISM: Homo sapiens

<400> SEQUENCE: 7
uguaguguuu ccuacuuuau gga                                             23

<210> SEQ ID NO 8
<211> LENGTH: 22
<212> TYPE: RNA
<213> ORGANISM: Homo sapiens

<400> SEQUENCE: 8
uaacacuguc ugguaaagau gg                                              22

<210> SEQ ID NO 9
<211> LENGTH: 22
<212> TYPE: RNA
<213> ORGANISM: Homo sapiens

<400> SEQUENCE: 9
uaauacugcc ugguaaugau ga                                              22
```

```
<210> SEQ ID NO 10
<211> LENGTH: 23
<212> TYPE: RNA
<213> ORGANISM: Homo sapiens

<400> SEQUENCE: 10
uaauacugcc ggguaaugau gga                                              23

<210> SEQ ID NO 11
<211> LENGTH: 22
<212> TYPE: RNA
<213> ORGANISM: Homo sapiens

<400> SEQUENCE: 11
cugugcgugu gacagcggcu ga                                               22

<210> SEQ ID NO 12
<211> LENGTH: 22
<212> TYPE: RNA
<213> ORGANISM: Homo sapiens

<400> SEQUENCE: 12
uuuguucguu cggcucgcgu ga                                               22

<210> SEQ ID NO 13
<211> LENGTH: 22
<212> TYPE: RNA
<213> ORGANISM: Homo sapiens

<400> SEQUENCE: 13
uaacacuguc ugguaacgau gu                                               22

<210> SEQ ID NO 14
<211> LENGTH: 22
<212> TYPE: RNA
<213> ORGANISM: Homo sapiens

<400> SEQUENCE: 14
ucggauccgu cugagcuugg cu                                               22

<210> SEQ ID NO 15
<211> LENGTH: 21
<212> TYPE: RNA
<213> ORGANISM: Homo sapiens

<400> SEQUENCE: 15
aucauagagg aaaauccacg u                                                21

<210> SEQ ID NO 16
<211> LENGTH: 21
<212> TYPE: RNA
<213> ORGANISM: Homo sapiens

<400> SEQUENCE: 16
aauggcgcca cuaggguugu g                                                21

<210> SEQ ID NO 17
<211> LENGTH: 23
<212> TYPE: RNA
<213> ORGANISM: Homo sapiens

<400> SEQUENCE: 17
uaaggugcau cuagugcaga uag                                              23
```

```
<210> SEQ ID NO 18
<211> LENGTH: 22
<212> TYPE: RNA
<213> ORGANISM: Homo sapiens

<400> SEQUENCE: 18
caaucagcaa guauacugcc cu                                              22

<210> SEQ ID NO 19
<211> LENGTH: 22
<212> TYPE: RNA
<213> ORGANISM: Homo sapiens

<400> SEQUENCE: 19
acugcugagc uagcacuucc cg                                              22

<210> SEQ ID NO 20
<211> LENGTH: 22
<212> TYPE: RNA
<213> ORGANISM: Homo sapiens

<400> SEQUENCE: 20
gcuacuucac aacaccaggg cc                                              22

<210> SEQ ID NO 21
<211> LENGTH: 23
<212> TYPE: RNA
<213> ORGANISM: Homo sapiens

<400> SEQUENCE: 21
guccaguuuu cccaggaauc ccu                                             23

<210> SEQ ID NO 22
<211> LENGTH: 21
<212> TYPE: RNA
<213> ORGANISM: Homo sapiens

<400> SEQUENCE: 22
ugauauguuu gauauugggu u                                               21

<210> SEQ ID NO 23
<211> LENGTH: 22
<212> TYPE: RNA
<213> ORGANISM: Homo sapiens

<400> SEQUENCE: 23
aaaagcuggg uugagagggc ga                                              22

<210> SEQ ID NO 24
<211> LENGTH: 22
<212> TYPE: RNA
<213> ORGANISM: Homo sapiens

<400> SEQUENCE: 24
cuggcccucu cugcccuucc gu                                              22

<210> SEQ ID NO 25
<211> LENGTH: 23
<212> TYPE: RNA
<213> ORGANISM: Homo sapiens

<400> SEQUENCE: 25
```

```
ugagcgccuc gacgacagag ccg                                          23

<210> SEQ ID NO 26
<211> LENGTH: 22
<212> TYPE: RNA
<213> ORGANISM: Homo sapiens

<400> SEQUENCE: 26
gucauacacg gcucuccucu cu                                           22

<210> SEQ ID NO 27
<211> LENGTH: 23
<212> TYPE: RNA
<213> ORGANISM: Homo sapiens

<400> SEQUENCE: 27
uucauuuggu auaaaccgcg auu                                          23

<210> SEQ ID NO 28
<211> LENGTH: 22
<212> TYPE: RNA
<213> ORGANISM: Homo sapiens

<400> SEQUENCE: 28
uauaccucag uuuuaucagg ug                                           22
```

CIRCULATING MIRNAS AS MARKERS FOR BREAST CANCER

The present invention is concerned with a method for diagnosing breast cancer in a subject comprising the steps of determining in a sample of a subject suspected to be afflicted with said breast cancer the amount of at least one miRNA or the amounts of at least the miRNAs of a combination of miRNAs selected from the group consisting of: (i) miR-801, (ii) miR-801 and miR-148b. (iii) miR-801 and miR-376c, (iv) miR-801 and miR-409-3p, (v) miR-801, miR-376c and miR-148b, (vi) miR-801, miR-409-3p and miR-376c, (vii) miR-801, miR-409-3p and miR-148b, (viii) miR-801, miR-376c, miR-409-3p and miR-148b, (ix) miR-148b, (x) miR-409-3p, (xi) miR-376c, (xii) miR-376c and miR-409-3p. (xiii) miR-148b and miR-376c, (xiv) miR-148b and miR-409-3p, (xv) miR-148b, miR-376c and miR-409-3p, (xvi) miR-127-3p, (xvii) miR-148b, (xvii) miR-376a, (xix) miR-376c, (xx) miR-409-3p, (xxi) miR-652, (xxii) miR-127-3p, miR-148b, miR-376a, miR-376c, miR-409-3p, miR-652, and miR-801, (xxiii) miR-127-3p, miR-148b, miR-652, and miR-801. (xxiv) miR-376a, miR-148b. miR-652, and miR-801, (xxv) miR-376c, miR-148b, miR-652, and miR-801, and (xxvi) miR-409-3p, miR-148b, miR-652, and miR-801 and comparing said amount with a reference or comparing said amounts with references, whereby breast cancer is to be diagnosed. The present invention is also concerned with methods for diagnosing metastasizing breast cancer in a subject and for determining the circulating tumor cell (CTC) status in a subject comprising the steps of (a) determining in a sample of a subject suspected to be afflicted with said metastasizing breast cancer the amount of at least one miRNA selected from the group consisting of: miR-801, miR-141, miR-200a, miR-200b, miR-200c, miR-203, miR-210, miR-375, miR-142-3p, and miR-768-3p, and (b) comparing said amount with a reference or comparing said amounts with references. Furthermore the present invention is concerned with the use of the miRNAs of the invention for diagnosing breast cancer, metastasizing breast cancer, or for determining the CTC status in a subject. Moreover, the present invention is concerned with devices and kits for carrying methods of the invention.

Breast cancer is the most common type of cancer and cause of death among women in industrialized countries. Worldwide approximately 1.3 million women develop breast cancer each year. Mortality rates have continued to decrease over the years due to all the efforts and advances made in early diagnosis and treatment (Jemal A, Bray F, Center M M, Ferlay J, Ward E, Forman D. Global cancer statistics. CA Cancer J Clin 2011; 61:69-90). Nevertheless, thousands of women die from this disease each year. In US women the overall five-year survival is 98% when diagnosed at an early stage as opposed to 23% when the disease has already spread to distant organs. Thus, early breast cancer detection belongs to one of the major challenges in the struggle against this disease. Mammographic screening is currently applied as the diagnostic standard. However, it has limitations due to its use of ionizing radiation and a false positive rate of 8-10%, also depending on the age of the individuals to be screened (Taplin S, Abraham L, Barlow W E, Fenton J J. Bems E A, Carney P A, Cutter G R, Sickles E A, Carl D, Elmore J G. Mammography facility characteristics associated with interpretive accuracy of screening mammography. J Natl Cancer Inst 2008; 100:876-87).

Protein based circulating tumor markers like carcinoembryonic antigen (CEA) and carbohydrate antigen 15-3 (CA 15-3) are widely used as prognostic markers, as well as in monitoring breast cancer treatment success and follow-up (Uehara M, Kinoshita T, Hojo T, Akashi-Tanaka S, Iwamoto E, Fukutomi T. Long-term prognostic study of carcinoembryonic antigen (CEA) and carbohydrate antigen 15-3 (CA 15-3) in breast cancer. Int J Clin Oncol 2008; 13:447-51; Harris L, Fritsche H, Mennel R, Norton L, Ravdin P, Taube S, Somerfield M R, Hayes D F, Bast R C, Jr. American Society of Clinical Oncology 2007 update of recommendations for the use of tumor markers in breast cancer. J Clin Oncol 2007; 25:5287-312) However, the sensitivity of these markers is low. Therefore, new sensitive and specific as well as minimally invasive markers are needed.

Metastatic breast cancer (MBC) is a major health issue, worldwide. Current treatment strategies target primarily palliative care with very few cases being cured. An alternate approach of tackling MBC is development of screening methods and applying biomarkers to identify high risk groups and therapy response. This could facilitate decision making for clinicians and help them adopt the appropriate treatment regime for the patients.

Circulating tumor cells (CTC) have been proposed as an FDA approved independent prognostic marker for metastasis, specifically for progression-free survival and overall survival. A cardinal cut off of greater than 5 CTCs per 7.5 ml of blood has been defined as CTC positive (Cristofanilli M, Budd G T, Ellis M J, Stopeck A, et al; Circulating tumor cells, disease progression, and survival in metastatic breast cancer; N Engl J Med. 2004 Aug. 19; 351(8):781-91). However, it is important to note that a significant fraction of patients with overt distant metastases are negative for CTCs. This could be partly contributed to the phenomenon of epithelial-mesenchymal transition in CTCs, in which case they can be missed by enumeration techniques that exploit the expression of epithelial markers such as EpCAM or cytokeratin-8, -18 and -19.

miRNAs are small, non-coding RNAs (~18-25 nucleotides in length) that regulate gene expression on a post-transcriptional level by degrading mRNA molecules or blocking their translation (Bartel D P.: MicroRNAs: genomics, biogenesis, mechanism, and function. Cell 2004; 116: 281-97). Hence, they play an essential role in the regulation of a large number of biological processes, including cancer (Calin G A, Dumitru C D, Shimizu M. Bichi R, Zupo S. Noch E, Aldler H, Rattan S, Keating M, Rai K, Rassenti L, Kipps T, et al. Frequent deletions and down-regulation of micro-RNA genes miR15 and miR16 at 13q14 in chronic lymphocytic leukemia. Proc Natl Acad Sci USA 2002:99: 15524-9). Under the standard nomenclature system, names are assigned to experimentally confirmed miRNAs. The prefix "mir" is followed by a dash and a number. The uncapitalized "mir-" refers to the pre-miRNA, while a capitalized "miR-" refers to the mature form. miRNAs with nearly identical sequences bar one or two nucleotides are annotated with an additional lower case letter. Species of origin is designated with a three-letter prefix, e.g. hsa for *Homo sapiens* (human). Two mature miRNAs originating from opposite arms of the same pre-miRNA are denoted with a -3p or -5p suffix.

Circulating miRNAs are defined as miRNAs present in the cell-free component of body fluids like plasma, serum, and the like. Lawrie et al. (Lawrie C H, Gal S, Dunlop H M, Pushkaran B, Liggins A P, Pulford K, Banham A H, Pezzella F, Boultwood J, Wainscoat J S, Hatton C S, Harris A L. Detection of elevated levels of tumour-associated microRNAs in serum of patients with diffuse large B-cell lymphoma. Br J Haematol 2008; 141:672-5) were among the first to demonstrate the presence of miRNAs in bodily fluids.

Since then, circulating miRNAs have been reported as aberrantly expressed in blood plasma or serum in different types of cancer, e.g. prostate, colorectal or esophageal carcinoma (Brase J C, Johannes M, Schlomm T, Faith M, Haese A. Steuber T, Beissbarth T, Kuner R, Sultmann H. Circulating miRNAs are correlated with tumor progression in prostate cancer. Int J Cancer 2011; 128:608-16.; Huang Z, Huang D, Ni S, Peng Z, Sheng W. Du X. Plasma microRNAs are promising novel markers for early detection of colorectal cancer. Int J Cancer 2010; 127:118-26.; Zhang C, Wang C, Chen X, Yang C, Li K, Wang J. Dai J, Hu Z, Zhou X, Chen L, Zhang Y, Li Y, et al. Expression profile of microRNAs in serum: a fingerprint for esophageal squamous cell carcinoma. Clin Chem 2010; 56:1871-9.). Their most important advantages include the possibility to be measured repeatedly in a minimally invasive manner as well as their remarkable stability in plasmalserum, where they circulate mostly outside of exosomes and are stable due to their binding to Argonaute proteins (Mitchell P S, Parkin R K, Kroh E M, Fritz B R, Wyman S K, Pogosova-Agadjanyan E L, Peterson A, Noteboom J, O'Briant K C, Allen A. Lin D W, Urban N, at al. Circulating microRNAs as stable blood-based markers for cancer detection. Proc Natl Acad Sci USA 2008:105: 10513-8; Turchinovich A, Weiz L, Langheinz A, Burwinkel B. Characterization of extracellular circulating microRNA. Nucleic Acids Res 2011; 39:7223-33; Arroyo J D, Chevillet J R. Kroh E M, Ruf I K, Pritchard C C, Gibson D F, Mitchell P S, Bennett C F, Pogosova-Agadjanyan E L, Stirewalt D L, Tait J F, Tewari M. Argonaute2 complexes carry a population of circulating microRNAs independent of vesicles in human plasma. Proc Natl Acad Sci USA 2011:108:5003-8).

There is thus an urgent need in the art for improved methods for the detection of breast cancer and metastasizing breast cancer. Moreover, there is a need for a reliable method for determining the CTC status of patient. Since the methods would preferably be also used in preventive screening of apparently healthy subjects, a low grade of invasiveness would be preferred.

Therefore, the present invention relates to a method for diagnosing breast cancer in a subject comprising the steps of: (a) determining in a sample of a subject suspected to be afflicted with said breast cancer the amount of at least one miRNA or the amounts of at least the miRNAs of a combination of miRNAs selected from the group consisting of: (i) miR-801, which appears to be a fragment of RNU11/U11 small nuclear RNA. (miRBase (Griffiths-Jones S. NAR 2004 32(Database Issue):D109-D111; Kozomara A, Griffiths-Jones S. NAR 2011 39(Database Issue):D152-D157) (ii) miR-801 and miR-148b, (iil) miR-801 and miR-376c, (iv) miR-801 and miR-409-3p, (v) miR-801, miR-376c and miR-148b, (vi) miR-801, miR-409-3p and miR-376c, (vii) miR-801, miR-409-3p and miR-148b, (viii) miR-801, miR-376c, miR-409-3p and miR-148b, (ix) miR-148b, (x) miR-409-3p, (xi) miR-376c, (xi) miR-376c and miR-409-3p, (xiii) miR-148b and miR-376c, (xiv) miR-148b and miR-409-3p, (xv) miR-148b, miR-376c and miR-409-3p, (xvi) miR-127-3p, (xvii) miR-148b, (xvii) miR-376a, (xix) miR-376c, (xx) miR-409-3p, (xxi) miR-652, (xxii) miR-127-3p, miR-148b, miR-376a, miR-376c, miR-409-3p, miR-652, and miR-801, (xxiii) miR-127-3p, miR-148b, miR-652, and miR-801, (xxiv) miR-376a, miR-148b, miR-652, and miR-801. (xxv) miR-376c, miR-148b, miR-652, and miR-801, and (xxvi) miR-409-3p, miR-148b, miR-652, and miR-801; and (b) comparing said amount with a reference or comparing said amounts with references, whereby breast cancer is to be diagnosed.

The method for diagnosing breast cancer, preferably, is an in vitro method. Moreover, it may comprise steps in addition to those explicitly mentioned above. For example, further steps may relate. e.g., to isolating miRNAs from a sample in step a), to the additional determination of other markers, or to the use of an automatic device in step a) and/or in step b).

The term "diagnosing" as used herein refers to assessing the probability according to which a subject is afflicted or will be afflicted with a disease or condition referred to in this specification. As will be understood by those skilled in the art, such an assessment is usually not intended to be correct for 100% of the subjects to be diagnosed. The term, however, requires that a statistically significant portion of subjects can be correctly diagnosed to be afflicted with the disease or condition. Whether a portion is statistically significant can be determined without further ado by the person skilled in the art using various well known statistic evaluation tools. e.g., determination of confidence intervals, and p-value determination, e.g. via binomial tests. Details are found in Dowdy and Wearden, Statistics for Research, John Wiley & Sons, New York 1983. Preferred confidence intervals are at least 90%, at least 95%, at least 97%, at least 98% or at least 99%. The significance levels of statistical tests are, preferably, 0.1, 0.05, 0.01, 0.005, or 0.0001. Preferably, the probability envisaged by the present invention allows that the diagnosis will be correct for at least 60%, at least 70%, at least 80%, or at least 90% of the subjects of a given cohort or population. Preferably, the diagnostic method has a sufficiently large sensitivity and specificity as described below. Preferably, the sensitivity envisaged by the present invention allows that the diagnosis of cases will be correct for at least 75%, at least 80%, at least 85%, at least 90%, or at least 95% of the afflicted subjects of a given cohort or population. Also, preferably, the specificity envisaged by the present invention allows that the diagnosis will be correct for at least 25%, at least 50%, at least 75%, at least 80%, at least 85%, at least 90%, or at least 95% of the unafflicted subjects of a given cohort or population.

The term "breast cancer" (BC) as used herein relates to an abnormal hyperproliferation of breast tissue cells in a subject. Preferably, the breast cancer is a primary breast cancer, more preferably with a tumor size classification in situ (IS) or pT3, more preferably with a tumor size classification of pT1 or pT2.

The term "subject" as referred to herein encompasses animals, preferably mammals, and, more preferably, humans. More preferably, said subject was in the past afflicted with, is at present afflicted with, is suspected to be afflicted with, or is at risk to be afflicted with breast cancer. Subjects that are afflicted with the said disease can be identified by the accompanying symptoms known for the disease. These symptoms are known in the art and described, e.g., in Breast Cancer Facts & FIGS. 2011-2012, issued by the American Cancer Society, Inc., Atlanta. However, a subject suspected to be afflicted with the aforementioned disease may also be an apparently healthy subject, e.g., investigated by routine clinical screening, or may be a subject being at risk for developing the aforementioned disease. Risk groups (e.g. individuals with a genetic predisposition to develop breast cancer) for the disease are known in the art and described in, e.g., Dumitrescu R G, Cotarla I: Understanding breast cancer risk—where do we stand in 2005? Journal of Cellular and Molecular Medicine (2005); 9(1):208-221; Bradbury A R, Olopade O I: Genetic susceptibility to breast cancer. Reviews in Endocrine and Metabolic Disorders (2007); 8(3):255-267. Preferably, the subject is female. More preferably, the subject is a woman at most 50 years old.

The term "sample", as used herein, refers to a sample of a body fluid, to a sample of separated cells or to a sample from a tissue or an organ or to a sample of wash/rinse fluid obtained from an outer or inner body surface Samples can be obtained by well-known techniques and include, preferably, scrapes, swabs or biopsies from the digestive tract, liver, pancreas, anal canal, the oral cavity, the upper aerodigestive tract and the epidermis. Such samples can be obtained by use of brushes, (cotton) swabs, spatula, rinse/wash fluids, punch biopsy devices, puncture of cavities with needles or surgical instrumentation. More preferably, samples are samples of body fluids, e.g., preferably, blood, plasma, serum, urine, saliva, lacrimal fluid, and fluids obtainable from the breast glands, e.g. milk. More preferably, the samples of body fluids are free of cells of the subject. Tissue or organ samples may be obtained from any tissue or organ by, e.g., biopsy or other surgical procedures. Separated cells may be obtained from the body fluids or the tissues or organs by separating techniques such as filtration, centrifugation or cell sorting Preferably, cell, tissue or organ samples are obtained from those body fluids, cells, tissues or organs which are known or suspected to contain the miRNAs of the present invention. More preferably, samples are obtained from those body fluids, cells, tissues or organs described herein below to contain the miRNAs of the present invention. Preferably, the sample is a blood sample, more preferably a plasma sample, most preferably a plasma sample processed as described herein below. Preferably, in case the sample is a tumor sample, the miRNA is not miR-801.

The term "miRNA" or "microRNA" is understood by the skilled artisan and relates to a short ribonucleic acid (RNA) molecule found in eukaryotic cells and in body fluids of metazoan organisms. It is to be understood that the present invention preferably also encompasses pri-miRNAs, and the pre-miRNAs of the miRNAs of the present invention. Thus preferably, a miRNA-precursor consists of 25 to several thousand nucleotides, more preferably 40 to 130 nucleotides, even more preferably 50 to 120 nucleotides, or, most preferably 60 to 110 nucleotides. Preferably, a miRNA consists of 5 to 100 nucleotides, more preferably 10 to 50 nucleotides, even more preferably 12 to 40 nucleotides, or, most preferably 18 to 26 nucleotides. Preferably, the miRNAs of the present invention are miRNAs of human origin, i.e. they are encoded in the human genome. Also preferably, the term miRNA relates to the "guide" strand which eventually enters the RNA-induced silencing complex (RISC) as well as to the "passenger" strand complementary thereto. Preferably, the mIRNA or miRNAs used in the method for diagnosing breast cancer is/are selected from the list consisting of miR-801 (SEQ ID NO: 1, miRBase (Griffiths-Jones S., NAR 2004 32(Database Issue):D109-D111; Kozomara A, Griffiths-Jones S., NAR 2011 39(Database Issue): D152-D157) ID MI0005202: 5'-GAUUGCUCUGCGUGCGGAAUCGAC-3'), miR-148b (SEQ ID NO: 2, miRBase ID MI0000811, more preferably MIMAT0000759: 5'-UCAGUGCAUCACAGAAC-UUUGU-3'; new ID in miRBase release 18: hsa-miR-148b-3p), miR-376c, preferably miR-376c-3p (SEQ ID NO: 3, miRBase ID MI0000776, more preferably MIMAT0000720: 5'-AACAUAGAGGAAAAUUCCACGU-3': formerly known as hsa-miR-368), miR-409-3p (SEQ ID NO: 4, miRBase ID MI0001735, more preferably MIMAT0001639: 5'-GAAUGUUGCUCGGUGAAC-CCCU-3'), miR-203 (SEQ ID NO: 5, miRBase ID M10000283, more preferably MIMAT0000264:: 5'-GUGAAAUGUUUAGGACCACUAG-3'), miR-768-3p (SEQ ID NO: 6, miRBase ID MI0005117: 5'-UCA-CAAUGCUGACACUCAAACUGCUGAC-3'), miR-142-3p (SEQ ID NO: 7, miRBase ID MI0000458, more preferably MIMAT0000434: 5'-UGUAGUGUUUCCUACUUUAUGGA-3'), miR-141 (SEQ ID NO: 8, miRBase ID MI0000457, more preferably MIMAT0000432: 5'-UAACACUGUCUG-GUAAAGAUGG-3"; new ID in miRBase release 18: hsa-miR-141-3p), miR-200b (SEQ ID NO: 9, miRBase ID MI0000342, more preferably MIMAT0000318: 5'-UAAUACUGCCUGGUAAUGAUGA-3'; new ID in miRBase release 18: hsa-miR-200b-3p), miR-200c (SEQ ID NO: 10, miRBase ID MI0000650, more preferably MIMAT0000617: 5'-UAAUACUGC-CGGGUAAUGAUGGA-3'; new ID in miRBase release 18: hsa-miR-200c-3p), miR-210 (SEQ ID NO: 11, miRBase ID MI0000286, more preferably MIMAT0000267: 5'-CU-GUGCGUGUGACAGCGGCUGA-3'), miR-375 (SEQ ID NO: 12, miRBase ID MI0000783, more preferably MIMAT0000728: 5'-UUUGUUCGUUCGG-CUCGCGUGA-3'), miR-200a (SEQ ID NO: 13, miRBase ID MI0000737, more preferably MIMAT0000682: 5'-UAACACUGUCUGGUAACGAUGU-3'; new ID in miRBase release 18: hsa-miR-200a-3p), miR-127-3p (SEQ ID NO: 14, miRBase ID MI0000472, more preferably MIMAT0000446: 5'-UCGGAUCCGUCUGAGCUUG-GCU-3'), miR-376a (miRBase ID MI0000784, more preferably SEQ ID NO: 15, miRBase ID MIMAT0000729: 5'-AUCAUAGAGGAAAAUCCACGU-3'; new ID in miRBase release 19: hsa-miR-376a-3p), miR-652 (miRBase ID MI0003667, more preferably SEQ ID NO: 16, miRBase ID MIMAT0003322: 5'-AAUGGCGCCACUAGGGUUGUG-3'; new ID in miRBase release 19: hsa-miR-652-3p), hsa-miR-18a (miRBase ID MI0000072, more preferably SEQ ID NO: 17, miRBase ID MIMAT0000072: 5'-UAAGGUG-CAUCUAGUGCAGAUAG-3'), hsa-miR-34a* (also known as hsa-miR-34a-3p; miRBase ID MI0000268, more preferably SEQ ID NO: 18, miRBase ID MIMAT0004557: 5'-CAAUCAGCAAGUAUACUGCCCU-3'), hsa-miR-93* (also known as hsa-miR-93-3p; miRBase ID MI0000095, more preferably SEQ ID NO: 19, miRBase ID MIMAT0004509: 5'-ACUGCUGAGCUAGCACUUC-CCG-3'), hsa-miR-138-1' (also known as hsa-miR-138-1-3p; miRBase ID MI0000476, more preferably SEQ ID NO: 20, miRBase ID MIMAT0004607: 5'-GCUACUUCA-CAACACCAGGGCC-3'), hsa-miR-145 (also known as hsa-miR-145-5p; miRBase ID MI0000461, more preferably SEQ ID NO: 21, miRBase ID MIMAT0000437: 5'-GUC-CAGUUUUCCCAGGAAUCCCU-3'), hsa-miR-190b (miRBase ID MI0005545, more preferably SEQ ID NO: 22, miRBase ID MIMAT0004929: 5'-UGAUAU-GUUUGAUAUUGGGUU-3'), hsa-miR-320 (also known as hsa-miR-320a; miRBase ID MI0000542, more preferably SEQ ID NO: 23, miRBase ID MIMAT0000510: 5'-AAAAGCUGGGUUGAGAGGGCGA-3'), hsa-miR-328 (miRBase ID MI0000804, more preferably SEQ ID NO: 24, miRBase ID MIMAT0000752: 5'-CUGGCCCUCUCUGC-CCUUCCGU-3'), hsa-miR-339-3p (miRBase ID MI0000815, more preferably SEQ ID NO: 25, miRBase ID. MIMAT0004702: 5'-UGAGCGCCUCGACGACA-GAGCCG-3'), hsa-miR-485-3p (miRBase ID MI0002489, more preferably SEQ ID NO: 26, miRBase ID MIMAT0002176: 5'-GUCAUACACGGCUCUCCU-CUCU-3'), hsa-miR-579 (miRBase ID MI0003586, more preferably SEQ ID NO: 27, miRBase ID MIMAT0003244:

5'-UUCAUUUGGUAUAAACCGCGAUU-3'), and hsa-miR-875-5p (miRBase ID M10005541, more preferably SEQ ID NO: 28, miRBase ID MIMAT0004922: 5'-UAUACCUCAGUUUUAUCAGGUG-3').

The term "combination of miRNAs" relates to combinations of the miRNAs of the present invention. It is to be understood that a specific combination of miRNAs may be used for diagnosing breast cancer (BC) or for diagnosing metastasizing breast cancer (MBC), or both. Preferred combinations for diagnosing BC are miR-801+miR-148b, miR-801+miR-376c, miR-801+miR-409-3p, miR-801+miR-376c+miR-148b, miR-801+miR-409-3p+miR-376c, miR-801+miR-409-3p+miR-148b, miR-801+miR-376c+miR-409-3p+miR-148b, miR-376c+miR-409-3p, miR-148b+miR-376c, miR-148b+miR-409-3p, and miR-148b+miR-376c+miR-409-3p. Most preferred combinations for diagnosing BC are miR-127-3p+miR-148b+miR-376a+miR-376c+miR-409-3p+miR-652+miR-801, miR-127-3p+miR-148b+miR-652+miR-801, miR-376a+miR-148b+miR-652+miR-801, miR-376c+miR-148b+miR-652+miR-801, and miR-409-3p+miR-148b, miR-652+miR-801.

The amount of a miRNA can be determined in a sample of a subject by techniques well known in the art. Depending on the nature of the sample, the amount may be determined by PCR based techniques for quantifying the amount of a polynucleotide or by other methods like mass spectrometry or (next generation) sequencing or one of the methods described in the examples (Cissell K A, Deo S K. Trends in microRNA detection. Anal Bioanal Chem. 2009; 394(4): 1109-1116 or de Planell-Saguer M, Rodicio M C. Analytical aspects of microRNA in diagnostics: a review. Anal Chim Acta 2011 Aug. 12; 699(2):134-52).

The term "determining the amounts of at least the miRNAs of a combination of miRNAs", as used herein, preferably relates to determining the amount of each of the miRNAs of the combination separately in order to be able to compare the amount of each miRNA of the combination to a reference specific for said miRNA.

"Comparing" as used herein encompasses comparing the amount of the miRNA referred to herein which is comprised by the sample to be analyzed with an amount of the said miRNA in a suitable reference sample as specified elsewhere herein in this description. It is to be understood that comparing as used herein refers to a comparison of corresponding parameters or values, e.g., an absolute amount of the miRNA as referred to herein is compared to an absolute reference amount of said miRNA; a concentration of the miRNA as referred to herein is compared to a reference concentration of said miRNA; an intensity signal obtained from the miRNA as referred to herein in a test sample is compared to the same type of intensity signal of said miRNA in a reference sample. The comparison referred to in the methods of the present invention may be carried out manually or computer assisted. For a computer assisted comparison, the value of the determined amount may be compared to values corresponding to suitable references which are stored in a database by a computer program. The computer program may further evaluate the result of the comparison by means of an expert system. Accordingly, the result of the identification referred to herein may be automatically provided in a suitable output format.

The term "reference", "reference value", or "reference amount" as used herein refers to an amount of miRNA, which allows assessing if being afflicted with BC or MBC or not being afflicted with BC or MBC is to be assumed for the subject from which the sample is derived. A suitable reference value may be determined from a reference sample to be analyzed together, i.e. simultaneously or subsequently, with the sample.

Reference amounts can, in principle, be calculated for a group or cohort of subjects as specified herein based on the average or median values for a given miRNA by applying standard methods of statistics. In particular, accuracy of a test such as a method aiming to diagnose an event, or not, is best described by its receiver-operating characteristics (ROC) (see especially Zweig 1993, Clin. Chem. 39:561-577). The ROC graph is a plot of all of the sensitivity versus specificity pairs resulting from continuously varying the decision threshold over the entire range of data observed. The clinical performance of a diagnostic method depends on its accuracy, i.e. its ability to correctly allocate subjects to a certain prognosis or diagnosis. The ROC plot indicates the overlap between the two distributions by plotting the sensitivity versus 1-specificity for the complete range of thresholds suitable for making a distinction. On the y-axis is sensitivity, or the true-positive fraction, which is defined as the ratio of number of true-positive test results to the sum of number of true-positive and number of false-negative test results. This has also been referred to as positivity in the presence of a disease or condition. It is calculated solely from the affected subgroup. On the x-axis is the false-positive fraction, or 1-specificity, which is defined as the ratio of number of false-positive results to the sum of number of true-negative and number of false-positive results. It is an index of specificity and is calculated entirely from the unaffected subgroup. Because the true- and false-positive fractions are calculated entirely separately, by using the test results from two different subgroups, the ROC plot is independent of the prevalence of the event in the cohort. Each point on the ROC plot represents a sensitivity/-specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45° diagonal line from the lower left corner to the upper right corner. Most plots fall in between these two extremes. If the ROC plot falls completely below the 45° diagonal, this is easily remedied by reversing the criterion for "positivity" from "greater than" to "less than" or vice versa. Qualitatively, the closer the plot is to the upper left corner, the higher the overall accuracy of the test. Dependent on a desired confidence interval, a threshold can be derived from the ROC curve allowing for the diagnosis or prediction for a given event with a proper balance of sensitivity and specificity, respectively. Accordingly, the reference to be used for the methods of the present invention can be generated, preferably, by establishing a ROC for said cohort as described above and deriving a threshold amount there from. Dependent on a desired sensitivity and specificity for a diagnostic method, the ROC plot allows deriving suitable thresholds. Preferably, the reference amounts lie within the range of values that represent a sensitivity of at least 75% and a specificity of at least 45%, or a sensitivity of at least 80% and a specificity of at least 40%, or a sensitivity of at least 85% and a specificity of at least 33%, or a sensitivity of at least 90% and a specificity of at least 25%.

Preferably, the reference amount as used herein is derived from samples of subjects obtained before treatment, but for which it is known if their donors were being afflicted with BC or MBC or not. This reference amount level may be a discrete figure or may be a range of figures. Evidently, the reference level or amount may vary between individual species of miRNA. The measuring system therefore, preferably, is calibrated with a sample or with a series of samples comprising known amounts of each specific miRNA. It is understood by the skilled person that in such case the amount of miRNA can preferably be expressed as arbitrary units (AU). Thus, preferably, the amounts of miRNA are determined by comparing the signal obtained from the sample to signals comprised in a calibration curve. The reference amount applicable for an individual subject may vary depending on various physiological parameters such as age or subpopulation. Thus, a suitable reference amount may be determined by the methods of the as present invention from a reference sample to be analyzed together, i.e. simultaneously or subsequently, with the test sample. Moreover, a threshold amount can be preferably used as a reference amount. A reference amount may, preferably, be derived from a sample of a subject or group of subjects being afflicted with BC or MBC which islare known to be afflicted with BC or MBC. A reference amount may, preferably, also be derived from a sample of a subject or group of subjects known to be not afflicted with BC or MBC. It is to be understood that the aforementioned amounts may vary due to statistics and errors of measurement. A deviation, i.e. a decrease or an increase of the miRNA amounts referred to herein is, preferably, a statistically significant deviation, i.e. a statistically significant decrease or a statistically significant increase.

In a preferred embodiment of the method for diagnosing breast cancer, the amount of miRNA and the reference amount are determined in a sample of a body fluid, preferably blood, plasma, serum, saliva, or a fluid obtainable from the breast glands, more preferably plasma processed as detailed herein below and the reference amounts are, preferably, those which are the average or mean amounts found in subjects being afflicted with BC for a given population or cohort of subjects. More preferably, the reference amounts are reference ranges which represent the 75th, the 80th, the 85th, the 90th, the 91st, the 92nd, the 93rd, the 94th, the 95th, the 96th, the 97th, the 98th, or the 99th percentile of amounts found in subjects being afflicted with BC for a given population or cohort of subjects. Also preferably, the reference amounts are reference ranges which represent the average or mean values +/−1, 1.5, 2, 2.5, 3, 3.5, 4, 4.5 standard deviations of amounts found in subjects being afflicted with BC for a given population or cohort of subjects. In such case, it has been found that an amount of miRNA equal to or increased relative to the reference amount or reference range is, preferably, indicative of a subject being afflicted with BC while a decreased amount of miRNA is indicative for a subject not being afflicted with BC. As is detailed herein in the examples, preferably, a decreased amount of miRNA is indicative of a subject not being afflicted with BC, and an increased amount of miRNA is indicative of a subject being afflicted with BC. Meaning, preferably, that a subject with a high amount of miRNA in a sample specified in this paragraph has a high probability to be afflicted with BC, and that a subject with a low amount of miRNA has a low probability to be afflicted with BC.

In another preferred embodiment of the method for diagnosing breast cancer, the amount of miRNA and the reference amount are determined in a sample of a body fluid, preferably blood, plasma, serum, saliva, or a fluid obtainable from the breast glands, more preferably plasma processed as detailed herein below and the reference amounts are, preferably, those which are the average or mean amounts found in subjects known not to be afflicted with BC, i.e. control subjects, for a given population or cohort of subjects. More preferably, the reference amounts are reference ranges which represent the 75th, the 80th, the 85th, the 90th, the 91st, the 92nd, the 93rd, the 94th, the 95th, the 96th, the 97th, the 98th, or the 99th percentile of amounts found in subjects known not to be afflicted with BC, i.e. control subjects, for a given population or cohort of subjects. Also preferably, the reference amounts are reference ranges which represent the average or mean values +/−1, 1.5, 2, 2.5, 3, 3.5, 4, or 4.5 standard deviations of amounts found in subjects known not to be afflicted with BC, i.e. control subjects, for a given population or cohort of subjects. In such case, it has been found that an amount of miRNA increased relative to the reference amount or reference range is, preferably, indicative of a subject being afflicted with BC while an amount essentially equal to the reference amount or within the reference range of miRNA is indicative for a subject not being afflicted with BC. Meaning, preferably, that a subject with a high amount of miRNA in a sample specified in this paragraph has a high probability to be afflicted with BC, and that a subject with an amount of miRNA corresponding to the reference amount or lying within the reference range has a low probability to be afflicted with BC.

In a more preferred embodiment of the method for diagnosing breast cancer, the amount of miRNA and the reference amount are determined in a sample of a body fluid, preferably blood, plasma, serum, saliva, or a fluid obtainable from the breast glands, more preferably plasma processed as detailed herein below and the reference amounts are, preferably, those which represent the maximal value of the sum of the method's sensitivity and specificity levels as specified by the ROC curve which is obtained for the comparison of a given population of cohort of subjects being afflicted with BC with a given population of cohort of subjects not being afflicted with BC, i.e. control subjects.

In another preferred embodiment of the method for diagnosing breast cancer, the amount of miRNA and the reference amount are determined in a sample from a tumor, preferably a breast tumor or a metastasis thereof, and the reference amounts are, preferably, those which are the average, mean, or median amounts found in subjects or samples known not to be afflicted with BC, i.e. control subjects or tissues, for a given population or cohort of subjects. More preferably, the reference amounts are reference ranges which represent the $75^{th}$, the $80^{th}$, the $85^{th}$, the $90^{th}$, the $91^{st}$, the $92^{nd}$, the $93^{rd}$, the $94^{th}$, the $95^{th}$, the $96^{th}$, the $97^{th}$, the $98^{th}$, or the $99^{th}$ percentile of amounts found in subjects known not to be afflicted with BC. i.e. control subjects, for a given population or cohort of subjects. Also preferably, the reference amounts are reference ranges which represent the average or mean values +/−1, 1.5, 2, 2.5, 3, 3.5, 4, or 4.5 standard deviations of amounts found in subjects known not to be afflicted with BC, i.e. control subjects, for a given population or cohort of subjects. In such case, it has been found that an amount of miRNA decreased relative to the reference amount or reference range is, preferably, indicative of a subject being afflicted with BC while an amount essentially equal to the reference amount or within the reference range of miRNA is indicative for a subject not being afflicted with BC. Meaning, preferably, that a subject with a low amount of miRNA in a sample specified in this paragraph has a high probability to be afflicted with BC and that a subject with an amount of miRNA corresponding to the reference amount or lying within the reference range has a low probability to be afflicted with BC.

In another preferred embodiment of the method for diagnosing breast cancer, the amount of miRNA and the reference amount are determined in a sample from a tumor, preferably a breast tumor or a metastasis thereof, and the reference amounts are, preferably, those which are the average, mean, or median amounts found in subjects known to be afflicted with BC for a given population or cohort of subjects. More preferably, the reference amounts are reference ranges which represent the 75th, the 80th, the 85th, the 90th, the 91st, the 92nd, the 93rd, the 94th, the 95th, the 96th, the 97th, the 98th, or the 99th percentile of amounts found in subjects known to be afflicted with BC for a given population or cohort of subjects. Also preferably, the reference amounts are reference ranges which represent the average or mean values +/−1, 1.5, 2, 2.5, 3, 3.5, 4, or 4.5 standard deviations of amounts found in subjects known to be afflicted with BC for a given population or cohort of subjects. In such case, it has been found that an amount of miRNA decreased or essentially equal to relative to the reference amount or reference range is, preferably, indicative of a subject being afflicted with BC while an amount above the reference range of miRNA is indicative for a subject being afflicted with BC.

In a more preferred embodiment of the method for diagnosing breast cancer, the amount of miRNA and the reference amount are determined in a sample from a tumor, preferably a breast tumor or a metastasis thereof, and the reference amounts are, preferably, those which represent the maximal value of the sum of the method's sensitivity and specificity levels as specified by the ROC curve which is obtained for the comparison of a given population of cohort of subjects being afflicted with BC prior to the treatment with a given population of cohort of subjects not being afflicted with BC, i.e. control subjects.

The definitions made above apply mutatis mutandis to the following:

The present invention also relates to a method for diagnosing metastasizing breast cancer in a subject comprising the steps of: (a) determining in a sample of a subject suspected to be afflicted with said metastasizing breast cancer the amount of at least one miRNA selected from the group consisting of: miR-141, miR-142-3p, miR-200a, miR-200b, miR-200c, miR-203, miR-210, miR-375, miR-768-3p, and miR-801, and (b) comparing said amount with a reference or comparing said amounts with references, whereby metastasizing breast cancer is to be diagnosed.

The present invention further relates to a method for determining the circulating tumor cell (CTC) status in a subject comprising the steps of: (a) determining in a sample of a subject suspected to be afflicted with breast cancer the amount of at least one miRNA selected from the group consisting of: miR-801, miR-141, miR-142-3p, miR-200a, miR-200b, miR-200c, miR-203, miR-210, miR-375, and miR-768-3p, and (b) comparing said amount with a reference or comparing said amounts with references, whereby the CTC status is to be determined.

The method for diagnosing metastasizing breast cancer and the method for determining the CTC status in a subject, preferably, are in vitro methods. Moreover, the methods may comprise steps in addition to those explicitly mentioned above. For example, further steps may relate, e.g., to isolating miRNAs from a sample in step a), to the additional determination of other markers, to the use of an automatic device in step a) and/or in step b), or to the diagnosis of breast cancer prior to applying the method.

As used herein, the term "metastatic breast cancer" (MBC) relates to a breast cancer wherein cancer cells grow as a metastasis at least one secondary site, i.e. a non-adjacent organ or part of the body of a subject.

The term "circulating tumor cell" or "CTC" is understood by the skilled artisan and relates to a tumor cell detached from the primary or metastatic tumor and circulating in the bloodstream. It is to be understood that the number of CTC is a prognostic marker for disease and therapy outcome in breast cancer, e.g. for overall survival. The term "CTC status" relates to the presence or absence of more than a reference amount of CTC in a sample. Preferably, the reference amount of CTC is 2, 2.5, 3, 3.5, 4, 4.5, 5, 5.5, 6, 6.5, 7, or 7.5 CTC/7.5 ml blood, 5 CTC/7.5 ml blood being more preferred. In subjects where a blood sample comprises more than said reference amount of CTC, the CTC status is unfavorable, indicating a low probability of successful treatment and a low progression-free and overall survival probability. Conversely, in subjects where a blood sample comprises less than said reference amount of CTC, the CTC status is favorable, indicating a high probability of successful treatment and a high progression-free and overall survival probability. Advantageously, it has been found in the present invention that the amounts of the miRNAs used for determining the CTC status of a subject as defined herein below are indicative of the CTC status of a subject. Thus, determining the CTC status in a subject as used herein relates to determining the amount or amounts of said miRNA or miRNAs and thus obtaining an indication of the subject's CTC status. Preferably, the status can be diagnosed to be "favorable" or "unfavorable".

Preferably, the miRNA or miRNAs used in the method for diagnosing metastasizing breast cancer or in the method for determining the CTC status in a subject is/are selected from the list consisting of miR-801, miR-141, miR-142-3p, miR-200a, miR-200b, miR-200c, miR-203, miR-210, miR-375, and miR-768-3p: miR-801, miR-203, and miR-768-3p being most preferred.

Preferred combinations of miRNAs for diagnosing MBC or for determining the CTC status of a subject are at least two miRNAs selected from at least two different groups of miRNAs, said groups being selected from: (i) a group consisting of miR-142-3p and miR-768-3p, (ii) a group consisting of miR-203, (iii) a group consisting of miR-375, (iv) a group consisting of miR-210 and miR-801, (v) a group consisting of miR-141, miR-200a, miR-200b, miR-200c. Preferred combinations for diagnosing MBC are miR-141+miR-200b+miR-200c+miR-210+miR-768-3p, miR-141+miR-210+miR-801+miR-142-3p+miR-768-3p, miR-141+miR-200c+miR-210+miR-768-3p, miR-141+miR-200b+miR-210+miR-375+miR-801+miR-142-3p+miR-768-3p, miR-141+miR-200b+miR-375+miR-801, miR-141+miR-200b+miR-375+miR-801+miR-203+miR-768-3p, miR-141+miR-142-3p+miR-200b+miR-200c+miR-210+miR-375+miR-203+miR-801+miR-768-3p, miR-200c+miR-210+miR-768-3p, or miR-141+miR-200c+miR-210+miR-801+miR-768-3p. Preferred combinations for determining the CTC status of a subject are miR-141+miR-200b, miR-141+miR-200b, miR-142-3p, miR-768-3p, miR-141+miR-200b+miR-142-3p+miR-768-3p, miR-141+miR-200b+miR-375, miR-141+miR-200b+miR-375+miR-210+miR-203, or miR-141+miR-200b+miR-142-3p+miR-768-3p.

In a preferred embodiment of the method for diagnosing metastasizing breast cancer, the amount of miRNA and the reference amount are determined in a sample of a body fluid, preferably blood, plasma, serum, saliva, or a fluid obtainable from the breast glands, more preferably plasma processed as detailed herein below and the reference amounts are, preferably, those which are the average or mean amounts found in subjects known not to be afflicted with MBC, i.e. control subjects, for a given population or cohort of subjects. More preferably, the reference amounts are reference ranges which represent the 75th, the 80th, the 85th, the 90th, the 91st, the 92nd, the 93rd, the 94th, the 95th, the 96th, the 97th, the 98th, or the 99th percentile of amounts found in subjects known not to be afflicted with MBC, i.e. control subjects, for a given population or cohort of subjects. Also preferably, the reference amounts are reference ranges which represent the average or mean values+/−1, 1.5, 2, 2.5, 3, 3.5, 4, or 4.5 standard deviations of amounts found in subjects known not to be afflicted with MBC, i.e. control subjects, for a given population or cohort of subjects. In such case, it has been found that an amount of miR-203, miR-375, miR-210, miR-801, miR-141, miR-200a, miR-200b, or miR-200c increased relative to the reference amount or reference range is, preferably, Indicative of a subject being afflicted with MBC while an amount essentially equal to the reference amount or within the reference range is indicative for a subject not being afflicted with MBC. Meaning, preferably, that a subject with a high amount of miR-203, miR-375, miR-210, miR-801, miR-141, miR-200a, miR-200b, or miR-200c in a sample specified in this paragraph has a high probability to be afflicted with BC, and that a subject with an amount of miRNA corresponding to the reference amount or lying within the reference range has a low probability to be afflicted with BC. Conversely, it has been found that an amount of miR-768-3p decreased relative to the reference amount or reference range is, preferably, indicative of a subject being afflicted with MBC while an amount of miR-768-3p equal to the reference amount or within the reference range is indicative for a subject not being afflicted with MBC. Meaning, preferably, that a subject with a low amount of miR-768-3p in a sample specified in this paragraph has a high probability to be afflicted with MBC, and that a subject with an amount of miRNA corresponding to the reference amount or lying within the reference range has a low probability to be afflicted with MBC In a preferred embodiment of the method for diagnosing metastasizing breast cancer, the amount of miRNA and the reference amount are determined in a sample of a body fluid, preferably blood, plasma, serum, saliva, or a fluid obtainable from the breast glands, more preferably plasma processed as detailed herein below and the reference amounts are, preferably, those which are the average or mean amounts found in subjects known to be afflicted with MBC for a given population or cohort of subjects. More preferably, the reference amounts are reference ranges which represent the 75th, the 80th, the 85th, the 90th, the 91st, the 92nd, the 93rd, the 94th, the 95th, the 96th, the 97th, the 98th, or the 99th percentile of amounts found in subjects known to be afflicted with MBC for a given population or cohort of subjects. Also preferably, the reference amounts are reference ranges which represent the average or mean values+/− 1, 1.5, 2, 2.5, 3, 3.5, 4, or 4.5 standard deviations of amounts found in subjects known to be afflicted with MBC for a given population or cohort of subjects. In such case, it has been found that an amount of miR-203, miR-375, miR-210, miR-801, miR-141, miR-200a, miR-200b, or miR-200c decreased relative to the reference amount or reference range is, preferably, indicative of a subject being afflicted with MBC while an amount essentially equal to the reference amount or within the reference range is indicative for a subject being afflicted with MBC. Meaning, preferably, that a subject with a high amount of miR-203, miR-375, miR-210, miR-801, miR-141, miR-200a, miR-200b, or miR-200c in a sample specified in this paragraph has a high probability to be afflicted with MBC, and that a subject with an amount of miRNA lower than the reference has a low probability to be afflicted with MBC. Conversely, it has been found that an amount of miR-768-3p increased or essentially equal relative to the reference amount or reference range is, preferably, indicative of a subject being afflicted with MBC while an amount of miR-768-3p lower than the reference range is indicative for a subject not being afflicted with MBC. Meaning, preferably, that a subject with a high amount of miR-768-3p in a sample specified in this paragraph has a high probability to be afflicted with MBC, and that a subject with a low amount of miRNA relative to the reference amount has a low probability to be afflicted with MBC.

In a more preferred embodiment of the method for diagnosing metastasizing breast cancer, the amount of miRNA and the reference amount are determined in a sample of a body fluid, preferably blood, plasma, serum, saliva, or a fluid obtainable from the breast glands, more preferably plasma processed as detailed herein below and the reference amounts are, preferably, those which represent the maximal value of the sum of the method's sensitivity and specificity levels as specified by the ROC curve which is obtained for the comparison of a given population of cohort of subjects being afflicted with MBC with a given population of cohort of subjects not being afflicted with MBC. Also preferably, the reference amounts lie within the range of values that represent a sensitivity of at least 75% and a specificity of at least 65%, or a sensitivity of at least 80% and a specificity of at least 55%, or a sensitivity of at least 85% and a specificity of at least 45%, or a sensitivity of at least 90% and a specificity of at least 35%.

In a preferred embodiment of the method for determining the CTC status in a subject, the amount of miRNA and the reference amount are determined in a sample of a body fluid, preferably blood, plasma, serum, saliva, or a fluid obtainable from the breast glands, more preferably plasma processed as detailed herein below and the reference amounts are, preferably, those which are the average or mean amounts found in subjects known to have a favorable CTC status, for a given population or cohort of subjects. More preferably, the reference amounts are reference ranges which represent the 75th, the 80th, the 85th, the 90th, the 91st, the 92nd, the 93rd, the 94th, the 95th, the 96th, the 97th, the 98th, or the 99th percentile of amounts found in subjects known to have a favorable CTC status, for a given population or cohort of subjects. Also preferably, the reference amounts are reference ranges which represent the average or mean values+/− 1, 1.5, 2, 2.5, 3, 3.5, 4, 4.5 standard deviations of amounts found in subjects known to have a favorable CTC status, for a given population or cohort of subjects. In such case, it has been found that an amount of miR-203, miR-375, miR-210, miR-801, miR-141, miR-200a, miR-200b, or miR-200c increased relative to the reference amount or reference range is, preferably, indicative of a subject having an unfavorable CTC status while an amount essentially equal to the reference amount or within the reference range is indicative for a subject having a favorable CTC status.

In another preferred embodiment of the method for determining the CTC status in a subject, the amount of miRNA and the reference amount are determined in a sample of a body fluid, preferably blood, plasma, serum, saliva, or a fluid obtainable from the breast glands, more preferably plasma processed as detailed herein below and the reference amounts are, preferably, those which are the average or mean amounts found in subjects known to have an unfavorable CTC status, for a given population or cohort of subjects. More preferably, the reference amounts are reference ranges which represent the 75th, the 80th, the 85th, the 90th, the 91st, the 92nd, the 93rd, the 94th, the 95th, the 96th, the 97th, the 98th, or the 99th percentile of amounts found in subjects known to have an unfavorable CTC status, for a given population or cohort of subjects. Also preferably, the reference amounts are reference ranges which represent the average or mean values+/−1, 1.5, 2, 2.5, 3, 3.5, 4, 4.5 standard deviations of amounts found in subjects known to have an unfavorable CTC status, for a given population or cohort of subjects. In such case, it has been found that an amount of miR-203, miR-375, miR-210, miR-801, miR-141, miR-200a, miR-200b, or miR-200c essentially equal to the reference amount or within the reference range is, preferably, indicative of a subject having an unfavorable CTC status while an amount decreased relative to the reference range is indicative for a subject ss having a favorable CTC status.

In a more preferred embodiment of the method for determining the CTC status in a subject, the amount of miRNA and the reference amount are determined in a sample of a body fluid, preferably blood, plasma, serum, saliva, or a fluid obtainable from the breast glands, more preferably plasma processed as detailed herein below and the reference amounts are, preferably, those which represent the maximal value of the sum of the method's sensitivity and specificity levels as specified by the ROC curve which is obtained for the comparison of a given population of cohort of subjects known to have an unfavorable CTC status with a given population of cohort of subjects known to have a favorable CTC status. Also preferably, the reference amounts lie within the range of values that represent a sensitivity of at least 75% and a specificity of at least 75%, or a sensitivity of at least 80% and a specificity of at least 60%, or a sensitivity of at least 85% and a specificity of at least 50%, or a sensitivity of at least 90% and a specificity of at least 45%.

The present invention also relates to a method for recommending a breast cancer therapy to a subject comprising first diagnosing breast cancer in a subject by a method described herein, followed by the further step of recommending a breast cancer therapy to the subject if breast cancer has been diagnosed.

The method for recommending a breast cancer therapy may comprise steps in addition to those explicitly mentioned above. For example, further steps may relate, e.g., to isolating miRNAs from a sample, to the additional determination of other markers, to the use of an automatic device in the determination steps, or to the diagnosis of breast cancer prior to applying the method.

As used herein, the term "herapy" refers to all measures applied to a subject to ameliorate the diseases or disorders referred to herein or the symptoms accompanied therewith to a significant extent. Said therapy as used herein also includes measures leading to an entire restoration of the health with respect to the diseases or disorders referred to herein. It is to be understood that therapy as used in accordance with the present invention may not be effective in all subjects to be treated. However, the term shall require that a statistically significant portion of subjects being afflicted with a disease or disorder referred to herein can be successfully treated. Whether a portion is statistically significant can be determined without further ado by the person skilled in the art using various well known statistic evaluation tools discussed herein above.

The term "breast cancer therapy", as used herein, relates to applying to a subject afflicted with breast cancer, including metastasizing breast cancer, measures to remove cancer cells from the subject, to inhibit growth of cancer cells, to kill cancer cells, or to cause the body of a patient to inhibit the growth of or to kill cancer cells. Preferably, breast cancer therapy is chemotherapy, anti-hormone therapy, targeted therapy, immunotherapy, or any combination thereof. It is, however, also envisaged that the cancer therapy is radiation therapy or surgery, alone or combination with other therapy regimens. It is understood by the skilled person that the selection of the breast cancer therapy depends on several factors, like age of the subject, tumor staging, and receptor status of tumor cells. It is, however, also understood by the person skilled in the art, that the selection of the breast cancer therapy can be assisted by the methods of the present invention: if, e.g. BC is diagnosed by the method for diagnosing BC, but no MBC is diagnosed by the method for diagnosing MBC, surgical removal of tumor may be sufficient. If, e.g. BC is diagnosed by the method for diagnosing BC and MBC is diagnosed by the method for diagnosing MBC, therapy measures in addition to surgery, e.g. chemotherapy and/or targeted therapy, may be appropriate. Likewise, if, e.g. BC is diagnosed by the method for diagnosing BC, and an unfavorable CTC status is determined by the method for determining the CTC status, e.g. a further addition of immunotherapy to the therapy regimen may be required.

As used herein, the term "chemotherapy" relates to treatment of a subject with an antineoplastic drug. Preferably, chemotherapy is a treatment including alkylating agents (e.g. cyclophosphamide), platinum (e.g. carboplatin), anthracyclines (e.g. doxorubicin, epirubicin, idarubicin, or daunorubicin) and topoisomerase II inhibitors (e.g. etoposide, irinotecan, topotecan, camptothecin, or VP16), anaplastic lymphoma kinase (ALK)-inhibitors (e.g. Crizotinib or AP26130), aurora kinase inhibitors (e.g. N-[4-[4-(4-Methylpiperazin-1-yl)-6-((5-methyl-1H-pyrazol-3-yl)amino]pyrimidin-2-yl]sulfanylphenyl)cyclopropanecarboxamide (VX-680)), antiangiogenic agents (e.g. Bevacizumab), or lodine131-1-(3-iodobenzyl)guanidine (therapeutic metaiodobenzylguanidine), histone deacetylase (HDAC) inhibitors, alone or any suitable combination thereof. It is to be understood that chemotherapy, preferably, relates to a complete cycle of treatment, i.e. a series of several (e.g. four, six, or eight) doses of antineoplastic drug or drugs applied to a subject separated by several days or weeks without such application.

The term "anti-hormone therapy" relates to breast cancer therapy by blocking hormone receptors, e.g. estrogen receptor or progesterone receptor, expressed on tumor cells, or by blocking the biosynthesis of estrogen. Blocking of hormone receptors can preferably be achieved by administering compounds. e.g. tamoxifen, binding specifically and thereby blocking the activity of said hormone receptors. Blocking of estrogen biosynthesis is preferably achieved by administration of aromatase inhibitors like, e.g. anastrozole or letrozole. It is known to the skilled artisan that anti-hormone therapy is only advisable in cases where tumor cels are expressing hormone receptors.

The term "targeted therapy", as used herein, relates to application to a patient a chemical substance known to block growth of cancer cells by interfering with specific molecules known to be necessary for tumorigenesis or cancer or cancer cell growth. Examples known to the skilled artisan are small molecules like, e.g. PARP-inhibitors (e.g. Iniparib), or monoclonal antibodies like, e.g., Trastuzumab.

The term "immunotherapy" as used herein relates to the treatment of cancer by modulation of the immune response of a subject Said modulation may be inducing, enhancing, or suppressing said immune response. The term "cell based immunotherapy" relates to a breast cancer therapy comprising application of immune cells, e.g. T-cells, preferably tumor-specific NK cells, to a subject.

The terms "radiation therapy" or "radiotherapy" is known to the skilled artisan. The term relates to the use of ionizing radiation to treat or control cancer. The skilled person also knows the term "surgery", relating to operative measures for treating breast cancer, e.g. excision of tumor tissue.

In a preferred embodiment, the miRNAs of the present invention are used for diagnosing breast cancer, i.e., preferably, the amount of said miRNAs is determined and the value obtained is compared to a reference amount as specified herein above. Measuring the amount of a miRNA is preferably accomplished by, e.g., quantitative real-time PCR (qRT-PCR), or mass spectrometry.

In another preferred embodiment, the amount of miRNAs of the present invention is determined using a detection agent. As used herein, the term "detection agent" relates to an agent specifically interacting with, and thus recognizing, a miRNA of the present invention. Preferably, said detection agent is a polynucleotide or an oligonucleotide. Preferably, the detection agent is labeled in a way allowing detection of said detection agent by appropriate measures. Labeling can be done by various techniques well known in the art and depending of the label to be used. Preferred labels to be used are fluorescent labels comprising, inter alia, fluorochromes such as fluorescein, rhodamin, or Texas Red. However, the label may also be an enzyme or an antibody. It is envisaged that an enzyme to be used as a label will generate a detectable signal by reacting with a substrate. Suitable enzymes, substrates and techniques are well known in the art. An oligonucleotide to be used as label may specifically recognize a target molecule which can be detected directly (e.g., a target molecule which is itself fluorescent) or indirectly (e.g., a target molecule which generates a detectable signal, such as an enzyme). The labeled detection agents of the sample will be contacted to the sample to allow specific interaction of the labeled detection agent with the miRNAs in the sample. Washing may be required to remove nonspecifically bound detection agent which otherwise would yield false values. After this interaction step is complete, a researcher will place the detection device into a reader device or scanner. A device for detecting fluorescent labels, preferably, consists of some lasers, preferably a special microscope, and a camera. The fluorescent labels will be excited by the laser, and the microscope and camera work together to create a digital image of the sample. These data may be then stored in a computer, and a special program will be used, e.g., to subtract out background data. The resulting data are, preferably, normalized, and may be converted into a numeric and common unit format. The data will be analyzed to compare samples to references and to identify significant changes. It is to be understood that the labeled detection agent need not necessarily detect the specific miRNA molecule isolated from the sample; the detection agent may also detect the amplification product obtained from said miRNA molecule, e.g., preferably, by PCR, qPCR, or qRT-PCR.

It is, however, also envisaged that the detection agent is used without a label. Preferably, the detection agent is bound to a solid surface and the sample, comprising miRNAs from a sample which have been labeled are contacted to with said surface-bound detection agent.

The present invention further relates to the use of at least one miRNA selected from the group consisting of: miR-801, miR-376c, miR-409-3p, miR-148b, miR-203, miR-142-3p, miR-141, miR-200a, miR-200b, miR-200c, miR-210, miR-375, miR-768-3p, miR-127-3p, miR-376a, and miR-652 in a sample of a subject suspected to be afflicted with breast cancer or a detection agent which specifically detects said at least one miRNA for diagnosing breast cancer. Preferably, the miRNA is selected from the list consisting of miR-801, miR-376c, miR-409-3p, miR-148b, miR-203, miR-142-3p, miR-768-3p, miR-127-3p, miR-376a, and miR-652.

The present invention also relates to the use of at least one miRNA selected from the group consisting of: miR-801, miR-376c, miR-409-3p, miR-148b, miR-203, miR-142-3p, miR-141, miR-200a, miR-200b. miR-200c, miR-210, miR-375 miR-768-3p, miR-127-3p, miR-376a, and miR-652 in a sample of a subject suspected to be afflicted with breast cancer or a detection agent which specifically detects said at least one miRNA for recommending a breast cancer therapy. Preferably, the miRNA is selected from the list consisting of miR-801, miR-376c, miR-409-3p, miR-148b, miR-203, miR-142-3p, miR-768-3p, miR-127-3p, miR-376a, and miR-652.

The present invention further relates to the use of at least one miRNA selected from the group consisting of: miR-141, miR-142-3p, miR-200a, miR-200b, miR-200c, miR-203, miR-210, miR-375, miR-768-3p, and miR-801, in a sample of a subject suspected or known to be afflicted with breast cancer or a detection agent which specifically detects said at least one miRNA for diagnosing metastasizing breast cancer or for determining the CTC status of a subject. Preferably, the miRNA is selected from the list consisting of miR-801, miR-376c, miR-409-3p, miR-148b, miR-203, miR-142-3p, and miR-768-3p. More preferably, the miRNA is selected from the list consisting of miR-801, miR-203, miR-142-3p, and miR-768-3p.

The present invention also relates to a device for diagnosing breast cancer comprising: (a) an analyzing unit comprising a detection agent for determining the amount of at least one miRNA selected from the group consisting of: miR-801, miR-376c, miR-409-3p, miR-148b, miR-203, miR-142-3p, miR-141, miR-200a, miR-200b, miR-200c, miR-210, miR-375, miR-768-3p, miR-127-3p, miR-376a, and miR-652 in a sample of a subject suspected to be afflicted with breast cancer; and (b) an evaluation unit comprising a data processor having tangibly embedded an algorithm for carrying out a comparison of the amount determined by the analyzing unit with a reference and which is capable of generating an output file containing a diagnosis established to based on the said comparison. More preferably, the mIRNA is selected from the list consisting of miR-801, miR-376c, miR-409-3p, miR-148b, miR-203, miR-142-3p, miR-768-3p, miR-127-3p, miR-376a, and miR-652.

The present invention further relates to a device for diagnosing metastasizing breast cancer or for determining the CTC status of a subject comprising: (a) an analyzing unit comprising a detection agent for determining the amount of at least one miRNA selected from the group consisting of: miR-141, miR-200a, miR-200b, miR-200c, miR-203, miR-210, miR-375, miR-142-3p, miR-768-3p, and miR-801 in a sample of a subject suspected to be afflicted with breast cancer; and (b) an evaluation unit comprising a data processor having tangibly embedded an algorithm for carrying out a comparison of the amount determined by the analyzing unit with a reference and which is capable of generating an output file containing a diagnosis established based on the said comparison. More preferably, the miRNA is selected from the list consisting of miR-801, miR-203, miR-142-3p, and miR-768-3p.

The term "device" as used herein relates to a system of means comprising at least the aforementioned means operatively linked to each other as to allow the diagnosis. Preferred means for determining the amount of the miRNAs of the present invention, and means for carrying out the comparison are disclosed above in connection with the methods of the invention. How to link the means in an operating manner will depend on the type of means included into the device. For example, where means for automatically determining the amount of the miRNAs of the present invention are applied, the data obtained by said automatically operating means can be processed by, e.g., a computer program in order to establish a diagnosis. Preferably, the means are comprised by a single device in such a case. Said device may accordingly include an analyzing unit for the measurement of the amount of the miRNAs of the present invention in a sample and an evaluation unit for processing the resulting data for the diagnosis. Preferred means for detection are disclosed in connection with embodiments relating to the methods of the invention above. In such a case, the means are operatively linked in that the user of the system brings together the result of the determination of the amount and the diagnostic value thereof due to the instructions and interpretations given in a manual. The means may appear as separate devices in such an embodiment and are, preferably, packaged together as a kit. The person skilled in the art will realize how to link the means without further inventive skills. Preferred devices are those which can be applied without the particular knowledge of a specialized clinician, e.g., test stripes or electronic devices which merely require loading with a sample. The results may be given as output of parametric diagnostic raw data, preferably, as absolute or relative amounts. It is to be understood that these data will need interpretation by the clinician. However, also envisaged are expert system devices wherein the output comprises processed diagnostic raw data the interpretation of which does not require a specialized clinician. Further preferred devices comprise the analyzing units/devices (e.g., biosensors, arrays, solid supports coupled to ligands specifically recognizing the miRNAs of the present invention, Plasmon surface resonance devices, NMR spectro-meters, mass-spectrometers etc.) or evaluation units/devices referred to above in accordance with the methods of the invention.

The present invention further relates to a kit for carrying out a method for diagnosing BC, wherein said kit comprises instructions for carrying out said method, a detection agent for determining the amount of at least one miRNA selected from the group consisting of: miR-801, miR-376c, miR-409-3p, miR-148b, miR-203, miR-142-3p, miR-141, miR200a, miR-200b, miR-200c, miR-210, miR-375, miR-768-3p, miR-127-3p, miR-376a, and miR-652 in a sample of a subject suspected to be afflicted with breast cancer, and standards for a reference. Preferably, the miRNA is selected from the list consisting of miR-801, miR-376c, miR-409-3p, miR-148b, miR-203, miR-142-3p, miR-768-3p, miR-127-3p, miR-376a, and miR-652.

The present invention also relates to a kit for carrying out a method for diagnosing MBC or for determining the CTC status in a subject, wherein said kit comprises Instructions for carrying out said method, a detection agent for determining the amount of at least one miRNA selected from the group consisting of: miR-141, miR-200a, miR-200b, miR-200c, miR-203, miR-210, miR-375, miR-142-3p, miR-768-3p, and miR-801 in a sample of a subject suspected to be afflicted with metastatic breast cancer, and standards for a reference. Preferably, the miRNA is selected from the list consisting of miR-801, miR-203, miR-142-3p, and miR-768-3p.

The term "kit" as used herein refers to a collection of the aforementioned compounds, means or reagents of the present invention which may or may not be packaged together. The components of the kit may be comprised by separate vials (i.e. as a kit of separate parts) or provided in a single vial. Moreover, it is to be understood that the kit of the present invention is to be used for practicing the methods referred to herein above. It is, preferably, envisaged that all components are provided in a ready-to-use manner for practicing the methods referred to above. Further, the kit preferably contains instructions for carrying out the said methods. The instructions can be provided by a user's manual in paper- or electronic form. For example, the manual may comprise instructions for interpreting the results obtained when carrying out the aforementioned methods using the kit of the present invention.

Also, the present invention relates to a method for diagnosing a breast tumor in a subject comprising the steps of: (a) determining in a sample of a subject suspected to be afflicted with breast tumor the amount of at least one miRNA or the amounts of at least the miRNAs of a combination of miRNAs selected from the group consisting of: (i) miR-148b, (ii) miR-652, (iii) miR-801, (iv) miR-148b and miR 652, (v) miR-148b and miR-801, (vi) miR-652 and miR-801, and (vii) miR-148b, miR-652, and miR-801; and (b) comparing said amount with a reference or comparing said amounts with references, whereby a breast tumor is to be diagnosed.

As used herein, the term "breast tumor" relates to an abnormal hyperproliferation of breast tissue cells in a subject, which may be a benign (non-cancerous) tumor or a malign (cancerous) tumor. Benign breast tumors, preferably, include fibroadenomas, granular cell tumors, intraductal papillomas, and phyllodes tumors. A malign tumor, preferably, is a breast cancer as specified herein above.

The present invention also relates to a method of determining treatment success in a subject afflicted with metastatic breast cancer, comprising (a) determining in a sample of a subject receiving or having received treatment against metastasizing breast cancer the amount of at least one miRNA selected from the group consisting of: miR-801, miR-141, miR-200a, miR-200b, miR-200c, miR-203, miR-210, and miR-375; and (b) comparing said amount with a reference or comparing said amounts with references, thereby determing treatment success.

The term "treatment success", as used herein, preferably relates to an amelioration of the diseases or disorders referred to herein or the symptoms accompanied therewith to a significant extent. More preferably, the term relates to a complete cure of said subject, i.e. to the prevention of progression and/or relapse of metastasizing breast cancer for at least five years. Accordingly, "determining treatment success" relates to assessing the probability according to which a subject was successfully treated. Preferably, the term relates to predicting progression free survival and/or overall survival of the subject, more preferably for a specific period of time. The term "predicting progression free survival" relates to determining the probability of a subject surviving without relapse and/or progression of metastatic breast cancer for a specific period of time. Accordingly, the term "predicting overall survival" relates to determining the probability according to which a subject will survive for a specific period of time. Preferably, said period of time is at least 12 months, more preferably at least 24 months.

It is understood by the skilled person that the reference used in the method of determining treatment success is a specific reference, which may be different from the references used in the other methods of the present invention. Also, the skilled person knows how to obtain a suitable reference according to the methods specified herein above. Preferably, the reference is derived from a sample of the same subject obtained before treatment. More preferably, the reference is derived from one or more subjects known to have successfully been treated. Alternatively, the reference may be derived from one or more subjects known to have not successfully been treated. Most preferably, the reference corresponds to the lower tertile, lower quartile, lower fifth, or lower sixth of values obtained from a cohort of individuals after having been received treatment against metastasizing breast cancer.

Preferably, the method of determining treatment success according to the present invention comprises determining the aforesaid miRNA or miRNAs in a sample of a subject receiving treatment, i.e. in a sample obtained from a subject receiving treatment at the time the sample is obtained. It is understood by the skilled person that a subject receiving treatment, preferably, is a subject having received the first dose of active principle and/or surgery at least one day, more preferably at least one week, even more preferably at least two weeks, or, most preferably, at least one month before the sample is obtained. More preferably, the method of determining treatment success according to the present invention comprises determining the aforesaid miRNA or miRNAs in a sample of a subject having received at least one treatment cycle, most preferably a complete treatment cycle.

All references cited in this specification are herewith incorporated by reference with respect to their entire disclosure content and the disclosure content specifically mentioned in this specification.

BRIEF DESCRIPTION OF THE DRAWINGS

FIGS. 1 to 6 show data obtained from patient cohort I, whereas

FIG. 1: Circulating miRNAs validated as being upregulated in the plasma of breast cancer patients compared to healthy controls. Box and whisker plots of cel-miR-39 normalized Ct values for miR-148b (A), miR-376c (B), miR-409-3p (C) and miR-801 (D) with their corresponding two-sided Wilcoxon rank sum test p-values.

FIG. 2: Evaluation of the diagnostic potential of miR-148b. miR-376c, miR-409-3p and miR-801 in the plasma of breast cancer patients. (A-D) ROC curves of logistic regression models for individual miRNAs miR-148b, miR-376c, miR-409-3p and miR-801. (E) A combined ROC curve of the logistic regression model for the least redundant and most informative diagnostic panel consisting of miR-148b, miR-409-3p and miR-801 with their corresponding area under the curve (AUC) values.

FIG. 3: Expression of miR-148b, miR-376c, miR-409-3p and miR-801 in benign versus malignant breast tissue. Box and whisker plots with RNU6B normalized relative expression levels of miR-148b (A), miR-376c (B), miR-409-3p (C) and miR-801 (D) in benign and malignant breast tissue with their corresponding two-sided Wilcoxon rank sum test p-values.

FIG. 4: Validation of candidate miRNAs. (A) Box and whisker plots of the expression of 10 candidate miRNAs, represented as Ct values, across 61 CTC-positive, 72 CTC-negative MBC cases and 76 controls. (B) Spearman partial correlations between miRNAs based on their expression with the corresponding correlations values depicted along the lines (p<0.00001 for all miR pairs that are connected by lines).

FIG. 5: ROC analysis. (A-E) Leave-one-out cross-validated ROC curves for logistic regression models based on individual miRNAs for all three comparisons. (F-H) Leave-one-out cross-validated ROC curves for multiparametric panel based on penalised LASSO logistic regression model. (F) CTC-positive vs CTC-negative: miR-141, miR-200b, miR-142-3p, miR-768-3p (83% specificity at 80% sensitivity); (G) CTC-positive vs control: miR-141, miR-200b, miR-200c, miR-210, miR-375, miR-801, miR-142-3p, miR-768-3p (91% specificity at 90% sensitivity); (H) CTC-negative vs control: miR-141, miR-200b, miR-200c, miR-210, miR-375, miR-203, miR-801, miR-142-3p, miR-768-3p (65% specificity at 80% sensitivity). AUC-Area under the curve FIG. 6: Kaplan-Meier curves of each miRNAs (miR-141, miR-200a, miR-200b, miR-200c, miR-203, miR-210, miR-375, and miR-801) for progression free survival (PFS) (A-H) and overall survival (OS) (I-P). Stratified curves are shown for two groups lower quartile, and upper three quartiles. Kaplan-Meier curves show that lower the Ct value, i.e., higher the expression of the miRNA, lower is the probability of progression-free, and overall survival.

FIG. 7: Wilcoxon rank sum tests with continuity correction confirmed that miR-127-3p (p<0.001), miR-148b (p<0.0001), miR-376a (p=0.03), miR-376c (p=0.03), mIR-409-3p (p=0.005), miR-652 (p<0.0001) and miR-801 (p<0.0001) were significantly upregulated in breast cancer patients compared to healthy controls as shown in box and whisker plots with Ct values for these circulating miRNAs. Box and whisker plots of Ct values for miR-148b (p=0.02), miR-652 (p=0.01) and miR-801 (p=0.003) demonstrate that these miRNAs are upregulated in the plasma of benign breast tumor patients compared to healthy controls as well.

FIG. 8: Evaluation of the diagnostic potential of miR-127-3p, miR-148b, miR-376a, miR-376c, miR-409-3p, miR-652 and miR-801 in the plasma of patients with breast tumors. ROC curves of logistic regression models for individual circulating miRNAs miR-127-3p, miR-148b, miR-376a, miR-376c, miR-409-3p, miR-652 and miR-801 show potential to discriminate between healthy controls and breast tumor patients with area under the curve (AUC) values of up to 0.75 (A-G). A combined ROC curve of the logistic regression model for the combination of al seven aforementioned circulating miRNAs for women of all ages (H) or only those up to 50 years of age (I), indicate good discriminatory potential with AUC values of 0.81 and 0.86, respectively.

FIG. 9: Expression of miR-127-3p, miR-376a and miR-652 in benign versus malignant breast tissue. Box and whisker plots with RNU6B normalized relative expression levels of miR-127-3p (A) and miR-652 (B) in benign and malignant breast tissue with the corresponding two-sided Wilcoxon rank sum test p-values for A-C. Due to low miR-376a levels in the investigated tissue samples the normalization strategy was not applicable and un-normalized Ct values are presented for miR-376a (C).

Figure 2:
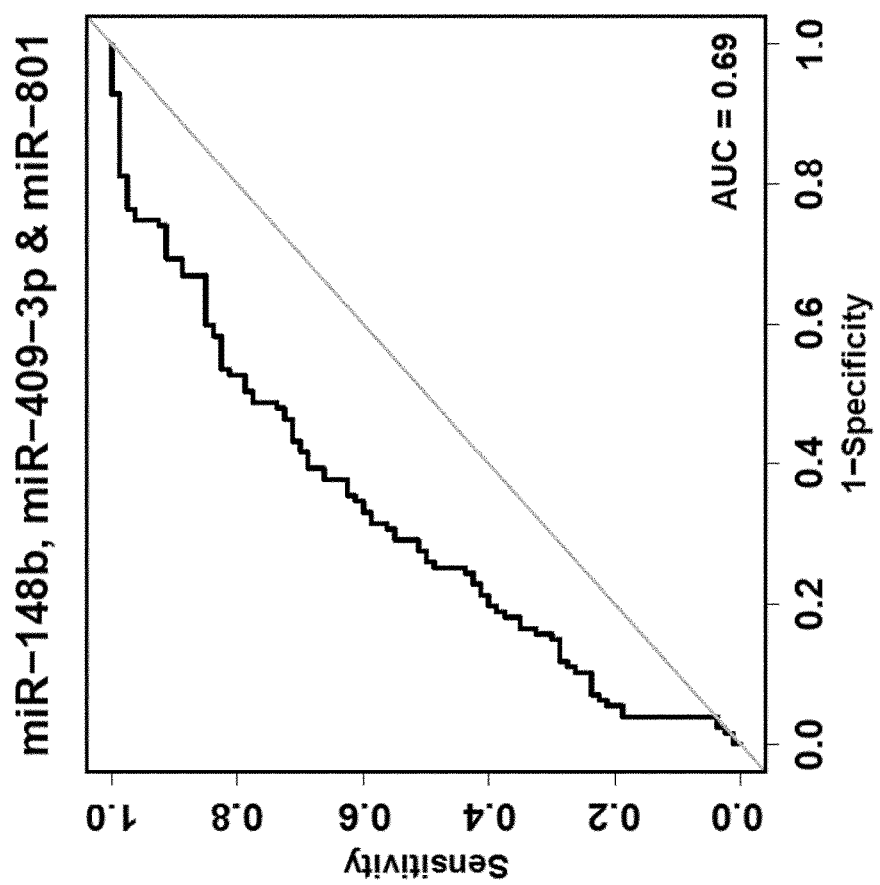

The following Examples shall merely illustrate the invention. They shall not be construed, whatsoever, to limit the scope of the invention.

EXAMPLES

I. Cohort I

Example 1: Breast Cancer Patients and Healthy Controls

This study was approved by the Ethical Committee of the Medical Faculty in Heidelberg. For cohort I, blood samples were collected from 133 female metastatic breast cancer patients, 127 female primary breast cancer patients and 80 healthy female volunteers who served as controls. All cases and controls were Caucasian. In metastatic breast cancer patients, circulating tumour cells (CTC) were enumerated by evaluating it with the CellSearch® system (Veridex, LLC, Raritan, N.J.). Based on the CTC numbers, patients were classified as CTC-positive (≥5 intact CTCs/7.5 ml blood) or CTC-negative (no intact, apoptotic or enucleated CTCs). Patients had received one or more lines of therapy for their metastatic disease prior to enrolment into the study. For primary breast cancer patients, blood samples were collected at the time-point of diagnosis before they underwent any therapeutic procedures, such as surgery, radiation or systemic therapy. Patient histopathology results were confirmed by surgical resection of the tumors and clinico-pathological features defined by operative findings. For neoadjuvant primary breast cancer patients, histopathological characteristics and tumor stage were assessed based on histobiopsy results and imaging techniques. Control blood samples were collected from healthy women with no history of malignant diseases, no blood donations received in the previous 3 years and no reported current inflammatory condition based on self-report. Malignant tissue samples were collected from non-neoadjuvant primary breast cancer patients (n=24) during surgery. They were snap-frozen in liquid nitrogen and stored at −80° C. within 15 min of harvesting. For women with benign findings (n=8) tissue was collected during the diagnostic histobiopsy.

Example 2: Blood Processing and miRNA Isolation from Plasma

EDTA blood samples were collected from cases and control individuals and processed for plasma within 2 hours of collection. To avoid contamination with epithelial cells from the initial skin puncture the first blood tube collected during phlebotomy was not processed for plasma. Blood was centrifuged at 1300 g for 20 minutes at 10° C. The supernatant (plasma) was transferred into microcenlrifuge tubes followed by a second high-speed centrifugation step at 15500 g for 10 minutes at 10° C. to remove cell debris and fragments. The plasma was aliquoted into cryo vials, snap-frozen in liquid nitrogen and stored at −80° C. until use.

Total RNA (including miRNAs) was extracted from 400 µL of plasma. Denaturation and phase separation were conducted using TRIzol LS (Invitrogen, Germany) according to manufacturer's protocol, with a minor modification: 10 fmol of a *C. elegans* miR-39/miR-238 mixture was spiked-in. The aqueous phase was transferred into another tube, 1.5 volumes of absolute ethanol were added and the mixture was applied to miRNeasy Mini kit columns (Qiagen, Germany). After washing miRNAs were eluted in 30 µL of RNase-free water.

Example 3: mIRNA Profiling of Plasma with TaqMan Low Density Arrays (TLDA)

Profiling was carried out on 11 CTC positive metastatic (>20 CTCs/7.5 ml blood), 9 CTC negative metastatic, 10 early stage primary breast cancer patients and 10 healthy controls using TaqMan Low Density Arrays (Human microRNA Cards A and B v2.0) from Applied Biosystems according to manufacturer's protocol. These arrays measured the expression of 667 human miRNAs from miRBase version v. 10. In brief, a fixed volume of miRNAs (3 µl) was reverse transcribed using the TaqMan MicroRNA Reverse Transcription Kit and TaqMan MicroRNA Megaplex RT Human Pool Sets A (v2.1) & B (v2.0). cDNA was pre-amplified for 12 cycles with Megaplex PreAmp Human primer Pools A (v2.1) & B (v2.0), respectively, and loaded into the TLDA array card ports. Real-time PCR was carried out with an Applied Biosystems 7900HT thermocycler under the following conditions: 50° C. for 2 min, 94.5° C. for 10 min, followed by 40 cycles of 97° C. for 30 sec and 59.7° C. for 1 min. Raw data was exported using SDS Relative Quantification Software version 2.2.2 (Applied Biosystems) with automatic baseline and threshold settings.

Raw Ct values of the initial plasma screening step with TLDA arrays were analyzed using the statistical computational environment R version 2.11 (http://www.r-project.org/) and the R package HTqPCR from Bioconductor (v1.2.0) (R Development Core Team (2010). R: A language and environment for statistical computing. R Foundation for Statistical Computing, Vienna, Austria. ISBN 3-900051-07-0), miRNAs with Ct values smaller than 15 or larger than 35 across all the samples were filtered out from further analysis, along with all miRNAs with inter-quartile ranges IQR<1.5 (invariant miRNAs), after which quantile normalization and averaging of duplicates followed. After limma analysis to identify miRNAs that were differentially expressed between cases and controls, the results were adjusted for multiple testing by controlling the false discovery rate (FDR) according to the method of Benjamini-Hochberg (Smyth G K. Linear models and empirical bayes methods for assessing differential expression in microarray experiments. Stat Appl Genet Mol Biol 2004; 3: Article3; Benjamini Y, Hochberg Y. Controlling the False Discovery Rate: A Practical and Powerful Approach to Multiple Testing. J. Roy. Statistical Society. Series B (Methodological) 1995:57:289-301.)

Example 4: Validation of Selected Marker Candidates

Reverse transcription (RT) reactions were performed using TaqMan miRNA Reverse Transcription Kit (Applied Biosystems, Germany) and miRNA-specific RT primers for hsa-miR-141, hsa-miR-142-3p, hsa-miR-148b, hsa-miR-200a, hsa-miR-200b, hsa-miR-200c, hsa-miR-203, hsa-miR-210, hsa-miR-375, hsa-miR-376c, hsa-miR-409-3p, hsa-miR-768-3p and hsa-miR-801 (Applied Biosystems, Germany). Singleplex (primary breast cancer) or multiplex (metastatic breast cancer) reactions were carried out in a volume of 7.5 µl or 15 µl, respectively. Each reaction comprised 1×RT buffer, 1 mM dNTPs, 0.3×miRNA-specific RT primers, 0.25 U RNase inhibitor, 3.3U Multiscribe Reverse Transcriptase and a fixed volume of miRNA template (2 or 1 µl, respectively). For benign and malignant breast cancer tissue samples the reactions were carried out in 15 µl and comprised the following: 1×RT buffer, 1 mM dNTPs. 0.6×miRNA-specific and RNU6B RT primers, 0.25U RNase inhibitor, 3.3U Multiscribe Reverse Transcriptase and 5 ng RNA. Blinding of samples and a randomized, simultaneous investigation of cases and controls on reaction plates was intended to minimize bias and batch effects during validation. RT was carried out in a G-STORM GS2 PCR cycler (Alphametrix, Germany) under the following conditions: 16° C. for 30 min, 42° C. for 30 min and 85° C. for 5 min, followed by a hold at 4° C.

TaqMan real-time PCR reactions were performed in triplicates in scaled-down reactions comprising 2.5 µL TaqMan 2× Universal PCR Master Mix with No AmpErase UNG (Applied Biosystems, Germany), 0.25 µL 20× miRNA-specific primer/probe mix (Applied Biosystems, Germany) and 2.25 µL of the reverse transcription product (diluted 1:4). Real-time PCR was carried out in a LightCycler 480 thermocycler (Roche, Germany) under the following conditions: 95° C. for 10 min, then 50 cycles of 95° C. for 15 s, 60° C. for 30 s and 72° C. for 30 s, followed by a hold at 4° C.

Raw data from validation studies in blood plasma was normalized to spiked-in cel-miR-39 as described in Kroh et al. (Kroh E M, Parkin R K, Mitchell P S, Tewari M. Analysis of circulating microRNA biomarkers in plasma and serum using quantitative reverse transcription-PCR (qRT-PCR). Methods 2010; 50:298-301). Raw Ct values from breast tissue samples were normalized to RNU6B as described in User Bulletin #2: ABI PRISM 7700 Sequence Detection System (Applied Biosystems).

Example 5: Comparison of Early Breast Cancer Cases with Controls

Wilcoxon rank sum tests with continuity correction were used to identify miRNAs that were differentially expressed between cases and controls in the validation set (127 primary breast cancer patients and 80 controls). To evaluate the breast cancer detection potential, receiver operating characteristic (ROC) curves were constructed and the areas under the curves (AUC) calculated. Based on ROC curves with 95% confidence intervals, lowest specificities at pre-defined sensitivities (75% to 90%) were computed for the most informative and least redundant model of miRNAs. Based on ROC curves, lowest specificities at pre-defined sensitivities (75% to 90%) were computed for the most informative and least redundant model of miRNAs as the lower bounds of the 95% confidence intervals (Tom Fawcett (2006) "An introduction to ROC analysis". Pattern Recognition Letters 27, 861-874. DOI: 10.1016/j.patrec.2005.10.010; using R package pROC v1.3.2).

Example 6: Comparison of Metastatic Breast Cancer Cases (CTC Positive and CTC Negative) with Controls Wilcoxon rank sum tests were applied to assess the significance of differences between the CTC positive and CTC negative, CTC positive and controls, and, CTC negative and controls. Leave-one-out cross-validated receiver operating characteristic (ROC) curves were built for logistic regression models based on individual mIRNAs. Penalised LASSO logistic regression model (with penalty parameter tuning performed by 10-fold cross-validation) was used to compute the least redundant and most informative panel of miRNAs that can discriminate two groups. Corresponding area under the curve (AUC) was calculated for each model. Based on ROC curves with 95% confidence intervals, lowest specificities at pre-defined sensitivities (75% to 90%) were computed for the most informative and least redundant model of miRNAs.

Example 7: miRNA Profiling Revealed Putative Marker Candidates for Breast Cancer Detection in Plasma In an initial screening step using TLDA arrays we analyzed plasma miRNA profiles of 10 early stage breast cancer patients as well as 10 healthy controls. The patients all had an invasive ductal carcinoma, which was ER/PR+ and HER2− with an AJCC TNM stage I or II (Hayes D F, Allred C, Anderson B O, Ashley P, Barlow W, Berry D, Carlson R W, Gelman R, Hilsenbeck S, Hortobagyi G N, Kattan M, Lester S C et al. Breast cancer. In: Edge S B, Byrd D R, Compton C C, Fritz A G, Greene F L, Trotti A. AJCC cancer staging manual (seventh edition). New York: Springer, 2010: 345-376.). Patients were age-matched to healthy controls. The mean and median ages of patients were 54 and 51 years respectively, while they were 53 and 54.5 years for controls.

After filtering, normalization of raw array data and averaging of duplicates (as described in Example 3 above) a total of 139 variant miRNAs remained for statistical analysis. A heat map of the results of hierarchical cluster analysis of the correlations across samples and principal components analysis identified one control sample as an outlier, which was then removed from further statistical analysis. Limma analysis revealed 13 circulating miRNAs with statistically significant differences in expression between cases and controls before adjustment for multiple testing. Seven miRNAs were downregulated (miR-139-3p, miR-193a-3p, miR-206, miR-519a, miR-526b*, miR-571c and miR-571) and six upregulated (miR-148b, miR-184, miR-376c, miR-409-3p, miR-424 and miR-801) in the plasma of early stage breast cancer patients. A list of these miRNAs can be found in Table 1 together with their (i) p-values, (ii) p-values adjusted for multiple testing according to the method of Benjamini-Hochberg (indicating false discovery rates, FDRs), (iii) mean Ct values for both investigated groups and (iv) differences in mean Ct values (ΔCt) between the control and cases group

TABLE 1

Circulating miRNAs differentially expressed in the plasma of early stage breast cancer cases compared to healthy controls in TLDA array analysis.

| miRNA | p-value | adj. p-value (FDR) | mean Ct (controls) | mean Ct (cases) | ΔCt* |
|---|---|---|---|---|---|
| hsa-miR-571 | <0.001 | 0.095 | 30.4 | 37.9 | −7.42 |
| hsa-miR-801 | 0.002 | 0.155 | 30.8 | 28.5 | 2.24 |
| hsa-miR-139-3p | 0.007 | 0.259 | 29.8 | 34.9 | −5.06 |
| hsa-miR-376c | 0.008 | 0.259 | 31.9 | 30.5 | 1.47 |
| hsa-miR-193a-3p | 0.009 | 0.259 | 38.3 | 40.0 | −1.71 |
| hsa-miR-424 | 0.014 | 0.282 | 38.3 | 35.3 | 3.06 |
| hsa-miR-409-3p | 0.013 | 0.282 | 33.8 | 32.3 | 1.56 |
| hsa-miR-184 | 0.019 | 0.304 | 39.4 | 36.6 | 2.75 |
| hsa-miR-206 | 0.020 | 0.304 | 30.1 | 31.7 | −1.61 |
| hsa-miR-148b | 0.027 | 0.376 | 31.7 | 30.6 | 1.02 |
| hsa-miR-526b* | 0.032 | 0.407 | 36.6 | 38.6 | −2.00 |
| hsa-miR-519a | 0.039 | 0.447 | 35.8 | 38.1 | −2.27 |
| hsa-miR-517c | 0.048 | 0.498 | 36.4 | 38.5 | −2.14 |

Candidates chosen for validation are in bold and finally validated miRNAs are underlined.
*ΔCt = mean Ctcontrols − mean Ctcases

Example 8: miR-148b, miR-376c, miR-409-3p and miR-801 are Upregulated in Plasma of Breast Cancer Patients The following criteria were applied to choose the best candidates for marker validation studies in plasma: unadjusted p<0.05 and mean Ct<33 in at least one investigated group (as miRNA expression should be stably detectable in at least one group) (Table 1). The application of these criteria resulted in seven candidates for validation: miR-139-3p, miR-148b, miR-206, miR-376c, miR-409-3p, miR-571 and miR-801.

To find the appropriate sample size necessary to detect fold changes as small as two-fold, power simulations were carried out. Statistical power was estimated based on observed standard deviations in the preliminary small-scale validation experiments. In all tested scenarios in which total sample size was ≥200 and included at least 80 controls statistical power was very high (>93%).

A total of 127 breast cancer and 80 healthy control plasma samples were analyzed for their expression of the aforementioned seven marker candidates. After a preliminary small-scale validation on 50 samples, miR-139-3p showed a clearly non-significant p-value (p=0.6⁰) and miR-571 could not be detected in either group. For these reasons, validation was continued only with the five remaining miRNAs. A comparison of case and control groups using a Wilcoxon rank sum test with continuity correction resulted in four circulating miRNAs validated as being upregulated in the plasma of breast cancer patients. These miRNAs were miR-148b (p<0.001), miR-376c (p<0.0001), miR-409-3p (p<0.0001) and miR-801 (p<0.001), whereas miR-206 (p=0.26) did not reach statistical significance (FIG. 1.A-D).

Example 9: Diagnostic Potential of miR-148b, miR-376c, miR-409-3p and miR-801 in Plasma ROC curve analysis was performed to evaluate the diagnostic potential of miR-148b, miR-376c, miR-409-3p and miR-801 for breast cancer detection in blood plasma. The discriminatory power between tumor and control samples is depicted by the areas under the curves (AUC). Individually, miR-148b had an AUC of 0.65, miR-376c of 0.66, miR-409-3p of 0.66 and miR-801 of 0.64 (FIG. 2. A-D).

We found that miR-148b, miR-376c and miR-409-3p expressions correlate to each other with Spearman rank correlation coefficients as follows (all p<0.00001): (i) ρ=0.64 between miR-148b and miR-409-3p, (ii) ρ=0.66 between miR-148b and miR-376c and (iii) ρ=0.91 between miR-376c and miR-409-3p. The correlation coefficient between miR-148b and miR-801 expressions is also considerable (ρ=0.35), but other correlations were not substantial. By investigating different combinations of miR-148b, miR-376c, miR-409-3p and miR-801 we found that a combined ROC curve with miR-148b, miR-409-3p and miR-801 gave the most informative and least redundant miRNA panel with an AUC of 0.69 (FIG. 2.E). The discriminatory power of all four significantly upregulated miRNAs (AUC=0.69) did not outperform this panel and other miRNA combinations performed only slightly poorer.

Example 10: miR-148b, miR-376c and miR-409-3p are Downregulated in Malignant Primary Breast Cancer Tissue A total of 24 primary breast cancer surgery tissue samples and 8 benign breast biopsies were analyzed for their miR-148b, miR-376c, miR-409-3p and miR-801 expression levels. A comparison of these two sample groups showed that, in contrast to plasma, miR-148b (p=0.007), miR-376c (p<0.0001) and miR-409-3p (p=0.002) were downregulated in malignant breast cancer tissue in comparison to benign breast tissue samples (FIG. 3.A-C). In the case of miR-801 (p=0.80) no significant differences in expression levels were detected (FIG. 3.D).

Example 11: Circulating miRNA Profiles of CTC-Positive and CTC-Negative MBC are Significantly Different 30 plasma samples consisting of 11 CTC-positive (CTC=20/7.5 ml blood). 9 CTC-negative cases, and 10 controls were profiled by low-density TaqMan arrays. After filtering, normalization of raw array data and averaging of duplicates (as described in Example 3 above), 216 unique and variably expressed miRNAs remained, which were used for hierarchical clustering and limma analysis. Surprisingly, we observed that the differences in profiles between CTC-positive and CTC-negative MBC patients were larger than those between CTC-negative and healthy controls. Clustering of samples revealed that CTC-positive cases formed one cluster, while CTC-negative cases and controls formed two sub-clusters of another branch. Concomitantly, limma analysis returned more miRNAs significant for the comparison of CTC-positive cases (19 miRNAs) than for CTC-negative cases (4 miRNAs) with controls. Analysis of CTC-positive against CTC-negative cases engendered 12 up- and 3 down-regulated miRNAs in the CTC-positive group. Stringent cut-offs were applied to ensure reduction in false positives and feasibility of testing (controlling the false discovery rate (FDR) according to the method of Benjamini-Hochberg at a level of 0.1) Consequently, seventeen miRNAs were selected for the validation study: miR-99a, miR-133b, miR-139-3p, miR-141, miR-1423p, miR-193b*, miR-200a, miR-200b, miR-200c, miR-203, miR-206, miR-210, miR-375, miR-571, miR-630, miR-768-3p and miR-801.

Example 12: Eight Circulating mIRNAs Significantly Upregulated in CTC-Positive MBC Compared to CTC-Negative MBC or Controls After preliminary testing, five out of the seventeen candidates (miR-133b, miR-139-3p, miR-193b*, miR-206, miR-99a) could not be analyzed due to low expression, while miR-571 and miR-630 could not be detected by TaqMan miRNA assays. The remaining ten miRNAs, including four members of the miR-200 family (miR-141, miR-200a, miR-200b, miR-200c), along with miR-142-3p, miR-203, miR-210, miR-375, miR-768-3p and miR-801, were analyzed in an expanded sample set of 133 MBC cases and 76 controls.

Figure 4:
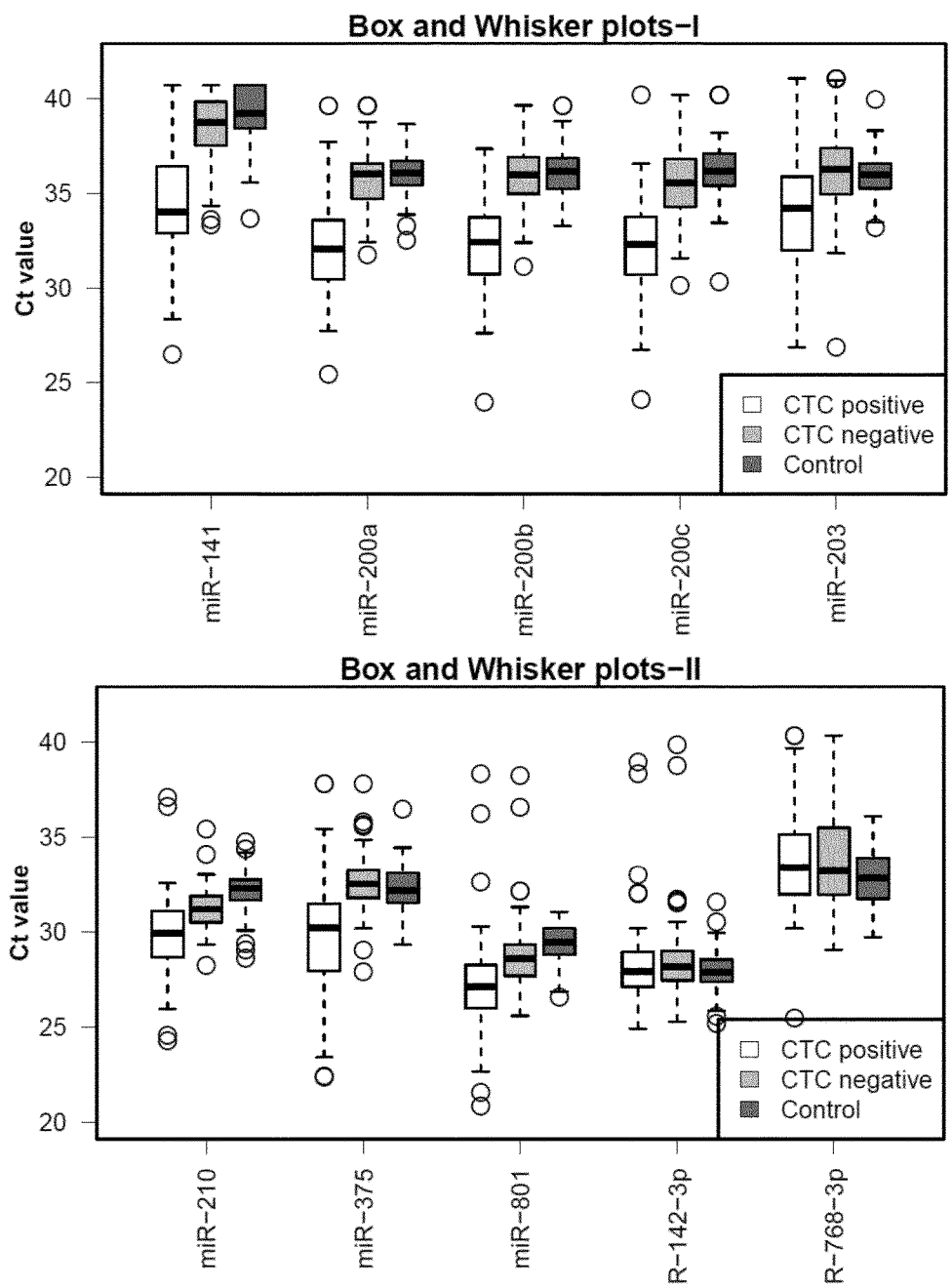
Figure 4:
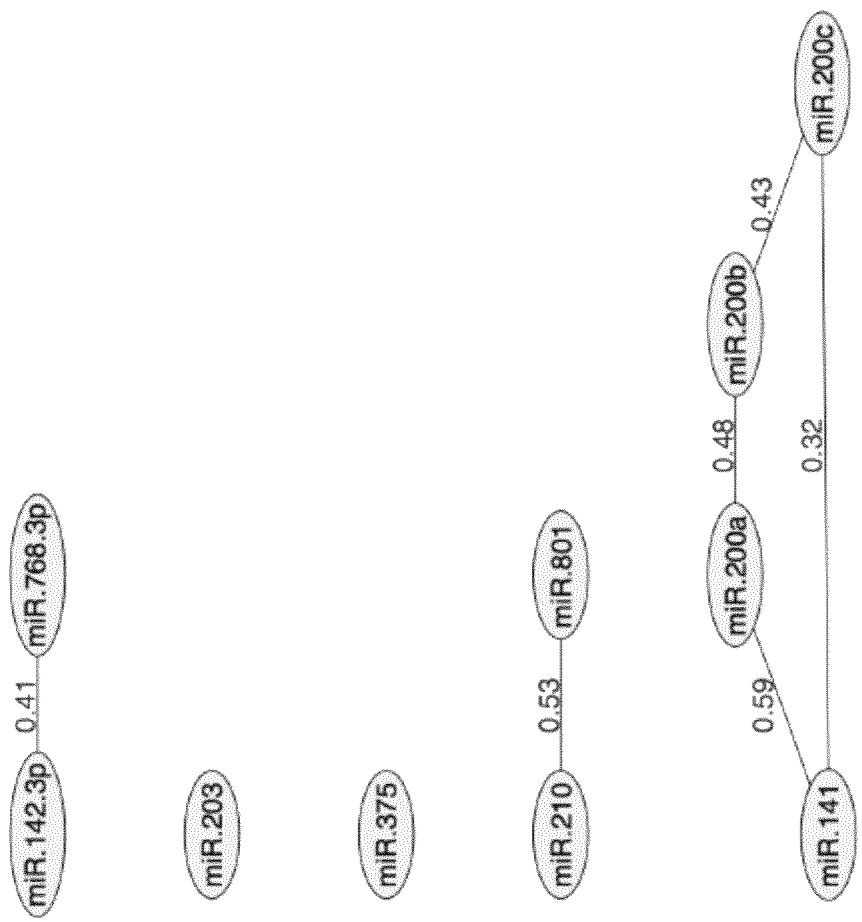

Wilcoxon rank sum tests with continuity correction confirmed that miR-141, miR-200a, miR-200b, miR-200c, miR-203, miR210, miR-375 and miR-801 were significantly upregulated in CTC-positive in comparison to CTC-negative cases (fold change (FC) of 2.41 to 26.17, p<0.00001 for all miRNAs). Based on the trend of our array results, the differences in circulating miRNAs between these subgroups and controls were additionally explored. These eight miRNAs were also found to have significantly increased expression in positive cases (FC of 3.36 to 36.25, p<0.00001 for all miRNAs). However, only four out of these eight miRNAs were significantly upregulated in CTC-negative cases (miR-141, miR-200c, miR-210, miR-801; FC of 1.39 to 2.14, p<0.05 for all miRNAs). Although miR-768-3p had only a negligible decrease when comparing CTC-positive and CTC-negative cases, it was found to be significantly downregulated in CTC-positive (p=0.006, FC=0.68), and CTC-negative cases (p=0.003, FC=0.77). No significant changes in expression were found in miR-142-3p in any of the comparisons. These results are represented in FIG. 4(A) and Table 2. Analysis of the correlation in expression of these ten miRNAs discerned a high correlation among the members of the miR-200 family (ρ>0.3, P<0.00001), between miR-210 and miR-801 (ρ=0.53, P<0.00001), and between miR-142-3p and miR-768-3p (ρ=0.41. P<0.00001) (FIG. 4(B)).

Figure 5:
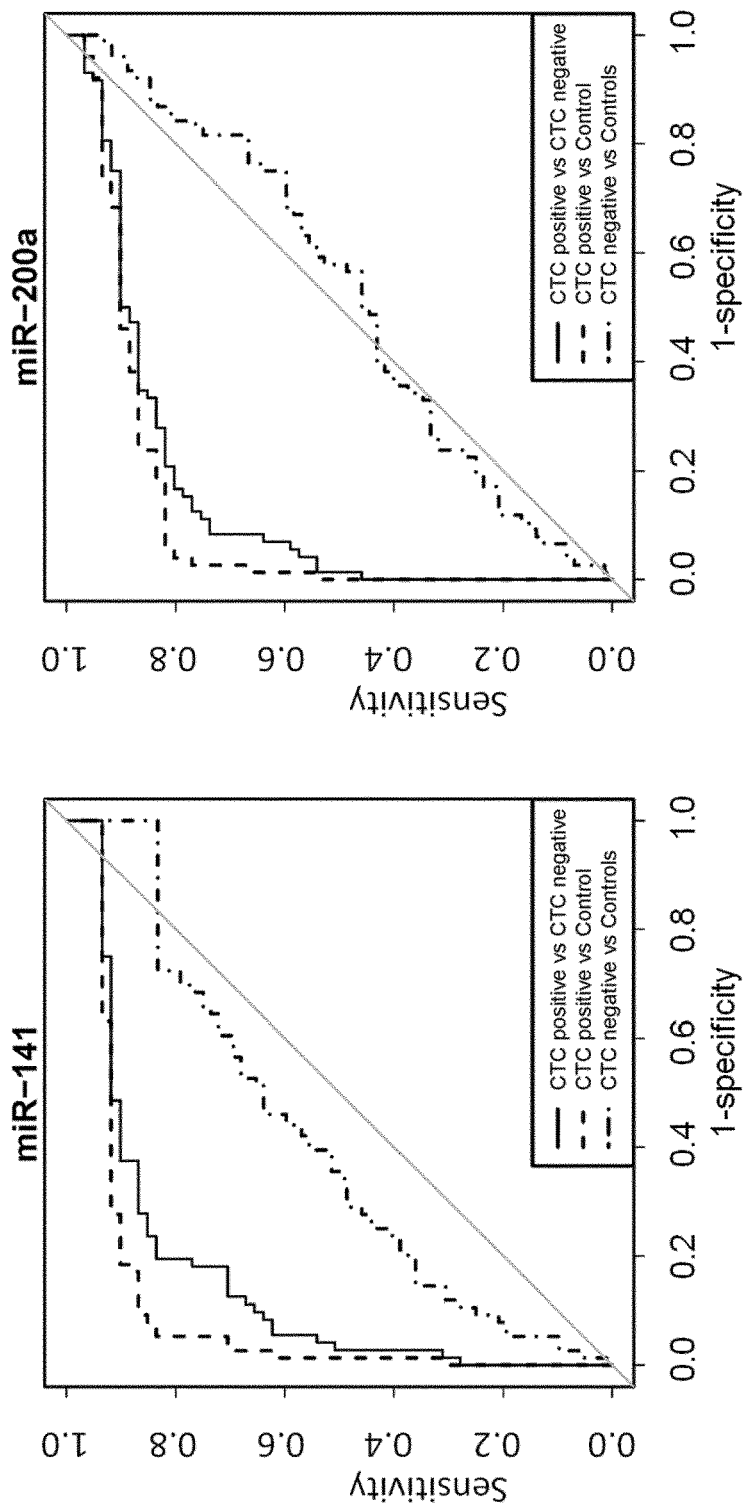
Figure 5B:
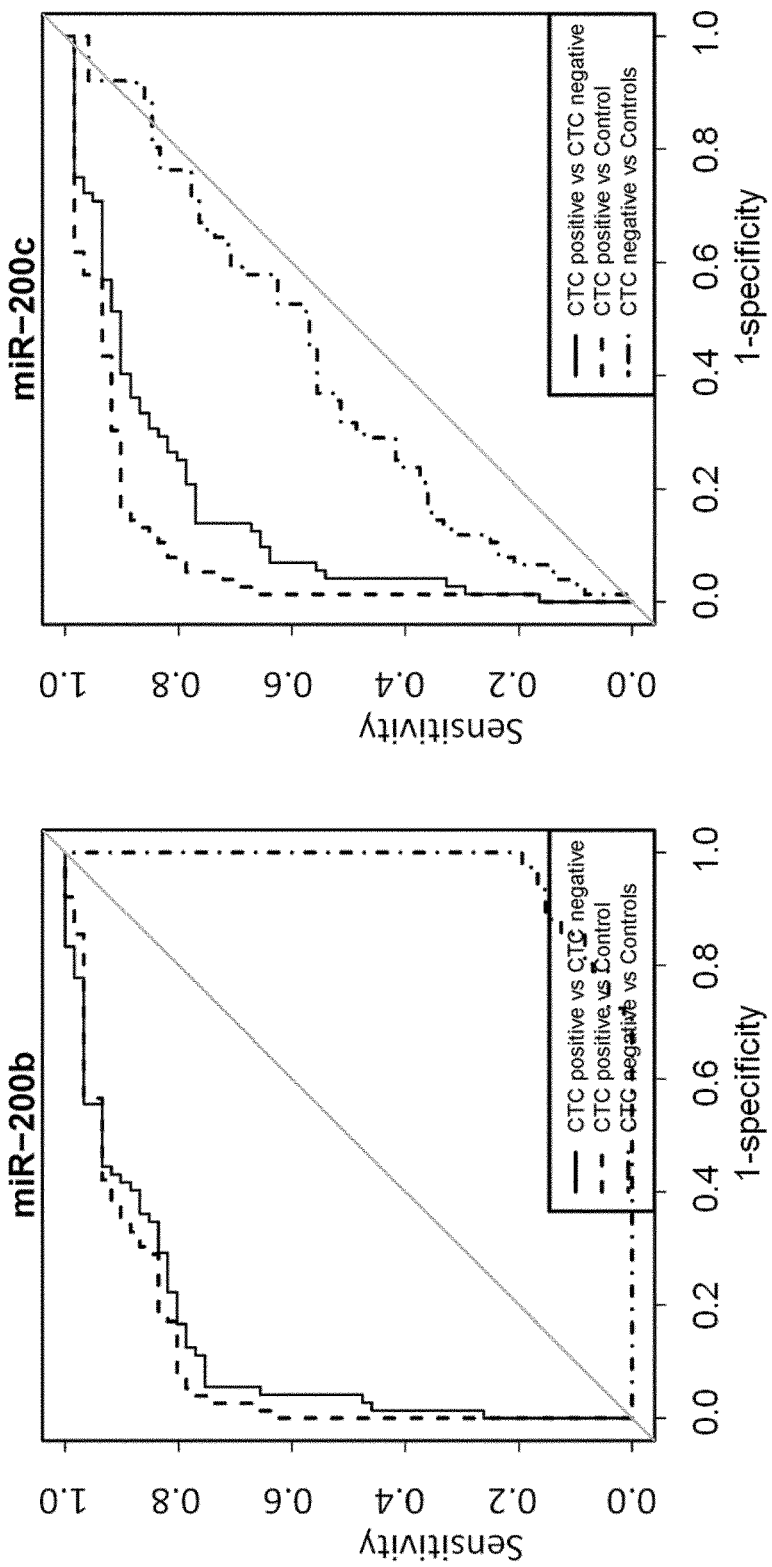
Figure 5:
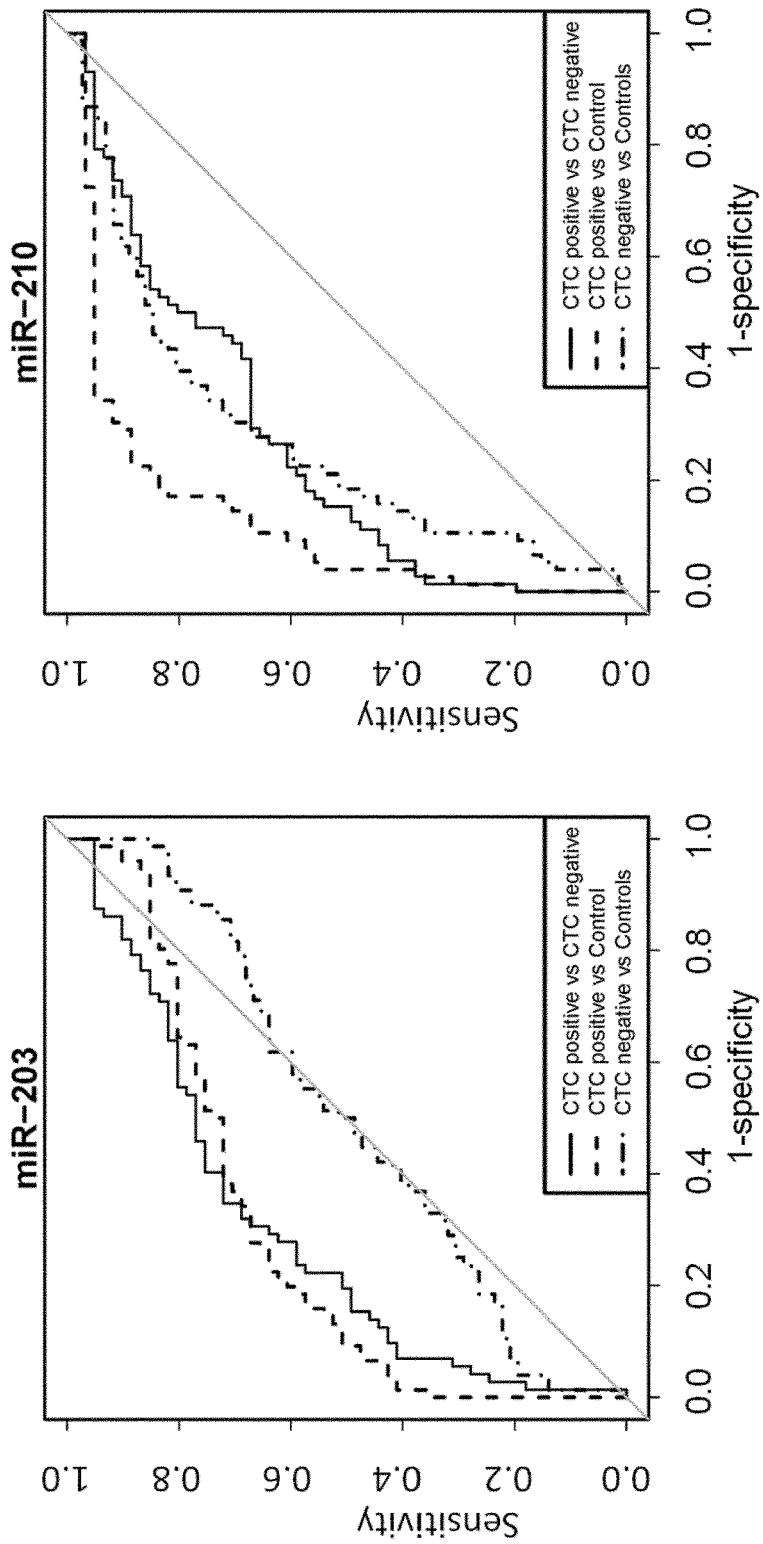
Figure 5D:
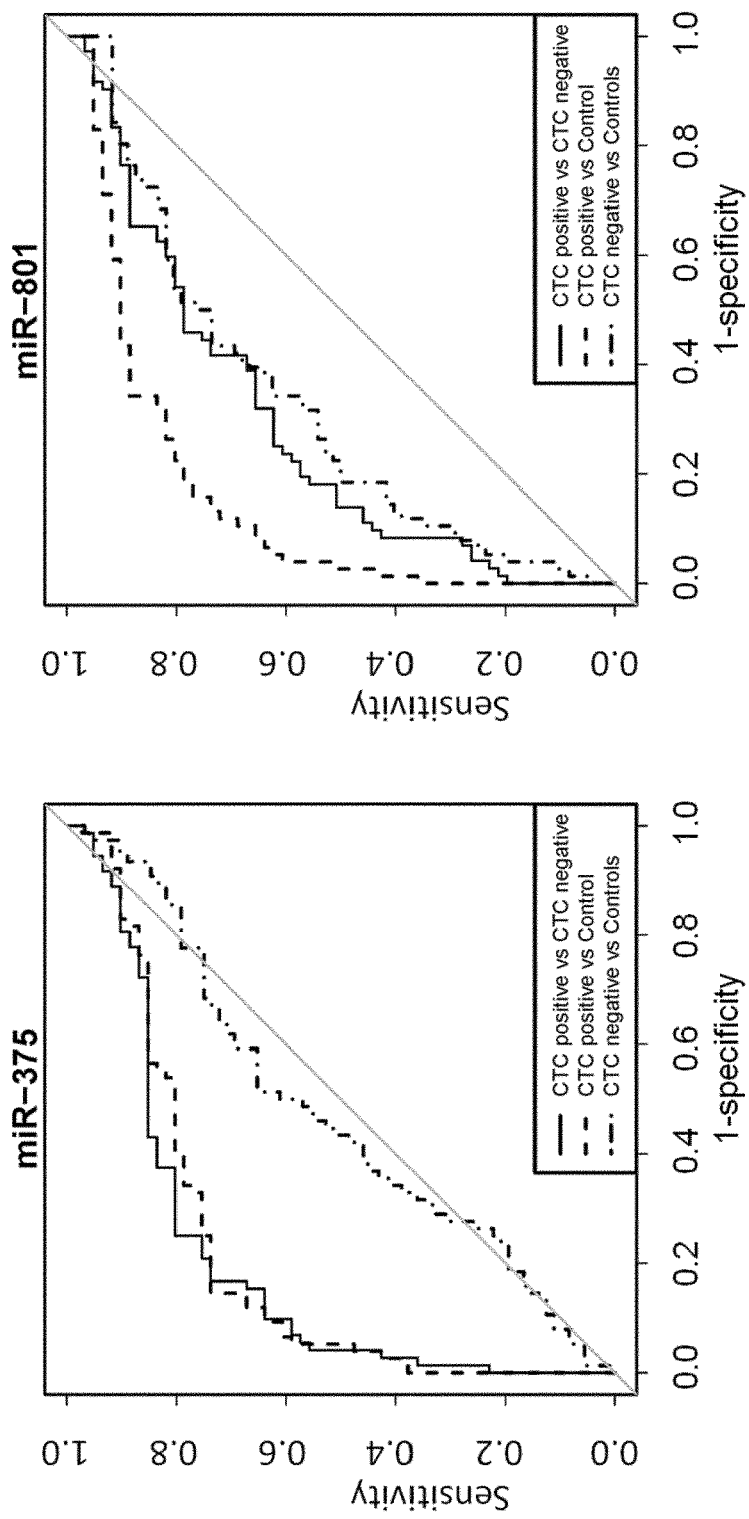
Figure 5:
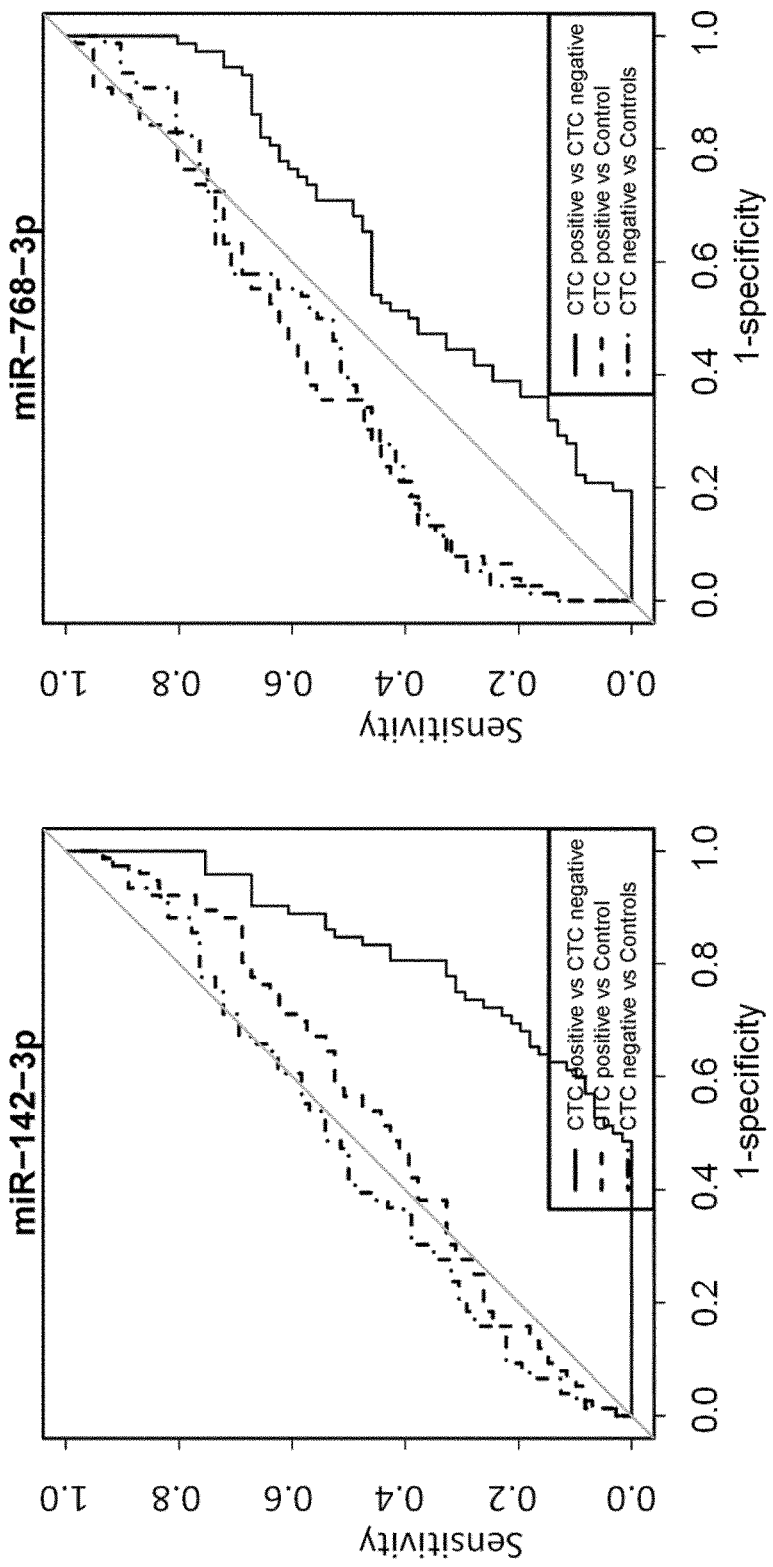
Figure 5H:
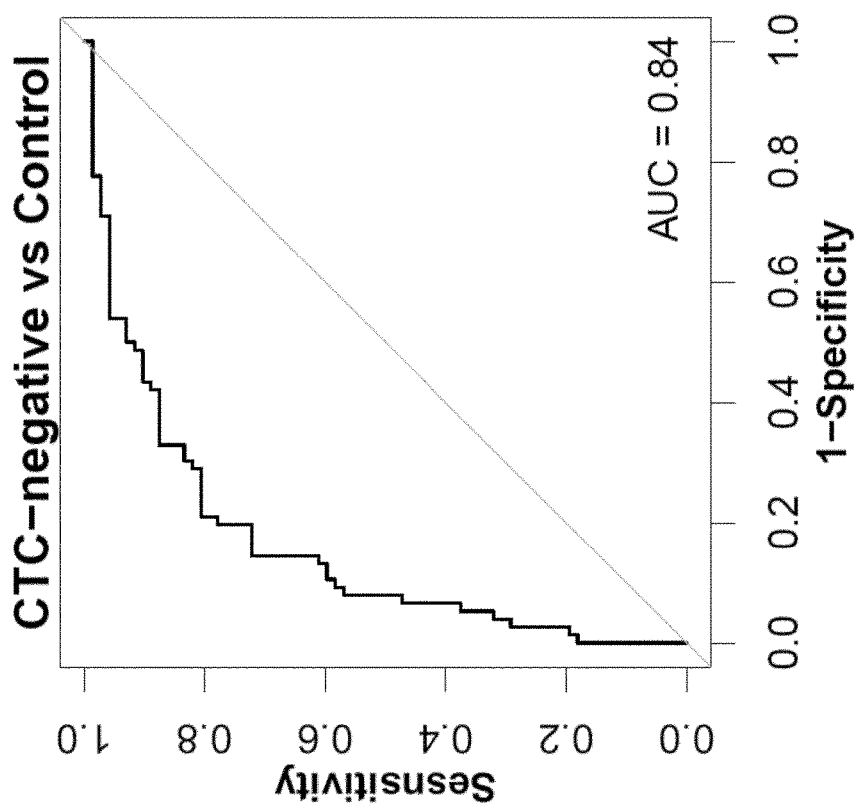

Combination of miR-141, miR-200b and miR-375 performed with equal accuracy (AUC=0.88). With an equal sensitivity and specificity as the models (80% and 83% respectively, FIG. 5F), we reckon miR-200b alone might be sufficient for distinguishing CTC-positive from CTC-negative cases. For CTC-positive cases versus controls, the predicted multivariable model with miR-141, miR-200b, miR-200c, miR-210 and miR-768-3p had a very high AUC of 0.95 (90% sensitivity and 91% specificity, FIG. 5G). Even though, individually the miRNAs could not differentiate CTC-negative cases from controls with high certainty, the model predicted combination of three miRNAs, miR-200c, miR-210 and miR-768-3p, had an appreciable AUC of 0.78 (80% sensitivity and 65% specificity) (FIG. 5H).

Example 14: Circulating miRNAs Correlate with CTC Counts

The eight miRNAs that were significantly upregulated in the CTC-positive and CTC-negative comparison, also evidenced a strong correlation to CTC counts. Spearman correlation analysis demonstrated lower Ct values, and thus higher miRNA expression, correlated with higher number of CTCs (p<0.00001). In contrast, miR-142-3p and miR-768-3p had very poor correlation to CTC numbers (ρ of −0.13 and −0.05 respectively), miR-16, which is considered as an endogenous control for breast cancer tissue, also had poor and no significant correlation to CTC numbers (ρ=−0.06, p=0.47) (Table 3).

TABLE 2

Validation of candidate miRNAs. Results of Wilcoxon rank sum tests with median fold change (FC = $2^{-\Delta Ct}$), corresponding two sided p value, and leave-one-out cross-validated area under the curve (AUC) estimates for the 10 candidate miRNAs.

|  | CTC-positive versus CTC-negative | | | CTC-positive versus Control | | | CTC-negative versus Control | | |
| --- | --- | --- | --- | --- | --- | --- | --- | --- | --- |
|  | FC | P | AUC | FC | P | AUC | FC | P | AUC |
| miR-141 | 26.17 | 8.27E−13 | 0.85 | 36.25 | 1.69E−16 | 0.90 | 1.39 | 6.75E−03 | 0.59 |
| miR-200a | 15.24 | 6.85E−13 | 0.85 | 15.78 | 7.34E−15 | 0.88 | 1.04 | 3.05E−01 | 0.47 |
| miR-200b | 11.63 | 9.53E−15 | 0.88 | 13.18 | 9.65E−17 | 0.91 | 1.13 | 8.52E−01 | 0.03 |
| miR-200c | 9.38 | 5.73E−13 | 0.86 | 14.22 | 1.54E−17 | 0.92 | 1.52 | 1.22E−02 | 0.59 |
| miR-203 | 4.06 | 6.37E−06 | 0.71 | 3.36 | 5.89E−06 | 0.71 | 0.83 | 2.47E−01 | 0.49 |
| miR-210 | 2.41 | 2.77E−07 | 0.74 | 5.17 | 2.29E−14 | 0.87 | 2.14 | 2.57E−07 | 0.73 |
| miR-375 | 4.96 | 5.98E−10 | 0.80 | 3.89 | 2.22E−09 | 0.79 | 0.78 | 1.27E−01 | 0.52 |
| miR-801 | 2.83 | 2.54E−06 | 0.72 | 4.99 | 5.91E−13 | 0.85 | 1.77 | 2.87E−05 | 0.67 |
| miR-142-3p | 1.16 | 4.44E−01 | 0.17 | 0.96 | 6.73E−01 | 0.45 | 0.83 | 1.72E−01 | 0.52 |
| miR-768-3p | 0.88 | 6.76E−01 | 0.35 | 0.68 | 6.12E−03 | 0.61 | 0.77 | 2.96E−02 | 0.58 |

Example 13: Circulating miRNAs Differentiate CTC-Positive from CTC-Negative MBC

Leave-one-out cross-validated ROC analysis predicted the ability of the investigated miRNAs to differentiate CTC-positive from CTC-negative cases, and CTC-positive cases from controls with high AUCs (FIG. 5A-E; Table 2). For CTC-positive versus CTC-negative cases, although a multivariable model comprising miR-141 and miR-200b was predicted (0.87), the AUC of miR-200b alone (0.88) was found to be marginally greater than that of the model.

TABLE 3

Correlation of miRNA and CTC counts. Spearman rank correlation of miRNA expression (Ct value) and number of CTCs.

|  | CTC counts | |
| --- | --- | --- |
|  | rho value | P |
| miR-141 | −0.55 | 2.29E−14 |
| miR-200a | −0.56 | 6.12E−15 |
| miR-200b | −0.61 | <2.2E−16 |
| miR-200c | −0.57 | 1.98E−15 |
| miR-203 | −0.43 | 8.98E−09 |
| miR-210 | −0.45 | 1.40E−09 |
| miR-375 | −0.53 | 3.72E−13 |

TABLE 3-continued

Correlation of miRNA and CTC counts. Spearman rank correlation of miRNA expression (Ct value) and number of CTCs.

|  | CTC counts | |
| --- | --- | --- |
|  | rho value | P |
| miR-801 | −0.39 | 2.04E−07 |
| miR-142-3p | −0.13 | 0.1 |
| miR-768-3p | −0.05 | 0.52 |
| miR-16 | −0.06 | 0.47 |

Example 15: Analysis of miRNA with Survival Data

Patients with metastatic breast cancer (MBC) were recruited into the study, and blood was collected. The patients were followed-up and monitored for progression by radiological methods (Eg. CT scans). Patients were classified as follows:
1. Progressive disease: Increase in size of tumor or spread of tumor to other regions
2. Stable disease: No change in size of tumor
3 Partial remission: Decrease in size of tumor
4. Complete remission: Tumor not discernible by radiological imaging Progression free survival (PFS) was defined as the time from enrollment into the study to progressive disease in months; Overall survival (OS) was defined as the time from enrollment into study to death in months; miRNA quantification: Eight miRNAs, namely miR-141, miR-200a, miR-200b, miR-200c, miR-203, miR-210, miR-375, and miR-801, that were significantly upregulated in CTC positive when compared to CTC negative were quantified in each sample as described in Example 4.

Statistical analysis: Correlation of miRNA expression to PFS and OS were assessed by both Cox proportional hazard model and logrank test. Cox models assume proportional hazards and a linear relationship between miRNA expression and PFS hazard, and calculates the log Hazard ratio and the corresponding P value (Cox, D. R. and D. Oakes. Analysis of Survival Data. London: Chapman and Hall, 1984). In the logrank test the relationship between miRNA expression and PFS hazard can be explained by a categorization into the two groups (those with Ct>median CT, and those with Ct<median Ct). Contrary to the Cox model, we do not assume a linear relationship between miRNA expression values and PFS (N. Mantel. Evaluation of survival data and two new rank order statistics arising in its consideration. Cancer Chemotherapy Reports, 1996 50 (3): 163-70).

TABLE 4

P values from log rank test estimating the association between miRNA levels and progression-free (PFS) and overall survival (OS).

|  | ITS | OS |
| --- | --- | --- |
| miR-141 | 4.58E−02 | 6.77E−06 |
| miR-200a | 6.69E−05 | 1.24E−07 |
| miR-200b | 1.74E−05 | 3.72E−09 |
| miR-200c | 3.06E−05 | 1.06E−09 |
| miR-203 | 9.20E−02 | 7.28E−03 |
| miR-210 | 1.07E−01 | 2.30E−04 |
| miR-375 | 1.45E−03 | 3.96E−05 |
| miR-801 | 1.51E−02 | 2.45E−05 |
| CTC | 1.70E−03 | 4.49E−07 |

Example 16: Prediction of Therapy Success in MBC Patients

Figure 10:
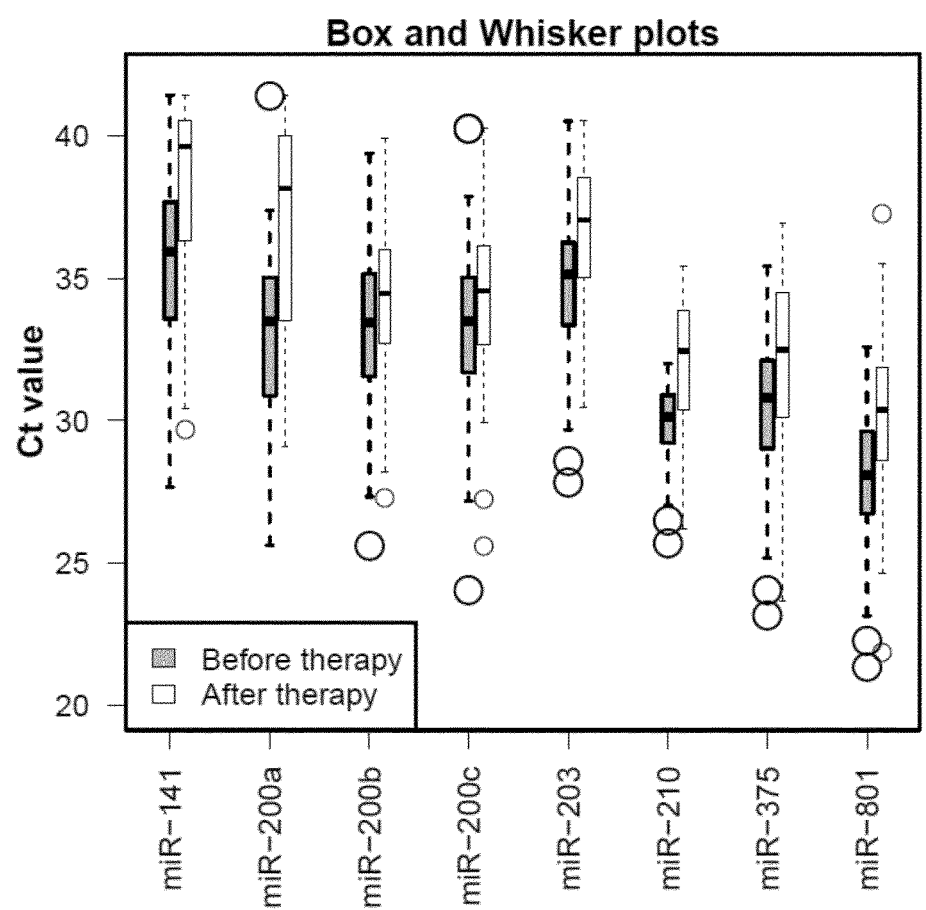
FIG. 10: Box and whisker plots showing a significant decrease in the levels of the eight miRNAs measured in metastatic breast cancer patients before and after one round of therapy.

It was described above that eight miRNAs (miR-141, miR-200a, mir-200b, miR-200c, miR-203, miR-210, miR-375, miR-801) that could serve as prognostic markers in metastatic breast cancer (MBC) patients. It was further analysed if the above miRNAs could be useful in monitoring therapy response. For this, these 8 miRNAs were measured in 76 patient samples (plasma) after one round of herapy, wherein appropriate treatment for each patient was selected from chemotherapy, radiotherapy, and/or hormone therapy (FIG. 10).

Figure 11:
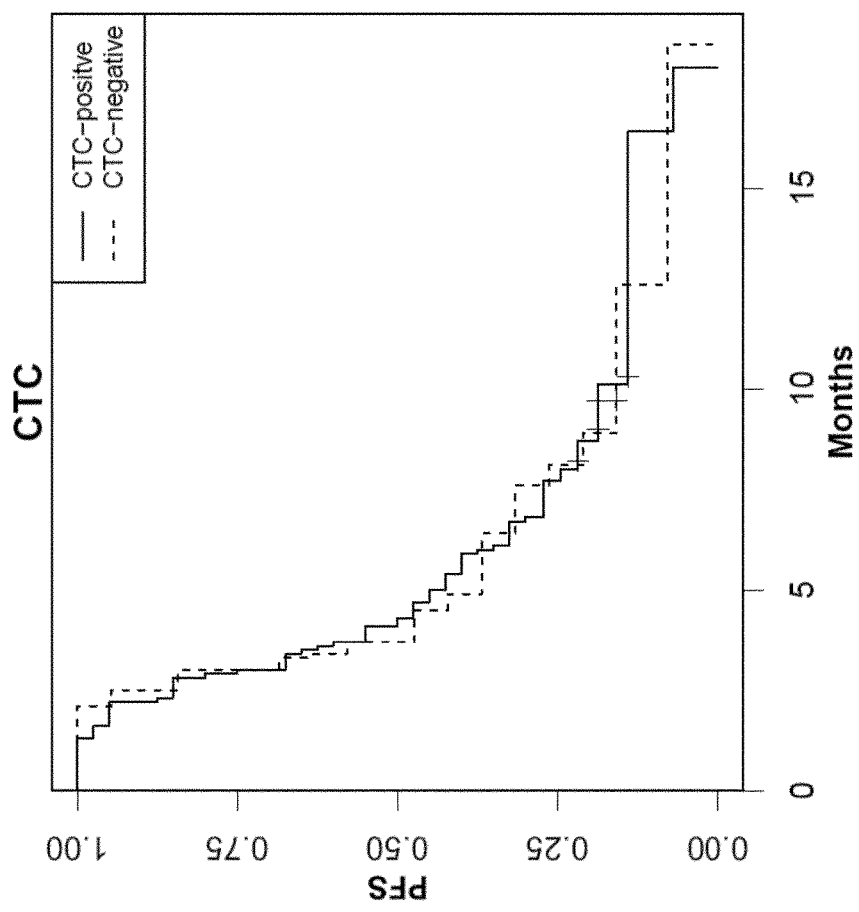
FIG. 11: Kaplan-Meier curves of miRNAs indicated for progression free survival (PFS) in metastatic breast cancer patients after therapy. Kaplan-Meier curves of miRNA amounts stratified based on the Ct values as lower quartile (or 25 percentile) and rest. Kaplan-Meier curves show that the lower the Ct value, i.e., the higher the expression of the miRNA, the lower is the probability of progression-free, and overall survival.
Figure 12:
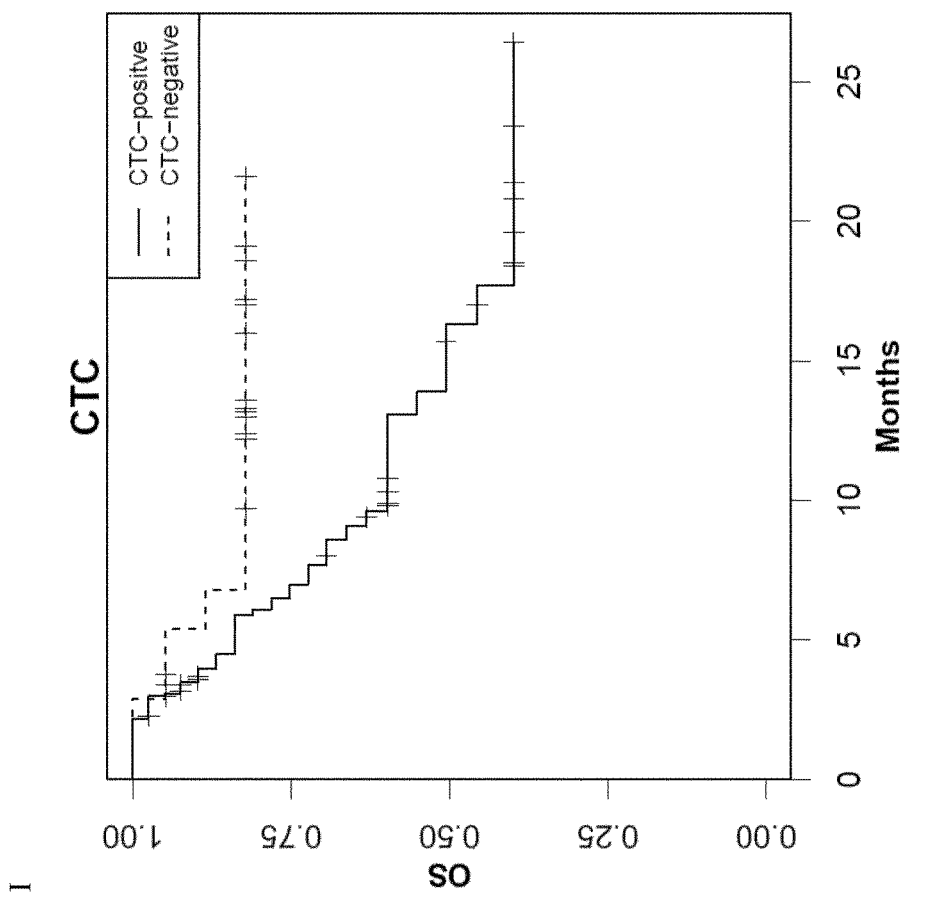
FIG. 12: Kaplan-Meier curves of miRNAs indicated for overall survival (OS) in metastatic breast cancer patients after therapy. Kaplan-Meier curves of miRNA amounts stratified based on the Ct values as lower quartile (or 25 percentile) and rest. Kaplan-Meier curves show that the lower the Ct value, i.e., the higher the expression of the miRNA, the lower is the probability of progression-free, and overall survival.

Correlation of miRNA amounts and also circulating tumour cells (CTC) after therapy to progression free survival (PFS) and overall survival (OS) was established by log-rank test after stratifying data as lower quartile and rest (miRNAs) or CTC-positive and CTC-negative (CTC), and the corresponding Kaplan-meler curves are presented in FIG. 11 and FIG. 12.

miR-200b performed the best among all miRNAs; comparison of the cox regression model with miR-200b or CTCs by ANOVA test is shown in Table 6:

TABLE 5

P values from log rank test estimating the association between miRNA levels after therapy and progression-free (PFS) and overall survival (OS).

|  | PFS | OS |
| --- | --- | --- |
| miR-141 | 0.018 | 6.65E−08 |
| miR-200a | 0.024 | 3.13E−04 |
| miR-20011 | 0.003 | 9.00E−07 |
| miR-200c | 0.007 | 5.92E−04 |
| miR-203 | 0.094 | 6.60E−03 |
| miR-210 | 0.021 | 1.64E−03 |
| miR-375 | 0.146 | 5.34E−04 |
| miR-801 | 0.482 | 3.81E−03 |
| CTC | 0.018 | 6.65E−08 |

TABLE 6 correlation analysis and ANOVA test

|  | progression-free survival | | overall survival | |
| --- | --- | --- | --- | --- |
|  | miRNA200b | CTC | miRNA200b | CTC |
| P-value | 0.005 | 0.28 | 5.2 E−05 | 0.019 |
| Regression coefficient | 8.847 | 0.285 | 1.87 | 1.05 |
| ANOVA | <2.2 E−16 | | <2.2 E−16 | |

Apparently, the miRNAs of the present invention outperform CTC as a marker for PFS and/or OS.

II. Cohort II

Cohort II consisted of 120 primary breast cancer patients, 30 women with benign breast tumors and 60 healthy female volunteers who served as controls. Except where otherwise noted, samples were obtained and processed as described for cohort I.

Example 17: miRNA Profiling Revealing Further Putative Marker Candidates for Breast Cancer Detection in Plasma The initial screening step using TLDA arrays was similar to example 7, using data from 10 early stage breast cancer patients as well as 10 healthy controls. Quality control plots (Pearson's correlations across samples and principal components analysis) identified one control sample (B024) as an outlier, which was then removed from further statistical analysis. Raw Ct values from TLDAs were quantile normalized so that the values from different runs would have the same distribution and could be easily compared. Following quantile normalization and filtering of undetermined miRNAs (Ct>35 across all the samples), data from TLDA microfluidic cards A and cards B were combined for further analysis. Duplicate miRNA measurements were averaged and a total of 402 miRNAs remained for statistical analysis. Early stage breast cancer patients and healthy controls were compared using Limma analysis and 38 circulating miRNAs were found to be significantly different between these two groups. A list of the significant miRNAs can be found in Table 7 together with their (i) p-values, (ii) p-values adjusted for multiple testing according to the method of Benjamini-Hochberg (indicating false discovery rates, FDRs), (iii) mean Ct values for both investigated groups and (iv) differences in mean Ct values (ΔCt) between the control and cases group

TABLE 7

Circulating miRNAs deregulated in the plasma of early stage breast cancer patients compared to healthy controls in TLDA analysis (Limma test). Circulating miRNAs selected for further investigation are in bold and finally validated miRNAs are underlined.

| miRNA | p-value | False discovery rate | mean Ct (controls) | mean Ct (cases) | ΔCt* |
|---|---|---|---|---|---|
| hsa-miR-148b | 0.0005 | 0.07 | 31.6 | 30.4 | 1.2 |
| hsa-miR-328 | 0.0004 | 0.07 | 28.6 | 27.9 | 0.7 |
| hsa-miR-376c | 0.0002 | 0.07 | 32.0 | 30.4 | 1.6 |
| hsa-miR-652 | 0.0008 | 0.08 | 31.9 | 30.7 | 1.2 |
| hsa-miR-320 | 0.001 | 0.11 | 24.0 | 24.8 | −0.8 |
| hsa-miR-145 | 0.004 | 0.23 | 28.1 | 27.1 | 1.0 |
| hsa-miR-339-3p | 0.004 | 0.23 | 30.9 | 30.2 | 0.7 |
| hsa-miR-193a-3p | 0.007 | 0.28 | 38.3 | 40.0 | −1.7 |
| hsa-miR-206 | 0.007 | 0.28 | 29.9 | 31.7 | −1.8 |
| hsa-miR-801 | 0.007 | 0.28 | 30.6 | 28.4 | 2.2 |
| hsa-miR-139-3p | 0.010 | 0.38 | 29.8 | 34.9 | −5.1 |
| hsa-miR-221 | 0.015 | 0.38 | 28.2 | 27.7 | 0.5 |
| hsa-miR-376a | 0.014 | 0.38 | 32.9 | 31.5 | 1.4 |
| hsa-miR-138-1* | 0.013 | 0.38 | 28.0 | 28.7 | −0.7 |
| hsa-miR-190b | 0.015 | 0.38 | 33.9 | 32.9 | 1.0 |
| hsa-miR-409-3p | 0.013 | 0.38 | 34.0 | 32.3 | 1.7 |
| hsa-miR-424 | 0.016 | 0.39 | 38.3 | 35.3 | 3.0 |
| hsa-miR-184 | 0.020 | 0.42 | 39.4 | 36.7 | 2.7 |
| hsa-miR-875-5p | 0.019 | 0.42 | 34.0 | 33.1 | 0.9 |
| hsa-miR-93* | 0.024 | 0.46 | 30.2 | 31.2 | −1.0 |
| hsa-miR-526b* | 0.024 | 0.46 | 36.6 | 38.6 | −2.0 |
| hsa-let-7c | 0.036 | 0.52 | 30.0 | 30.6 | −0.6 |
| hsa-miR-18a | 0.038 | 0.52 | 29.2 | 28.5 | 0.7 |
| hsa-miR-29a | 0.049 | 0.52 | 26.8 | 27.3 | −0.5 |
| hsa-miR-29c | 0.043 | 0.52 | 30.3 | 30.8 | −0.5 |
| hsa-miR-127-3p | 0.047 | 0.52 | 33.1 | 31.2 | 1.9 |
| hsa-miR-190 | 0.042 | 0.52 | 36.4 | 34.2 | 2.2 |
| hsa-miR-323-3p | 0.049 | 0.52 | 31.0 | 30.5 | 0.5 |
| hsa-miR-485-3p | 0.040 | 0.52 | 32.0 | 31.3 | 0.7 |
| hsa-miR-519a | 0.031 | 0.52 | 35.7 | 38.1 | −2.4 |
| hsa-miR-548d-3p | 0.040 | 0.52 | 40.0 | 38.8 | 1.2 |
| hsa-miR-579 | 0.035 | 0.52 | 32.3 | 33.1 | −0.8 |
| hsa-miR-598 | 0.041 | 0.52 | 31.4 | 32.0 | −0.6 |
| hsa-miR-200a* | 0.042 | 0.52 | 37.6 | 40.0 | −2.4 |
| hsa-miR-148b* | 0.034 | 0.52 | 38.8 | 36.9 | 1.9 |
| hsa-miR-34a* | 0.049 | 0.52 | 31.3 | 32.3 | −1.0 |
| hsa-miR-941 | 0.042 | 0.52 | 37.8 | 40.0 | −2.2 |
| hsa-miR-188-5p | 0.047 | 0.52 | 28.7 | 29.2 | −0.5 |

*ΔCt = mean Ct$_{controls}$ − mean Ct$_{cases}$

Example 18: miR-127-3p, miR-148b, miR-376a, miR-376c, mlR-409-3p, miR-652 and miR-801 are Upregulated in Plasma of Breast Cancer Patients The following criteria were applied to choose the best candidates for marker validation studies in plasma: unadjusted p<0.05, mean Ct<33 in at least one investigated group (as miRNA expression should be stably detectable in at least one group) and (iii) IACtI>1 (indicating that the miRNA amounts in the patient and control plasma differ markedly) (Table 7). The application of these criteria resulted in nine candidates for validation: miR-127-3p, miR-139-3p, miR-148b, miR-206, miR-376a, miR-376c, miR-409-3p, miR-652 and miR-801.

Figure 7:
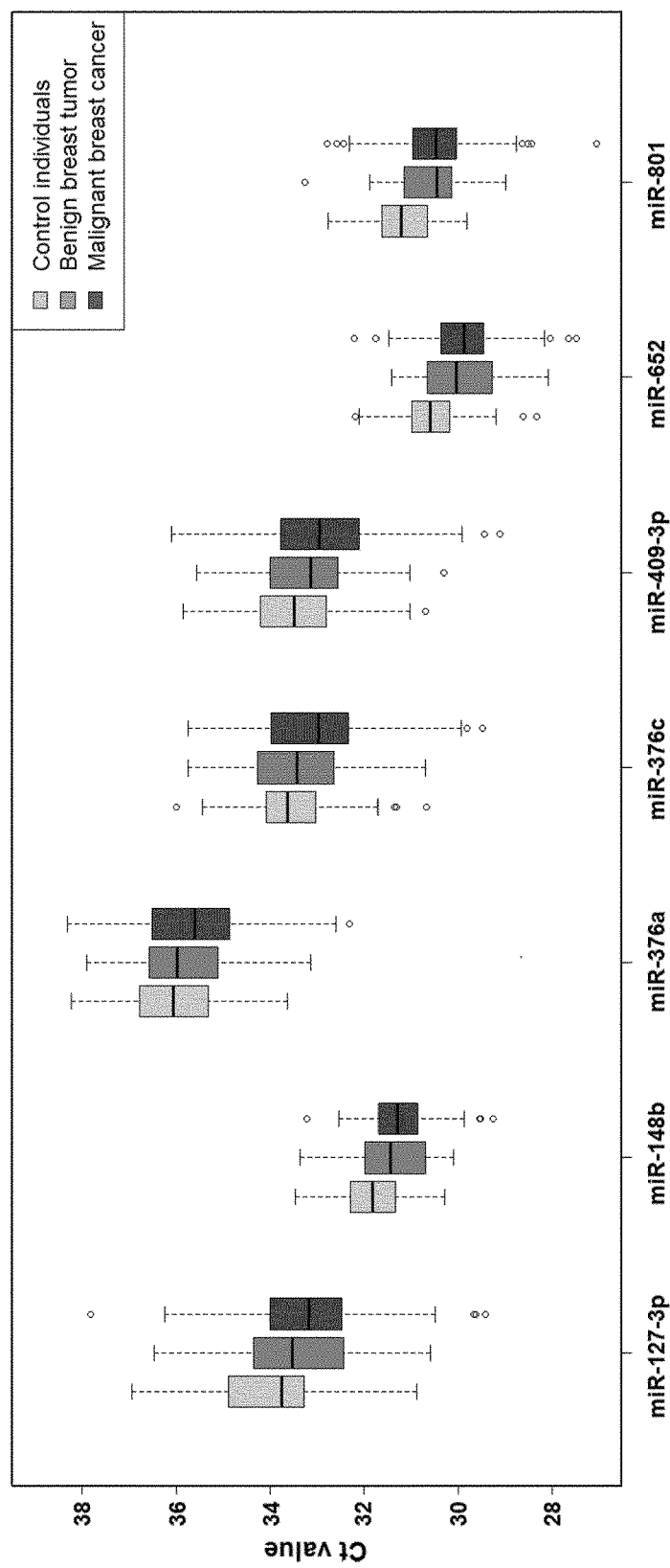
FIGS. 7 to 9 show data obtained from patient cohort II.

In validation studies, circulating miR-139-3p and miR-206 did not reach statistical significance, but an investigation of a validation cohort (n=210) consisting of 30 women with benign and 120 with malignant breast tumors, as well as 60 healthy controls showed that circulating miR-127-3p (P<0.001), miR-148b (P<0.0001), miR-376a (P=0.03), miR-376c (P=0.03), miR-409-3p (P=0.005), miR-652 (P<0.0001) and miR-801 (P<0.0001) have increased levels in the plasma of women with breast cancer when compared to healthy controls (FIG. 7). Additionally, circulating miR-148b (P=0.02), miR-652 (P=0.01) and miR-801 (P=0.003) differed significantly even in the plasma of women with benign breast tumors when compared to healthy women (FIG. 7).

Example 19: Diagnostic Potential of Mir-127-3p, miR-148b, miR-376a, miR-376c, miR-409-3p, miR-652 and miR-801 in Plasma ROC curve analysis was performed to evaluate the diagnostic potential of mir-127-3p, miR-148b, miR-376a, miR-376c, miR-409-3p, miR-652 and miR-801 for breast cancer detection in blood plasma. The discriminatory power between tumor and control samples is depicted by the areas under the curves (AUC).

Figure 8:
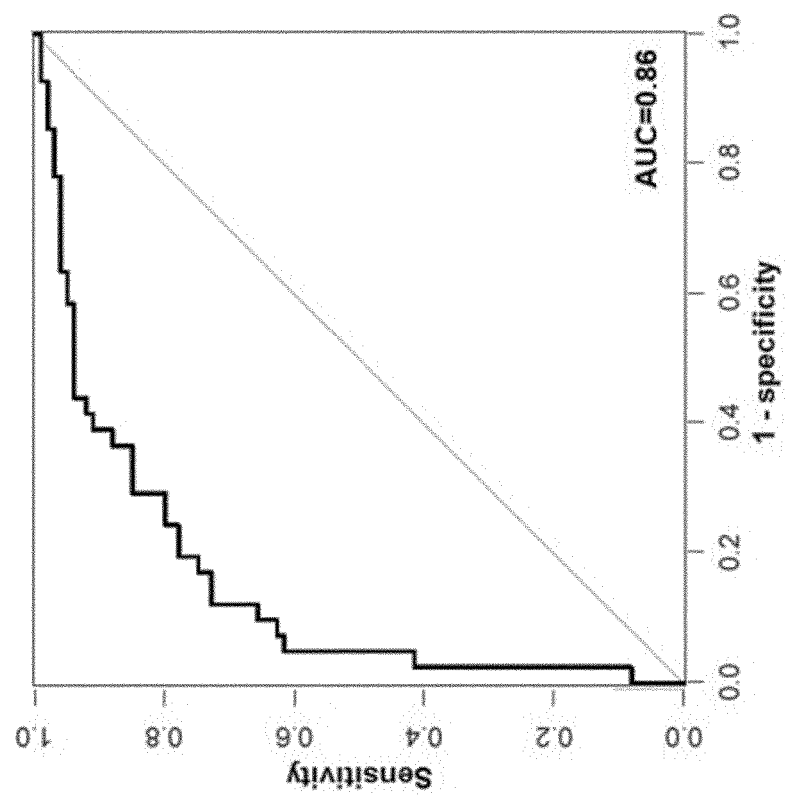

Individually, miR-127-3p had an AUC of 0.65 (95% CI: 0.57-0.73), miR-148b of 0.70 (95% CI: 0.62-0.78), miR-376a of 0.59 (95% CI: 0.51-0.67), miR-376c of 0.59 (95% CI; 0.51-0.67), miR-409-3p of 0.62 (95% CI: 0.54-0.70), miR-652 of 0.75 (95% CI: 0.67-0.82) and miR-801 of 0.72 (95% CI: 0.65-0.80) (FIG. 8 A-G).

The combination of all seven miRNAs yielded the best discriminatory power with AUC=0.81 (95% CI=0.75-0.88) for the detection of breast tumors (FIG. 8 H). In younger women (up to the age of 50) these circulating miRNAs performed superiorly and had an even higher accuracy (AUC=0.86: 95% CI=0.79-0.93) for breast tumor detection (FIG. 8I).

Example 20: Correlation Between Plasma miRNAs

Inter-relationships between miRNA expressions were investigated by computing Spearman rank correlation coefficients (p). Four out of seven validated miRNAs (miR-127-3p, miR-376a, miR-376c and miR-409-3p) originate from the same miRNA cluster located on the chromosomal region 14q32 and their plasma levels were found to correlate to each other strongly. Table 8 provides a detailed representation of the various miRNA inter-correlations. Apart from the four miRNAs belonging to the same miRNA cluster, circulating miR-148b correlated considerably with miR-127-3p and miR-652, whereas miR-801 showed no significant correlations except for a slight correlation to miR-148b levels.

Figure 9:
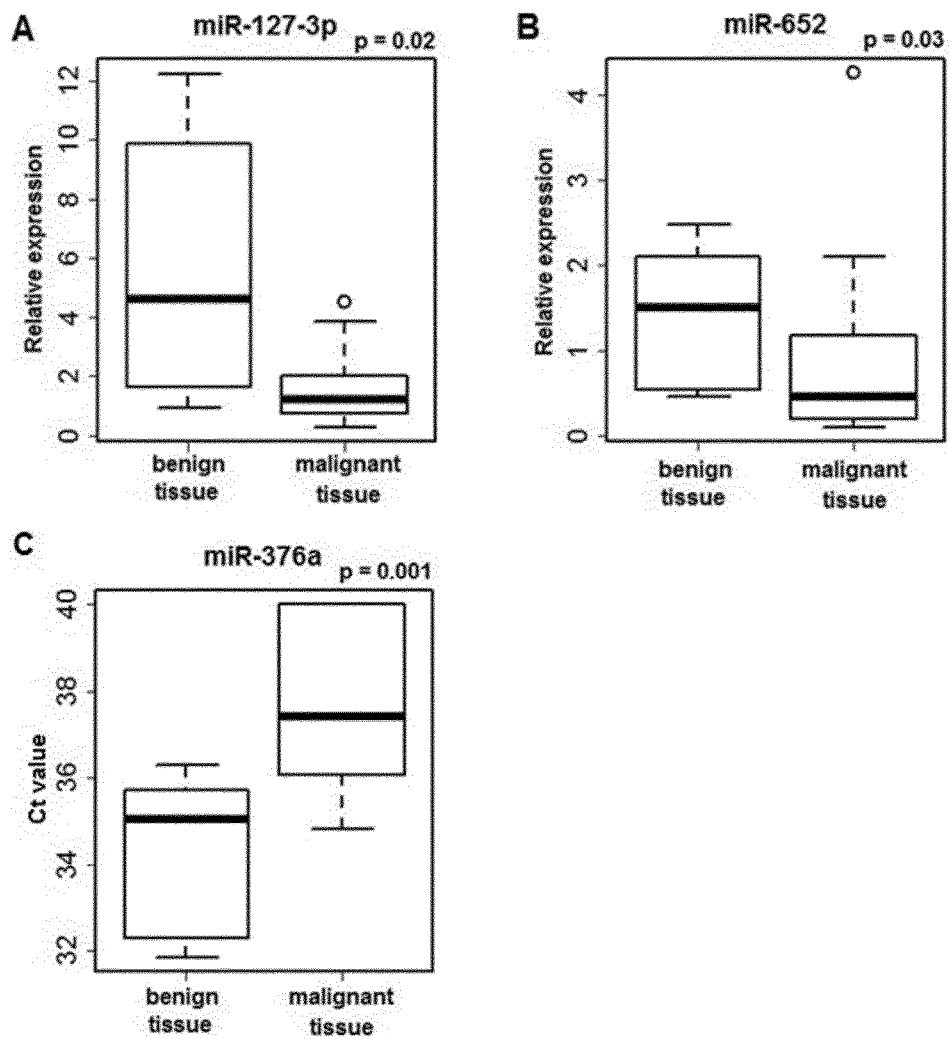

Example 21: miR-127-3p, miR-376a and miR-652 are Downregulated in Malignant Primary Breast Cancer Tissue A total of 24 primary breast cancer surgery tissue samples and 8 benign breast biopsies were analyzed for their miR-127-3p, miR-376a and miR-652 expression levels. A comparison of these two sample groups showed that, in contrast to plasma, miR-127-3p (p=0.02), miR-376a (p=0.001) and miR-652 (p=0.03) were downregulated in malignant breast cancer tissue in comparison to benign breast tissue samples (FIG. 9.A-C).

TABLE 8

Spearman correlation rank coefficients (p) and confidence intervals (95% CI), as well as P values for selected miRNA pairs.

|  | miR-148b | miR-376a | miR-376c | miR-409-3p | miR-652 | miR-801 |
|---|---|---|---|---|---|---|
| miR-127-3p | p = 0.62<br>95% CI = 0.49-0.72<br>P < 0.0001 | p = 0.85<br>95% CI = 0.79-0.89<br>P < 0.0001 | p = 0.92<br>95% CI = 0.88-0.94<br>P < 0.0001 | p = 0.89<br>95% CI = 0.84-0.92<br>P < 0.0001 | p = 0.48<br>95% CI = 0.32-0.61<br>P < 0.0001 | p = 0.06<br>95% CI = (−0.13)-0.24<br>P = 0.55 |
| miR-148b | xxx | p = 0.55<br>95% CI = 0.41-0.67<br>P < 0.0001 | p = 0.59<br>95% CI = 0.45-0.70<br>P < 0.0001 | p = 0.56<br>95% CI = 0.42-0.68<br>P < 0.0001 | p = 0.78<br>95% CI = 0.70-0.84<br>P < 0.0001 | p = 0.24<br>95% CI = 0.06-0.41<br>P = 0.0077 |
| miR-376a | p = 0.55<br>95% CI = 0.41-0.67<br>P < 0.0001 | xxx | p = 0.87<br>95% CI = 0.81-0.91<br>P < 0.0001 | p = 0.84<br>95% CI = 0.77-0.88<br>P < 0.0001 | p = 0.43<br>95% CI = 0.27-0.57<br>P < 0.0001 | p = 0.04<br>95% CI = (−0.22)-0.15<br>P = 0.69 |
| miR-376c | p = 0.59<br>95% CI = 0.45-0.70<br>P < 0.0001 | p = 0.87<br>95% CI = 0.81-0.91<br>P < 0.0001 | xxx | p = 0.91<br>95% CI = 0.87-0.94<br>P < 0.0001 | p = 0.43<br>95% CI = 0.26-0.57<br>P < 0.0001 | p = 0.03<br>95% CI = (−0.15)-0.22<br>P = 0.73 |
| miR-409-3p | p = 0.56<br>95% CI = 0.42-0.68<br>P < 0.0001 | p = 0.84<br>95% CI = 0.77-0.88<br>P < 0.0001 | p = 0.91<br>95% CI = 0.87-0.94<br>P < 0.0001 | xxx | p = 0.44<br>95% CI = 0.28-0.58<br>P < 0.0001 | p = 0.07<br>95% CI = (−0.11)-0.25<br>P = 0.44 |
| miR-652 | p = 0.78<br>95% CI = 0.70-0.84<br>P < 0.0001 | p = 0.43<br>95% CI = 0.27-0.57<br>P < 0.0001 | p = 0.43<br>95% CI = 0.26-0.57<br>P < 0.0001 | p = 0.44<br>95% CI = 0.28-0.58<br>P < 0.0001 | xxx | p = 0.09<br>95% CI = (−0.10)-0.27<br>P = 0.34 |

Example 22: Prediction of Therapy Success in MBC Patients

It was described above that eight miRNAs (miR-141, miR-200a, mir-200b, miR-200c, miR-203, miR-210, miR-375, miR-801) that could serve as prognostic markers in metastatic breast cancer (MBC) patients. It was further analysed if the above miRNAs could be useful in monitoring therapy response. For this, these 8 miRNAs were measured in 76 patient samples (plasma) after one round of chemotherapy (FIG. 10).

Correlation of miRNA amounts and also circulating tumour cells (CTC) after therapy to progression free survival (PFS) and overall survival (OS) was established by log-rank test after stratifying data as lower quartile and rest (miRNAs) or CTC-positive and CTC-negative (CTC), and the corresponding Kaplan-meier curves are presented in FIG. 11 and FIG. 12.

miR-200b performed the best among all miRNAs; comparison of the cox regression model with miR-200b or CTCs by ANOVA test is shown in Table 9:

TABLE 9 correlation analysis and ANOVA test

|  | progression-free survival | | overall survival | |
|---|---|---|---|---|
|  | miRNA200b | CTC | miRNA200b | CTC |
| P-value | 0.005 | 0.28 | 5.2 E−05 | 0.019 |
| Regression coefficient | 8.847 | 0.285 | 1.87 | 1.05 |
| ANOVA | <2.2 E−16 | | <2.2 E−16 | |

Apparently, the miRNAs of the present invention outperform CTC as a marker for PFS and/or OS.

---

The invention claimed is:

1. A method for diagnosing and treating metastasizing breast cancer in a subject comprising the steps of:
   (a) contacting a cell free serum or plasma sample from the subject with one or more detection agents that specifically interact with at least one miRNA selected from the group consisting of miR-801, miR-141, miR-142-3p, miR-200a, miR-200b, miR-200c, miR-203, miR-210, miR-375, and miR-768-3p,
   (b) quantifying the amount of the at least one miRNA in the serum or plasma sample;
   (c) comparing the amount with an amount of the at least one miRNA in a reference, whereby an increased amount of the at least one miRNA in the serum or plasma sample as compared to the reference is indicative of metastasizing breast cancer; and
   (d) administering at least one of chemotherapy, antihormone therapy, targeted therapy, immunotherapy, and radiation therapy to the diagnosed patient.

2. The method of claim 1, wherein the at least one miRNA is selected from the group consisting of miR-801, miR-203, and miR-768-3p, or the at least one miRNA is selected from:
   (i) a group consisting of miR-142-3p and miR-768-3p,
   (ii) a group consisting of miR-203,
   (iii) a group consisting of miR-375,
   (iv) a group consisting of miR-210 and miR-801, and
   (v) a group consisting of miR-141, miR-200a, miR-200b, miR-200c.

3. The method of claim 1, wherein the at least one miRNA comprises:
   (i) miR-141, miR-200b, miR-375, and miR-801,
   (ii) miR-141, miR-200b, miR-375, miR-801, miR-203, and miR-768-3p,
   (iii) miR-141, miR-200c, miR-210, miR-801, and miR-768-3p,
   (iv) miR-141, miR-200b, miR-142-3p, and miR-768-3p,
   (v) miR-141, miR-200b, miR-210, miR-375, miR-801, miR-142-3p, and miR-768-3p, or
   (vi) miR-141, miR-200b, miR-200c, miR-210, miR-375, miR-203, miR-801, miR-142-3p, and miR-768-3p.

4. The method of claim 1, wherein the at least one miRNA is a combination comprising at least two miRNAs selected from the group consisting of:
   (i) miR-141 and miR-200b,
   (ii) miR-141, miR-200b, and miR-200c,
   (iii) miR-141, miR-200b, miR-210, and miR-200c,
   (iv) miR-141, miR-200b, miR-210, miR-768-3p, and miR-200c,
   (v) miR-200c, miR-210, and miR-768-3p, and
   (vi) miR-200c and miR-210.

* * * * *